US012753420B2

(12) United States Patent
Chang et al.

(10) Patent No.: US 12,753,420 B2
(45) Date of Patent: Oct. 6, 2026

(54) METHOD FOR MODULATING RNA SPLICING BY INDUCING BASE MUTATION AT SPLICE SITE OR BASE SUBSTITUTION IN POLYPYRIMIDINE REGION

(71) Applicant: SHANGHAI INSTITUTES FOR BIOLOGICAL SCIENCES, CHINESE ACADEMY OF SCIENCES, Shanghai (CN)

(72) Inventors: Xing Chang, Shanghai (CN); Juanjuan Yuan, Shanghai (CN); Yunqing Ma, Shanghai (CN)

(73) Assignee: SHANGHAI INSTITUTES FOR BIOLOGICAL SCIENCES, CHINESE ACADEMY OF SCIENCES, Shanghai (CN)

( * ) Notice: Subject to any disclaimer, the term of this patent is extended or adjusted under 35 U.S.C. 154(b) by 1671 days.

(21) Appl. No.: 16/982,017

(22) PCT Filed: Jul. 24, 2018

(86) PCT No.: PCT/CN2018/096810
§ 371 (c)(1),
(2) Date: May 14, 2021

(87) PCT Pub. No.: WO2019/020007
PCT Pub. Date: Jan. 31, 2019

(65) Prior Publication Data

US 2021/0355508 A1 Nov. 18, 2021

(30) Foreign Application Priority Data

Jul. 25, 2017 (CN) ........................ 201710611651.8

(51) Int. Cl.

| | |
|---|---|
| ***C12N 15/90*** | (2006.01) |
| ***A61K 31/7088*** | (2006.01) |
| ***A61K 38/46*** | (2006.01) |
| ***A61K 38/50*** | (2006.01) |
| ***A61K 48/00*** | (2006.01) |
| ***C12N 9/22*** | (2006.01) |
| ***C12N 9/78*** | (2006.01) |
| ***C12N 15/11*** | (2006.01) |
| ***C12N 15/52*** | (2006.01) |
| ***C12N 15/62*** | (2006.01) |

(52) U.S. Cl.
CPC ........ *C12N 15/907* (2013.01); *A61K 31/7088* (2013.01); *A61K 38/465* (2013.01); *A61K 38/50* (2013.01); *A61K 48/0066* (2013.01); *C12N 9/22* (2013.01); *C12N 9/78* (2013.01); *C12N 15/11* (2013.01); *C12N 15/111* (2013.01); *C12N 15/52* (2013.01); *C12N 15/62* (2013.01); *C12Y 305/04001* (2013.01); *C07K 2319/09* (2013.01); *C12N 2310/20* (2017.05)

(58) Field of Classification Search
None
See application file for complete search history.

(56) References Cited

U.S. PATENT DOCUMENTS 8,871,918 B2 * 10/2014 Sazani .................... A61P 21/04
536/23.1

FOREIGN PATENT DOCUMENTS

| | | |
|---|---|---|
| CN | 107043779 A | 8/2017 |
| WO | 2017070632 A2 | 4/2017 |

OTHER PUBLICATIONS

Bannikov et al., "CRISPR/CAS(, the King of Genome Editing Tools" 51(4) Molecular Biology 514-525 (Year: 2017).*
Gee et al., "Cellular Reprogramming, Genome Editing, and Alternative CRISPR Cas9 Technologies for Precise Gene Therapy of Duchenne Muscular Dystrophy" 2017 Stem Cells International 8765154, 1-11 (Year: 2017).*
Ma, Yunqing et al., "Targeted AID-Mediated Mutagenesis (TAM)—A New Technology for DNA Base Editing in Mammalian Cells", Chinese Journal of Cell Biology, vol. 39, No. 3, pp. 255-260; Feb. 27, 2017.
Ma, Yunqing et al. "Targeted AID-Mediated Mutagenesis (TAM) Enables Efficient Genomic Diversification in Mammalian Cells", Nature Methods, vol. 13, No. 12, pp. 1029-1035, Dec. 2016.
Komor, A.C. et al. "Programmable Editing of a Target Base in Genomic DNA without Double-Stranded DNA Cleavage" Nature, vol. 533, No. 7603, pp. 420-424, May 19, 2016.
International Search Report in International Application No. PCT/CN2018/096810 mailed Oct. 26, 2018.

* cited by examiner

*Primary Examiner* — Nancy J Leith
(74) *Attorney, Agent, or Firm* — NKL Law; Bin Lu; Allen Xue

(57) ABSTRACT

Provided is a method for modulating RNA splicing by inducing a base mutation at a splice site or a base substitution in a polypyrimidine region. The method comprises expressing a targeting cytosine deaminase in a cell, to induce AG at a 3' splice site of an intron of interest in a gene of interest to mutate into AA, or to induce GT at a 5' splice site of the intron of interest in a gene of interest to mutate to AT, or to induce a plurality of Cs in a polypyrimidine region of the intron of interest in a gene of interest to respectively mutate into Ts. The method specifically blocks an exon recognition process, modulates a selective splicing process of endogenous mRNA, induces exon skipping, activates an alternative splice site, induces mutually exclusive exon conversion, induces intron retention, and enhances an exon.

14 Claims, 16 Drawing Sheets

Specification includes a Sequence Listing.

SEQUENCE LISTING

<160> NUMBER OF SEQ ID NOS: 78

<210> SEQ ID NO 1
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: The target binding region of sgRNA CD45-E5-5'SS

<400> SEQUENCE: 1
cctgagatag cattgctgcc 20

<210> SEQ ID NO 2
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: The target binding region of sgRNA CD45-E5-3'SS

<400> SEQUENCE: 2
aacacctaag gtaggaaagt 20

<210> SEQ ID NO 3
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: The target binding region of sgRNA
STAT3-E23-3'SS

<400> SEQUENCE: 3
gtcgttctgt aggaaatggg 20

<210> SEQ ID NO 4
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: The target binding region of sgRNA GANAB-E6-PPT

<400> SEQUENCE: 4
ctgccccagt ttctcggata 20

<210> SEQ ID NO 5
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: The target binding region of sgRNA BAP1-E2-5'SS

<400> SEQUENCE: 5
taccgaaatc ttccacgagc 20

<210> SEQ ID NO 6
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: The sequence of sgRNA BAP1-E3-3'SS

<400> SEQUENCE: 6
cacctgcgat gaggaaagga 20

<210> SEQ ID NO 7
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: The sequence of sgRNA TP53-E8-5' SS

<400> SEQUENCE: 7
cctcgcttag tgctccctgg 20

<210> SEQ ID NO 8
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: The target binding region of sgRNA TP53-E9-3'SS

<400> SEQUENCE: 8
gctaggaaag aggcaaggaa 20

<210> SEQ ID NO 9
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: The target binding region of sgRNA
RPS24-E5-5'SS

<400> SEQUENCE: 9
tatacctgtg atccaatctc 20

<210> SEQ ID NO 10
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: The target binding region of sgRNA RPS24-E5-PPT

<400> SEQUENCE: 10
tgattcagtg agctggagat 20

<210> SEQ ID NO 11
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: The target binding region of sgRNA OS9-E13-PPT

<400> SEQUENCE: 11
cccctctaag aggaggatcc 20

<210> SEQ ID NO 12
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: The target binding region of sgRNA THYN1-E6-PPT

<400> SEQUENCE: 12
gtacactgtt gtcacatagg 20

<210> SEQ ID NO 13
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: The target binding region of sgRNA PKM-3'SS-E9

<400> SEQUENCE: 13
ctatctgtaa ggtttagggt 20

<210> SEQ ID NO 14
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: The target binding region of sgRNA PKM-5'SS-E9

<400> SEQUENCE: 14
ccctacctgc cagactccgt 20

<210> SEQ ID NO 15

```
<211> LENGTH: 23
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: The target binding region of sgRNA PKM-3'
      SS-E10

<400> SEQUENCE: 15

ctaggggagc aacatccgtc cag                                              23


<210> SEQ ID NO 16
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: The target binding region of sgRNA PKM-5'SS-E10

<400> SEQUENCE: 16

tcctacctgc cagacttggt                                                  20


<210> SEQ ID NO 17
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: The target binding region of sgRNA DMD EXON50
      5'SS

<400> SEQUENCE: 17

atacttacag gctccaatag                                                  20


<210> SEQ ID NO 18
<211> LENGTH: 33
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Primer

<400> SEQUENCE: 18

aaactcgagt gtacaaaaaa gcaggcttta aag                                   33


<210> SEQ ID NO 19
<211> LENGTH: 37
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Primer
<220> FEATURE:
<221> NAME/KEY: misc_feature
<222> LOCATION: (2)..(20)
<223> OTHER INFORMATION: n is a, c, g or t

<400> SEQUENCE: 19

gnnnnnnnnn nnnnnnnnnn ggtgtttcgt cctttcc                               37
```

<210> SEQ ID NO 20
<211> LENGTH: 42
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Primer
<220> FEATURE:
<221> NAME/KEY: misc_feature
<222> LOCATION: (2)..(20)
<223> OTHER INFORMATION: n is a, c, g or t

<400> SEQUENCE: 20
gnnnnnnnnn nnnnnnnnnn gttttagagc tagaaatagc aa 42

<210> SEQ ID NO 21
<211> LENGTH: 36
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Primer

<400> SEQUENCE: 21
aaagctagct aatgccaact ttgtacaaga aagctg 36

<210> SEQ ID NO 22
<211> LENGTH: 5013
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Coding sequence of AIDX-XTEN-nCAS9

<400> SEQUENCE: 22
atggacagcc tcttgatgaa ccggaggaag tttctttacc aattcaaaaa tgtccgctgg 60
gctaagggtc ggcgtgagac ctacctgtgc tacgtagtga agaggcgtga cagtgctaca 120
tccttttcac tggactttgg ttatcttcgc aataagaacg gctgccacgt ggaattgctc 180
ttcctccgct acatctcgga ctgggaccta gaccctggcc gctgctaccg cgtcacctgg 240
ttcacctcct ggagcccctg ctacgactgt gcccgacatg tggccgactt tctgcgaggg 300
aaccccaacc tcagtctgag gatcttcacc gcgcgcctct acttctgtga ggaccgcaag 360
gctgagcccg aggggctgcg gcggctgcac cgcgccgggg tgcaaatagc catcatgacc 420
ttcaaagatt atttttactg ctggaatact tttgtagaaa accatgaaag aactttcaaa 480
gcctgggaag ggctgcatga aaattcagtt cgtctctcca gacagcttcg gcgcatcctt 540
ttgcccagcg gcagcgagac tcccgggacc tcagagtccg ccacacccga aagtatggat 600
aagaaatact caataggctt agctatcggc acaaatagcg tcggatgggc ggtgatcact 660
gatgaatata aggttccgtc taaaaagttc aaggttctgg gaaatacaga ccgccacagt 720
atcaaaaaaa atcttatagg ggctctttta tttgacagtg gagagacagc ggaagcgact 780
cgtctcaaac ggacagctcg tagaaggtat acacgtcgga agaatcgtat ttgttatcta 840
caggagattt tttcaaatga gatggcgaaa gtagatgata gtttctttca tcgacttgaa 900
gagtcttttt tggtggaaga agacaagaag catgaacgtc atcctatttt tggaaatata 960

```
gtagatgaag ttgcttatca tgagaaatat ccaactatct atcatctgcg aaaaaaattg   1020
gtagattcta ctgataaagc ggatttgcgc ttaatctatt tggccttagc gcatatgatt   1080
aagtttcgtg gtcatttttt gattgaggga gatttaaatc ctgataatag tgatgtggac   1140
aaactattta tccagttggt acaaacctac aatcaattat ttgaagaaaa ccctattaac   1200
gcaagtggag tagatgctaa agcgattctt tctgcacgat tgagtaaatc aagacgatta   1260
gaaaatctca ttgctcagct ccccggtgag aagaaaaatg gcttatttgg gaatctcatt   1320
gctttgtcat tgggtttgac ccctaatttt aaatcaaatt ttgatttggc agaagatgct   1380
aaattacagc tttcaaaaga tacttacgat gatgatttag ataatttatt ggcgcaaatt   1440
ggagatcaat atgctgattt gtttttggca gctaagaatt tatcagatgc tattttactt   1500
tcagatatcc taagagtaaa tactgaaata actaaggctc ccctatcagc ttcaatgatt   1560
aaacgctacg atgaacatca tcaagacttg actcttttaa aagctttagt tcgacaacaa   1620
cttccagaaa agtataaaga aatctttttt gatcaatcaa aaaacggata tgcaggttat   1680
attgatgggg gagctagcca agaagaattt tataaattta tcaaaccaat tttagaaaaa   1740
atggatggta ctgaggaatt attggtgaaa ctaaatcgtg aagatttgct gcgcaagcaa   1800
cggacctttg acaacggctc tattccccat caaattcact tgggtgagct gcatgctatt   1860
ttgagaagac aagaagactt ttatccattt ttaaaagaca atcgtgagaa gattgaaaaa   1920
atcttgactt ttcgaattcc ttattatgtt ggtccattgg cgcgtggcaa tagtcgtttt   1980
gcatggatga ctcggaagtc tgaagaaaca attacccat ggaattttga agaagttgtc   2040
gataaaggtg cttcagctca atcatttatt gaacgcatga caaactttga taaaaatctt   2100
ccaaatgaaa aagtactacc aaaacatagt ttgctttatg agtattttac ggtttataac   2160
gaattgacaa aggtcaaata tgttactgaa ggaatgcgaa aaccagcatt tctttcaggt   2220
gaacagaaga aagccattgt tgatttactc ttcaaaacaa atcgaaaagt aaccgttaag   2280
caattaaaag aagattattt caaaaaaata gaatgttttg atagtgttga aatttcagga   2340
gttgaagata gatttaatgc ttcattaggt acctaccatg atttgctaaa aattattaaa   2400
gataaagatt ttttggataa tgaagaaaat gaagatatct tagaggatat tgttttaaca   2460
ttgaccttat ttgaagatag ggagatgatt gaggaaagac ttaaaacata tgctcacctc   2520
tttgatgata aggtgatgaa acagcttaaa cgtcgccgtt atactggttg gggacgtttg   2580
tctcgaaaat tgattaatgg tattagggat aagcaatctg gcaaaacaat attagatttt   2640
ttgaaatcag atggttttgc caatcgcaat tttatgcagc tgatccatga tgatagtttg   2700
acatttaaag aagacattca aaaagcacaa gtgtctggac aaggcgatag tttacatgaa   2760
catattgcaa atttagctgg tagccctgct attaaaaaag gtattttaca gactgtaaaa   2820
gttgttgatg aattggtcaa agtaatgggg cggcataagc cagaaaatat cgttattgaa   2880
atggcacgtg aaaatcagac aactcaaaag ggccagaaaa attcgcgaga gcgtatgaaa   2940
cgaatcgaag aaggtatcaa agaattagga agtcagattc ttaaagagca tcctgttgaa   3000
aatactcaat tgcaaaatga aaagctctat ctctattatc tccaaaatgg aagagacatg   3060
tatgtggacc aagaattaga tattaatcgt ttaagtgatt atgatgtcga tcacattgtt   3120
ccacaaagtt tccttaaaga cgattcaata gacaataagg tcttaacgcg ttctgataaa   3180
aatcgtggta aatcggataa cgttccaagt gaagaagtag tcaaaaagat gaaaaactat   3240
tggagacaac ttctaaacgc caagttaatc actcaacgta agtttgataa tttaacgaaa   3300
gctgaacgtg gaggtttgag tgaacttgat aaagctggtt ttatcaaacg ccaattggtt   3360
```

```
gaaactcgcc aaatcactaa gcatgtggca caaattttgg atagtcgcat gaatactaaa   3420
tacgatgaaa atgataaact tattcgagag gttaaagtga ttaccttaaa atctaaatta   3480
gtttctgact tccgaaaaga tttccaattc tataaagtac gtgagattaa caattaccat   3540
catgcccatg atgcgtatct aaatgccgtc gttggaactg ctttgattaa gaaatatcca   3600
aaacttgaat cggagtttgt ctatggtgat tataaagttt atgatgttcg taaaatgatt   3660
gctaagtctg agcaagaaat aggcaaagca accgcaaaat atttctttta ctctaatatc   3720
atgaacttct tcaaaacaga aattacactt gcaaatggag agattcgcaa acgccctcta   3780
atcgaaacta atggggaaac tggagaaatt gtctgggata aagggcgaga ttttgccaca   3840
gtgcgcaaag tattgtccat gccccaagtc aatattgtca agaaaacaga agtacagaca   3900
ggcggattct ccaaggagtc aattttacca aaaagaaatt cggacaagct tattgctcgt   3960
aaaaaagact gggatccaaa aaaatatggt ggttttgata gtccaacggt agcttattca   4020
gtcctagtgg ttgctaaggt ggaaaaaggg aaatcgaaga agttaaaatc cgttaaagag   4080
ttactaggga tcacaattat ggaaagaagt tcctttgaaa aaaatccgat tgacttttta   4140
gaagctaaag gatataagga agttaaaaaa gacttaatca ttaaactacc taaatatagt   4200
ctttttgagt tagaaaacgg tcgtaaacgg atgctggcta gtgccggaga attacaaaaa   4260
ggaaatgagc tggctctgcc aagcaaatat gtgaattttt tatatttagc tagtcattat   4320
gaaaagttga agggtagtcc agaagataac gaacaaaaac aattgtttgt tgagcagcat   4380
aagcattatt tagatgagat tattgagcaa atcagtgaat tttctaagcg tgttatttta   4440
gcagatgcca atttagataa agttcttagt gcatataaca aacatagaga caaaccaata   4500
cgtgaacaag cagaaaatat tattcattta tttacgttga cgaatcttgg agctcccgct   4560
gcttttaaat attttgatac aacaattgat cgtaaacgat atacgtctac aaaagaagtt   4620
ttagatgcca ctcttatcca tcaatccatc actggtcttt atgaaacacg cattgatttg   4680
agtcagctag gaggtgactc tggtggttct actaatctgt cagatattat tgaaaaggag   4740
accggtaagc aactggttat ccaggaatcc atcctcatgc tcccagagga ggtggaagaa   4800
gtcattggga acaagccgga aagcgatata ctcgtgcaca ccgcctacga cgagagcacc   4860
gacgagaatg tcatgcttct gactagcgac gcccctgaat acaagccttg ggctctggtc   4920
atacaggata gcaacggtga gaacaagatt aagatgctct ctggtggttc tcccaagaag   4980
aagaggaaag tccatcacca ccaccatcac taa                                5013
```

<210> SEQ ID NO 23
<211> LENGTH: 1670
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Amino acid sequence of AIDX-XTEN-nCAS9

<400> SEQUENCE: 23

```
Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45
```

```
Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Ser Gly Ser Glu Thr Pro Gly Thr Ser Glu
            180                 185                 190

Ser Ala Thr Pro Glu Ser Met Asp Lys Lys Tyr Ser Ile Gly Leu Ala
        195                 200                 205

Ile Gly Thr Asn Ser Val Gly Trp Ala Val Ile Thr Asp Glu Tyr Lys
    210                 215                 220

Val Pro Ser Lys Lys Phe Lys Val Leu Gly Asn Thr Asp Arg His Ser
225                 230                 235                 240

Ile Lys Lys Asn Leu Ile Gly Ala Leu Leu Phe Asp Ser Gly Glu Thr
                245                 250                 255

Ala Glu Ala Thr Arg Leu Lys Arg Thr Ala Arg Arg Arg Tyr Thr Arg
            260                 265                 270

Arg Lys Asn Arg Ile Cys Tyr Leu Gln Glu Ile Phe Ser Asn Glu Met
        275                 280                 285

Ala Lys Val Asp Asp Ser Phe Phe His Arg Leu Glu Glu Ser Phe Leu
    290                 295                 300

Val Glu Glu Asp Lys Lys His Glu Arg His Pro Ile Phe Gly Asn Ile
305                 310                 315                 320

Val Asp Glu Val Ala Tyr His Glu Lys Tyr Pro Thr Ile Tyr His Leu
                325                 330                 335

Arg Lys Lys Leu Val Asp Ser Thr Asp Lys Ala Asp Leu Arg Leu Ile
            340                 345                 350

Tyr Leu Ala Leu Ala His Met Ile Lys Phe Arg Gly His Phe Leu Ile
        355                 360                 365

Glu Gly Asp Leu Asn Pro Asp Asn Ser Asp Val Asp Lys Leu Phe Ile
    370                 375                 380

Gln Leu Val Gln Thr Tyr Asn Gln Leu Phe Glu Glu Asn Pro Ile Asn
385                 390                 395                 400

Ala Ser Gly Val Asp Ala Lys Ala Ile Leu Ser Ala Arg Leu Ser Lys
                405                 410                 415

Ser Arg Arg Leu Glu Asn Leu Ile Ala Gln Leu Pro Gly Glu Lys Lys
            420                 425                 430

Asn Gly Leu Phe Gly Asn Leu Ile Ala Leu Ser Leu Gly Leu Thr Pro
        435                 440                 445

Asn Phe Lys Ser Asn Phe Asp Leu Ala Glu Asp Ala Lys Leu Gln Leu
    450                 455                 460

Ser Lys Asp Thr Tyr Asp Asp Asp Leu Asp Asn Leu Leu Ala Gln Ile
```

```
465                 470                 475                 480

Gly Asp Gln Tyr Ala Asp Leu Phe Leu Ala Ala Lys Asn Leu Ser Asp
                485                 490                 495

Ala Ile Leu Leu Ser Asp Ile Leu Arg Val Asn Thr Glu Ile Thr Lys
            500                 505                 510

Ala Pro Leu Ser Ala Ser Met Ile Lys Arg Tyr Asp Glu His His Gln
        515                 520                 525

Asp Leu Thr Leu Leu Lys Ala Leu Val Arg Gln Gln Leu Pro Glu Lys
    530                 535                 540

Tyr Lys Glu Ile Phe Phe Asp Gln Ser Lys Asn Gly Tyr Ala Gly Tyr
545                 550                 555                 560

Ile Asp Gly Gly Ala Ser Gln Glu Glu Phe Tyr Lys Phe Ile Lys Pro
                565                 570                 575

Ile Leu Glu Lys Met Asp Gly Thr Glu Glu Leu Leu Val Lys Leu Asn
            580                 585                 590

Arg Glu Asp Leu Leu Arg Lys Gln Arg Thr Phe Asp Asn Gly Ser Ile
        595                 600                 605

Pro His Gln Ile His Leu Gly Glu Leu His Ala Ile Leu Arg Arg Gln
    610                 615                 620

Glu Asp Phe Tyr Pro Phe Leu Lys Asp Asn Arg Glu Lys Ile Glu Lys
625                 630                 635                 640

Ile Leu Thr Phe Arg Ile Pro Tyr Tyr Val Gly Pro Leu Ala Arg Gly
                645                 650                 655

Asn Ser Arg Phe Ala Trp Met Thr Arg Lys Ser Glu Glu Thr Ile Thr
            660                 665                 670

Pro Trp Asn Phe Glu Glu Val Val Asp Lys Gly Ala Ser Ala Gln Ser
        675                 680                 685

Phe Ile Glu Arg Met Thr Asn Phe Asp Lys Asn Leu Pro Asn Glu Lys
    690                 695                 700

Val Leu Pro Lys His Ser Leu Leu Tyr Glu Tyr Phe Thr Val Tyr Asn
705                 710                 715                 720

Glu Leu Thr Lys Val Lys Tyr Val Thr Glu Gly Met Arg Lys Pro Ala
                725                 730                 735

Phe Leu Ser Gly Glu Gln Lys Lys Ala Ile Val Asp Leu Leu Phe Lys
            740                 745                 750

Thr Asn Arg Lys Val Thr Val Lys Gln Leu Lys Glu Asp Tyr Phe Lys
        755                 760                 765

Lys Ile Glu Cys Phe Asp Ser Val Glu Ile Ser Gly Val Glu Asp Arg
    770                 775                 780

Phe Asn Ala Ser Leu Gly Thr Tyr His Asp Leu Leu Lys Ile Ile Lys
785                 790                 795                 800

Asp Lys Asp Phe Leu Asp Asn Glu Glu Asn Glu Asp Ile Leu Glu Asp
                805                 810                 815

Ile Val Leu Thr Leu Thr Leu Phe Glu Asp Arg Glu Met Ile Glu Glu
            820                 825                 830

Arg Leu Lys Thr Tyr Ala His Leu Phe Asp Asp Lys Val Met Lys Gln
        835                 840                 845

Leu Lys Arg Arg Arg Tyr Thr Gly Trp Gly Arg Leu Ser Arg Lys Leu
    850                 855                 860

Ile Asn Gly Ile Arg Asp Lys Gln Ser Gly Lys Thr Ile Leu Asp Phe
865                 870                 875                 880

Leu Lys Ser Asp Gly Phe Ala Asn Arg Asn Phe Met Gln Leu Ile His
                885                 890                 895
```

-continued

Asp Asp Ser Leu Thr Phe Lys Glu Asp Ile Gln Lys Ala Gln Val Ser
900 905 910

Gly Gln Gly Asp Ser Leu His Glu His Ile Ala Asn Leu Ala Gly Ser
915 920 925

Pro Ala Ile Lys Lys Gly Ile Leu Gln Thr Val Lys Val Val Asp Glu
930 935 940

Leu Val Lys Val Met Gly Arg His Lys Pro Glu Asn Ile Val Ile Glu
945 950 955 960

Met Ala Arg Glu Asn Gln Thr Thr Gln Lys Gly Gln Lys Asn Ser Arg
965 970 975

Glu Arg Met Lys Arg Ile Glu Glu Gly Ile Lys Glu Leu Gly Ser Gln
980 985 990

Ile Leu Lys Glu His Pro Val Glu Asn Thr Gln Leu Gln Asn Glu Lys
995 1000 1005

Leu Tyr Leu Tyr Tyr Leu Gln Asn Gly Arg Asp Met Tyr Val Asp
1010 1015 1020

Gln Glu Leu Asp Ile Asn Arg Leu Ser Asp Tyr Asp Val Asp His
1025 1030 1035

Ile Val Pro Gln Ser Phe Leu Lys Asp Asp Ser Ile Asp Asn Lys
1040 1045 1050

Val Leu Thr Arg Ser Asp Lys Asn Arg Gly Lys Ser Asp Asn Val
1055 1060 1065

Pro Ser Glu Glu Val Val Lys Lys Met Lys Asn Tyr Trp Arg Gln
1070 1075 1080

Leu Leu Asn Ala Lys Leu Ile Thr Gln Arg Lys Phe Asp Asn Leu
1085 1090 1095

Thr Lys Ala Glu Arg Gly Gly Leu Ser Glu Leu Asp Lys Ala Gly
1100 1105 1110

Phe Ile Lys Arg Gln Leu Val Glu Thr Arg Gln Ile Thr Lys His
1115 1120 1125

Val Ala Gln Ile Leu Asp Ser Arg Met Asn Thr Lys Tyr Asp Glu
1130 1135 1140

Asn Asp Lys Leu Ile Arg Glu Val Lys Val Ile Thr Leu Lys Ser
1145 1150 1155

Lys Leu Val Ser Asp Phe Arg Lys Asp Phe Gln Phe Tyr Lys Val
1160 1165 1170

Arg Glu Ile Asn Asn Tyr His His Ala His Asp Ala Tyr Leu Asn
1175 1180 1185

Ala Val Val Gly Thr Ala Leu Ile Lys Lys Tyr Pro Lys Leu Glu
1190 1195 1200

Ser Glu Phe Val Tyr Gly Asp Tyr Lys Val Tyr Asp Val Arg Lys
1205 1210 1215

Met Ile Ala Lys Ser Glu Gln Glu Ile Gly Lys Ala Thr Ala Lys
1220 1225 1230

Tyr Phe Phe Tyr Ser Asn Ile Met Asn Phe Phe Lys Thr Glu Ile
1235 1240 1245

Thr Leu Ala Asn Gly Glu Ile Arg Lys Arg Pro Leu Ile Glu Thr
1250 1255 1260

Asn Gly Glu Thr Gly Glu Ile Val Trp Asp Lys Gly Arg Asp Phe
1265 1270 1275

Ala Thr Val Arg Lys Val Leu Ser Met Pro Gln Val Asn Ile Val
1280 1285 1290

-continued

```
Lys Lys  Thr Glu Val Gln Thr  Gly Gly Phe Ser Lys  Glu Ser Ile
    1295                 1300                 1305

Leu Pro  Lys Arg Asn Ser Asp  Lys Leu Ile Ala Arg  Lys Lys Asp
    1310                 1315                 1320

Trp Asp  Pro Lys Lys Tyr Gly  Gly Phe Asp Ser Pro  Thr Val Ala
    1325                 1330                 1335

Tyr Ser  Val Leu Val Val Ala  Lys Val Glu Lys Gly  Lys Ser Lys
    1340                 1345                 1350

Lys Leu  Lys Ser Val Lys Glu  Leu Leu Gly Ile Thr  Ile Met Glu
    1355                 1360                 1365

Arg Ser  Ser Phe Glu Lys Asn  Pro Ile Asp Phe Leu  Glu Ala Lys
    1370                 1375                 1380

Gly Tyr  Lys Glu Val Lys Lys  Asp Leu Ile Ile Lys  Leu Pro Lys
    1385                 1390                 1395

Tyr Ser  Leu Phe Glu Leu Glu  Asn Gly Arg Lys Arg  Met Leu Ala
    1400                 1405                 1410

Ser Ala  Gly Glu Leu Gln Lys  Gly Asn Glu Leu Ala  Leu Pro Ser
    1415                 1420                 1425

Lys Tyr  Val Asn Phe Leu Tyr  Leu Ala Ser His Tyr  Glu Lys Leu
    1430                 1435                 1440

Lys Gly  Ser Pro Glu Asp Asn  Glu Gln Lys Gln Leu  Phe Val Glu
    1445                 1450                 1455

Gln His  Lys His Tyr Leu Asp  Glu Ile Ile Glu Gln  Ile Ser Glu
    1460                 1465                 1470

Phe Ser  Lys Arg Val Ile Leu  Ala Asp Ala Asn Leu  Asp Lys Val
    1475                 1480                 1485

Leu Ser  Ala Tyr Asn Lys His  Arg Asp Lys Pro Ile  Arg Glu Gln
    1490                 1495                 1500

Ala Glu  Asn Ile Ile His Leu  Phe Thr Leu Thr Asn  Leu Gly Ala
    1505                 1510                 1515

Pro Ala  Ala Phe Lys Tyr Phe  Asp Thr Thr Ile Asp  Arg Lys Arg
    1520                 1525                 1530

Tyr Thr  Ser Thr Lys Glu Val  Leu Asp Ala Thr Leu  Ile His Gln
    1535                 1540                 1545

Ser Ile  Thr Gly Leu Tyr Glu  Thr Arg Ile Asp Leu  Ser Gln Leu
    1550                 1555                 1560

Gly Gly  Asp Ser Gly Gly Ser  Thr Asn Leu Ser Asp  Ile Ile Glu
    1565                 1570                 1575

Lys Glu  Thr Gly Lys Gln Leu  Val Ile Gln Glu Ser  Ile Leu Met
    1580                 1585                 1590

Leu Pro  Glu Glu Val Glu Glu  Val Ile Gly Asn Lys  Pro Glu Ser
    1595                 1600                 1605

Asp Ile  Leu Val His Thr Ala  Tyr Asp Glu Ser Thr  Asp Glu Asn
    1610                 1615                 1620

Val Met  Leu Leu Thr Ser Asp  Ala Pro Glu Tyr Lys  Pro Trp Ala
    1625                 1630                 1635

Leu Val  Ile Gln Asp Ser Asn  Gly Glu Asn Lys Ile  Lys Met Leu
    1640                 1645                 1650

Ser Gly  Gly Ser Pro Lys Lys  Lys Arg Lys Val His  His His His
    1655                 1660                 1665

His His
    1670
```

<210> SEQ ID NO 24
<211> LENGTH: 4989
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Coding sequence of dcas9-AID

<400> SEQUENCE: 24
atggactata aggaccacga cggagactac aaggatcatg atattgatta caaagacgat 60
gacgataaga tggccccaaa gaagaagcgg aaggtcggta tccacggagt cccagcagct 120
accatggaca agaagtattc tatcggactg gccatcggga ctaatagcgt cgggtgggcc 180
gtgatcactg acgagtacaa ggtgccctct aagaagttca aggtgctcgg gaacaccgac 240
cggcattcca tcaagaaaaa tctgatcgga gctctcctct ttgattcagg ggagaccgct 300
gaagcaaccc gcctcaagcg gactgctaga cggcggtaca ccaggaggaa gaaccggatt 360
tgttaccttc aagagatatt ctccaacgaa atggcaaagg tcgacgacag cttcttccat 420
aggctggaag aatcattcct cgtggaagag gataagaagc atgaacggca tcccatcttc 480
ggtaatatcg tcgacgaggt ggcctatcac gagaaatacc caaccatcta ccatcttcgc 540
aaaaagctgg tggactcaac cgacaaggca gacctccggc ttatctacct ggccctggcc 600
cacatgatca agttcagagg ccacttcctg atcgagggcg acctcaatcc tgacaatagc 660
gatgtggata aactgttcat ccagctggtg cagacttaca accagctctt tgaagagaac 720
cccatcaatg caagcggagt cgatgccaag gccattctgt cagcccggct gtcaaagagc 780
cgcagacttg agaatcttat cgctcagctg ccgggtgaaa agaaaaatgg actgttcggg 840
aacctgattg ctctttcact tgggctgact cccaatttca agtctaattt cgacctggca 900
gaggatgcca agctgcaact gtccaaggac acctatgatg acgatctcga caacctcctg 960
gcccagatcg gtgaccaata cgccgacctt ttccttgctg ctaagaatct ttctgacgcc 1020
atcctgctgt ctgacattct ccgcgtgaac actgaaatca ccaaggcccc tctttcagct 1080
tcaatgatta agcggtatga tgagcaccac caggacctga ccctgcttaa ggcactcgtc 1140
cggcagcagc ttccggagaa gtacaaggaa atcttctttg accagtcaaa gaatggatac 1200
gccggctaca tcgacggagg tgcctcccaa gaggaatttt ataagtttat caaacctatc 1260
cttgagaaga tggacggcac cgaagagctc ctcgtgaaac tgaatcggga ggatctgctg 1320
cggaagcagc gcactttcga caatgggagc attccccacc agatccatct tggggagctt 1380
cacgccatcc ttcggcgcca agaggacttc taccccttc ttaaggacaa cagggagaag 1440
attgagaaaa ttctcacttt ccgcatcccc tactacgtgg gacccctcgc cagaggaaat 1500
agccggtttg cttggatgac cagaaagtca gaagaaacta tcactccctg gaacttcgaa 1560
gaggtggtgg acaagggagc cagcgctcag tcattcatcg aacggatgac taacttcgat 1620
aagaacctcc ccaatgagaa ggtcctgccg aaacattccc tgctctacga gtactttacc 1680
gtgtacaacg agctgaccaa ggtgaaatat gtcaccgaag ggatgaggaa gcccgcattc 1740
ctgtcaggcg aacaaaagaa ggcaattgtg gaccttctgt tcaagaccaa tagaaaggtg 1800
accgtgaagc agctgaagga ggactatttc aagaaaattg aatgcttcga ctctgtggag 1860
attagcgggg tcgaagatcg gttcaacgca agcctgggta cctaccatga tctgcttaag 1920
atcatcaagg acaaggattt tctggacaat gaggagaacg aggacatcct tgaggacatt 1980
gtcctgactc tcactctgtt cgaggaccgg gaaatgatcg aggagaggct taagacctac 2040

```
gcccatctgt tcgacgataa agtgatgaag caacttaaac ggagaagata taccggatgg   2100
ggacgcctta gccgcaaact catcaacgga atccgggaca aacagagcgg aaagaccatt   2160
cttgatttcc ttaagagcga cggattcgct aatcgcaact tcatgcaact tatccatgat   2220
gattccctga cctttaagga ggacatccag aaggcccaag tgtctggaca aggtgactca   2280
ctgcacgagc atatcgcaaa tctggctggt tcacccgcta ttaagaaggg tattctccag   2340
accgtgaaag tcgtggacga gctggtcaag gtgatgggtc gccataaacc agagaacatt   2400
gtcatcgaga tggccaggga aaaccagact acccagaagg gacagaagaa cagcagggag   2460
cggatgaaaa gaattgagga agggattaag gagctcgggt cacagatcct taaagagcac   2520
ccggtggaaa acacccagct tcagaatgag aagctctatc tgtactacct tcaaaatgga   2580
cgcgatatgt atgtggacca agagcttgat atcaacaggc tctcagacta cgacgtggac   2640
gccatcgtcc ctcagagctt cctcaaagac gactcaattg acaataaggt gctgactcgc   2700
tcagacaaga accggggaaa gtcagataac gtgccctcag aggaagtcgt gaaaaagatg   2760
aagaactatt ggcgccagct tctgaacgca aagctgatca ctcagcggaa gttcgacaat   2820
ctcactaagg ctgagagggg cggactgagc gaactggaca aagcaggatt cattaaacgg   2880
caacttgtgg agactcggca gattactaaa catgtcgccc aaatccttga ctcacgcatg   2940
aataccaagt acgacgaaaa cgacaaactt atccgcgagg tgaaggtgat taccctgaag   3000
tccaagctgg tcagcgattt cagaaaggac tttcaattct acaaagtgcg ggagatcaat   3060
aactatcatc atgctcatga cgcatatctg aatgccgtgg tgggaaccgc cctgatcaag   3120
aagtacccaa agctggaaag cgagttcgtg tacggagact acaaggtcta cgacgtgcgc   3180
aagatgattg ccaaatctga gcaggagatc ggaaaggcca ccgcaaagta cttcttctac   3240
agcaacatca tgaatttctt caagaccgaa atcacccttg caaacggtga gatccggaag   3300
aggccgctca tcgagactaa tggggagact ggcgaaatcg tgtgggacaa gggcagagat   3360
ttcgctaccg tgcgcaaagt gctttctatg cctcaagtga acatcgtgaa gaaaaccgag   3420
gtgcaaaccg gaggcttttc taaggaatca atcctcccca agcgcaactc cgacaagctc   3480
attgcaagga agaaggattg ggaccctaag aagtacggcg gattcgattc accaactgtg   3540
gcttattctg tcctggtcgt ggctaaggtg gaaaaaggaa agtctaagaa gctcaagagc   3600
gtgaaggaac tgctgggtat caccattatg gagcgcagct ccttcgagaa gaacccaatt   3660
gactttctcg aagccaaagg ttacaaggaa gtcaagaagg accttatcat caagctccca   3720
aagtatagcc tgttcgaact ggagaatggg cggaagcgga tgctcgcctc cgctggcgaa   3780
cttcagaagg gtaatgagct ggctctcccc tccaagtacg tgaatttcct ctaccttgca   3840
agccattacg agaagctgaa ggggagcccc gaggacaacg agcaaaagca actgtttgtg   3900
gagcagcata agcattatct ggacgagatc attgagcaga tttccgagtt ttctaaacgc   3960
gtcattctcg ctgatgccaa cctcgataaa gtccttagcg catacaataa gcacagagac   4020
aaaccaattc gggagcaggc tgagaatatc atccacctgt tcaccctcac caatcttggt   4080
gccccctgccg cattcaagta cttcgacacc accatcgacc ggaaacgcta tacctccacc   4140
aaagaagtgc tggacgccac cctcatccac cagagcatca ccggacttta cgaaactcgg   4200
attgacctct cacagctcgg aggggatgag ggagctccca agaaaaagcg caaggtaggt   4260
agttccggat ctccgaaaaa gaaacgcaaa gttggtagtg atgctttaga cgattttgac   4320
ttagatatgc ttggttcaga cgcgttagac gacttcggtg gaggatccat ggacagcctc   4380
```

```
ttgatgaacc ggaggaagtt tctttaccaa ttcaaaaatg tccgctgggc taagggtcgg   4440

cgtgagacct acctgtgcta cgtagtgaag aggcgtgaca gtgctacatc cttttcactg   4500

gactttggtt atcttcgcaa taagaacggc tgccacgtgg aattgctctt cctccgctac   4560

atctcggact gggacctaga ccctggccgc tgctaccgcg tcacctggtt cacctcctgg   4620

agcccctgct acgactgtgc ccgacatgtg gccgactttc tgcgagggaa ccccaacctc   4680

agtctgagga tcttcaccgc gcgcctctac ttctgtgagg accgcaaggc tgagcccgag   4740

gggctgcggc ggctgcaccg cgccggggtg caaatagcca tcatgacctt caaagattat   4800

ttttactgct ggaatacttt tgtagaaaac catgaaagaa ctttcaaagc ctgggaaggg   4860

ctgcatgaaa attcagttcg tctctccaga cagcttcggc gcatcctttt gcccctgtat   4920

gaggttgatg acttacgaga cgcatttcgt acttggggac gtgattacaa agacgatgac   4980

gataagtga                                                           4989
```

```
<210> SEQ ID NO 25
<211> LENGTH: 1662
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Amino acid sequence of dcas9-AID

<400> SEQUENCE: 25

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Ile His Gly Val Pro Ala Ala Thr Met Asp Lys Lys Tyr Ser Ile
        35                  40                  45

Gly Leu Ala Ile Gly Thr Asn Ser Val Gly Trp Ala Val Ile Thr Asp
    50                  55                  60

Glu Tyr Lys Val Pro Ser Lys Lys Phe Lys Val Leu Gly Asn Thr Asp
65                  70                  75                  80

Arg His Ser Ile Lys Lys Asn Leu Ile Gly Ala Leu Leu Phe Asp Ser
                85                  90                  95

Gly Glu Thr Ala Glu Ala Thr Arg Leu Lys Arg Thr Ala Arg Arg Arg
            100                 105                 110

Tyr Thr Arg Arg Lys Asn Arg Ile Cys Tyr Leu Gln Glu Ile Phe Ser
        115                 120                 125

Asn Glu Met Ala Lys Val Asp Asp Ser Phe Phe His Arg Leu Glu Glu
    130                 135                 140

Ser Phe Leu Val Glu Glu Asp Lys Lys His Glu Arg His Pro Ile Phe
145                 150                 155                 160

Gly Asn Ile Val Asp Glu Val Ala Tyr His Glu Lys Tyr Pro Thr Ile
                165                 170                 175

Tyr His Leu Arg Lys Lys Leu Val Asp Ser Thr Asp Lys Ala Asp Leu
            180                 185                 190

Arg Leu Ile Tyr Leu Ala Leu Ala His Met Ile Lys Phe Arg Gly His
        195                 200                 205

Phe Leu Ile Glu Gly Asp Leu Asn Pro Asp Asn Ser Asp Val Asp Lys
    210                 215                 220

Leu Phe Ile Gln Leu Val Gln Thr Tyr Asn Gln Leu Phe Glu Glu Asn
225                 230                 235                 240
```

-continued

Pro Ile Asn Ala Ser Gly Val Asp Ala Lys Ala Ile Leu Ser Ala Arg
245 250 255

Leu Ser Lys Ser Arg Arg Leu Glu Asn Leu Ile Ala Gln Leu Pro Gly
260 265 270

Glu Lys Lys Asn Gly Leu Phe Gly Asn Leu Ile Ala Leu Ser Leu Gly
275 280 285

Leu Thr Pro Asn Phe Lys Ser Asn Phe Asp Leu Ala Glu Asp Ala Lys
290 295 300

Leu Gln Leu Ser Lys Asp Thr Tyr Asp Asp Asp Leu Asp Asn Leu Leu
305 310 315 320

Ala Gln Ile Gly Asp Gln Tyr Ala Asp Leu Phe Leu Ala Ala Lys Asn
325 330 335

Leu Ser Asp Ala Ile Leu Leu Ser Asp Ile Leu Arg Val Asn Thr Glu
340 345 350

Ile Thr Lys Ala Pro Leu Ser Ala Ser Met Ile Lys Arg Tyr Asp Glu
355 360 365

His His Gln Asp Leu Thr Leu Leu Lys Ala Leu Val Arg Gln Gln Leu
370 375 380

Pro Glu Lys Tyr Lys Glu Ile Phe Phe Asp Gln Ser Lys Asn Gly Tyr
385 390 395 400

Ala Gly Tyr Ile Asp Gly Gly Ala Ser Gln Glu Glu Phe Tyr Lys Phe
405 410 415

Ile Lys Pro Ile Leu Glu Lys Met Asp Gly Thr Glu Glu Leu Leu Val
420 425 430

Lys Leu Asn Arg Glu Asp Leu Leu Arg Lys Gln Arg Thr Phe Asp Asn
435 440 445

Gly Ser Ile Pro His Gln Ile His Leu Gly Glu Leu His Ala Ile Leu
450 455 460

Arg Arg Gln Glu Asp Phe Tyr Pro Phe Leu Lys Asp Asn Arg Glu Lys
465 470 475 480

Ile Glu Lys Ile Leu Thr Phe Arg Ile Pro Tyr Tyr Val Gly Pro Leu
485 490 495

Ala Arg Gly Asn Ser Arg Phe Ala Trp Met Thr Arg Lys Ser Glu Glu
500 505 510

Thr Ile Thr Pro Trp Asn Phe Glu Glu Val Val Asp Lys Gly Ala Ser
515 520 525

Ala Gln Ser Phe Ile Glu Arg Met Thr Asn Phe Asp Lys Asn Leu Pro
530 535 540

Asn Glu Lys Val Leu Pro Lys His Ser Leu Leu Tyr Glu Tyr Phe Thr
545 550 555 560

Val Tyr Asn Glu Leu Thr Lys Val Lys Tyr Val Thr Glu Gly Met Arg
565 570 575

Lys Pro Ala Phe Leu Ser Gly Glu Gln Lys Lys Ala Ile Val Asp Leu
580 585 590

Leu Phe Lys Thr Asn Arg Lys Val Thr Val Lys Gln Leu Lys Glu Asp
595 600 605

Tyr Phe Lys Lys Ile Glu Cys Phe Asp Ser Val Glu Ile Ser Gly Val
610 615 620

Glu Asp Arg Phe Asn Ala Ser Leu Gly Thr Tyr His Asp Leu Leu Lys
625 630 635 640

Ile Ile Lys Asp Lys Asp Phe Leu Asp Asn Glu Glu Asn Glu Asp Ile
645 650 655

```
Leu Glu Asp Ile Val Leu Thr Leu Thr Leu Phe Glu Asp Arg Glu Met
            660                 665                 670

Ile Glu Glu Arg Leu Lys Thr Tyr Ala His Leu Phe Asp Asp Lys Val
        675                 680                 685

Met Lys Gln Leu Lys Arg Arg Arg Tyr Thr Gly Trp Gly Arg Leu Ser
    690                 695                 700

Arg Lys Leu Ile Asn Gly Ile Arg Asp Lys Gln Ser Gly Lys Thr Ile
705                 710                 715                 720

Leu Asp Phe Leu Lys Ser Asp Gly Phe Ala Asn Arg Asn Phe Met Gln
                725                 730                 735

Leu Ile His Asp Asp Ser Leu Thr Phe Lys Glu Asp Ile Gln Lys Ala
            740                 745                 750

Gln Val Ser Gly Gln Gly Asp Ser Leu His Glu His Ile Ala Asn Leu
        755                 760                 765

Ala Gly Ser Pro Ala Ile Lys Lys Gly Ile Leu Gln Thr Val Lys Val
    770                 775                 780

Val Asp Glu Leu Val Lys Val Met Gly Arg His Lys Pro Glu Asn Ile
785                 790                 795                 800

Val Ile Glu Met Ala Arg Glu Asn Gln Thr Thr Gln Lys Gly Gln Lys
                805                 810                 815

Asn Ser Arg Glu Arg Met Lys Arg Ile Glu Glu Gly Ile Lys Glu Leu
            820                 825                 830

Gly Ser Gln Ile Leu Lys Glu His Pro Val Glu Asn Thr Gln Leu Gln
        835                 840                 845

Asn Glu Lys Leu Tyr Leu Tyr Tyr Leu Gln Asn Gly Arg Asp Met Tyr
    850                 855                 860

Val Asp Gln Glu Leu Asp Ile Asn Arg Leu Ser Asp Tyr Asp Val Asp
865                 870                 875                 880

Ala Ile Val Pro Gln Ser Phe Leu Lys Asp Asp Ser Ile Asp Asn Lys
                885                 890                 895

Val Leu Thr Arg Ser Asp Lys Asn Arg Gly Lys Ser Asp Asn Val Pro
            900                 905                 910

Ser Glu Glu Val Val Lys Lys Met Lys Asn Tyr Trp Arg Gln Leu Leu
        915                 920                 925

Asn Ala Lys Leu Ile Thr Gln Arg Lys Phe Asp Asn Leu Thr Lys Ala
    930                 935                 940

Glu Arg Gly Gly Leu Ser Glu Leu Asp Lys Ala Gly Phe Ile Lys Arg
945                 950                 955                 960

Gln Leu Val Glu Thr Arg Gln Ile Thr Lys His Val Ala Gln Ile Leu
                965                 970                 975

Asp Ser Arg Met Asn Thr Lys Tyr Asp Glu Asn Asp Lys Leu Ile Arg
            980                 985                 990

Glu Val Lys Val Ile Thr Leu Lys  Ser Lys Leu Val Ser  Asp Phe Arg
        995                 1000                 1005

Lys Asp  Phe Gln Phe Tyr Lys  Val Arg Glu Ile Asn  Asn Tyr His
    1010                 1015                 1020

His Ala  His Asp Ala Tyr Leu  Asn Ala Val Val Gly  Thr Ala Leu
    1025                 1030                 1035

Ile Lys  Lys Tyr Pro Lys Leu  Glu Ser Glu Phe Val  Tyr Gly Asp
    1040                 1045                 1050

Tyr Lys  Val Tyr Asp Val Arg  Lys Met Ile Ala Lys  Ser Glu Gln
    1055                 1060                 1065

Glu Ile  Gly Lys Ala Thr Ala  Lys Tyr Phe Phe Tyr  Ser Asn Ile
```

```
    1070                1075                1080

Met Asn  Phe Phe Lys Thr Glu  Ile Thr Leu Ala Asn  Gly Glu Ile
    1085                1090                1095

Arg Lys  Arg Pro Leu Ile Glu  Thr Asn Gly Glu Thr  Gly Glu Ile
    1100                1105                1110

Val Trp  Asp Lys Gly Arg Asp  Phe Ala Thr Val Arg  Lys Val Leu
    1115                1120                1125

Ser Met  Pro Gln Val Asn Ile  Val Lys Lys Thr Glu  Val Gln Thr
    1130                1135                1140

Gly Gly  Phe Ser Lys Glu Ser  Ile Leu Pro Lys Arg  Asn Ser Asp
    1145                1150                1155

Lys Leu  Ile Ala Arg Lys Lys  Asp Trp Asp Pro Lys  Lys Tyr Gly
    1160                1165                1170

Gly Phe  Asp Ser Pro Thr Val  Ala Tyr Ser Val Leu  Val Val Ala
    1175                1180                1185

Lys Val  Glu Lys Gly Lys Ser  Lys Lys Leu Lys Ser  Val Lys Glu
    1190                1195                1200

Leu Leu  Gly Ile Thr Ile Met  Glu Arg Ser Ser Phe  Glu Lys Asn
    1205                1210                1215

Pro Ile  Asp Phe Leu Glu Ala  Lys Gly Tyr Lys Glu  Val Lys Lys
    1220                1225                1230

Asp Leu  Ile Ile Lys Leu Pro  Lys Tyr Ser Leu Phe  Glu Leu Glu
    1235                1240                1245

Asn Gly  Arg Lys Arg Met Leu  Ala Ser Ala Gly Glu  Leu Gln Lys
    1250                1255                1260

Gly Asn  Glu Leu Ala Leu Pro  Ser Lys Tyr Val Asn  Phe Leu Tyr
    1265                1270                1275

Leu Ala  Ser His Tyr Glu Lys  Leu Lys Gly Ser Pro  Glu Asp Asn
    1280                1285                1290

Glu Gln  Lys Gln Leu Phe Val  Glu Gln His Lys His  Tyr Leu Asp
    1295                1300                1305

Glu Ile  Ile Glu Gln Ile Ser  Glu Phe Ser Lys Arg  Val Ile Leu
    1310                1315                1320

Ala Asp  Ala Asn Leu Asp Lys  Val Leu Ser Ala Tyr  Asn Lys His
    1325                1330                1335

Arg Asp  Lys Pro Ile Arg Glu  Gln Ala Glu Asn Ile  Ile His Leu
    1340                1345                1350

Phe Thr  Leu Thr Asn Leu Gly  Ala Pro Ala Ala Phe  Lys Tyr Phe
    1355                1360                1365

Asp Thr  Thr Ile Asp Arg Lys  Arg Tyr Thr Ser Thr  Lys Glu Val
    1370                1375                1380

Leu Asp  Ala Thr Leu Ile His  Gln Ser Ile Thr Gly  Leu Tyr Glu
    1385                1390                1395

Thr Arg  Ile Asp Leu Ser Gln  Leu Gly Gly Asp Glu  Gly Ala Pro
    1400                1405                1410

Lys Lys  Lys Arg Lys Val Gly  Ser Ser Gly Ser Pro  Lys Lys Lys
    1415                1420                1425

Arg Lys  Val Gly Ser Asp Ala  Leu Asp Asp Phe Asp  Leu Asp Met
    1430                1435                1440

Leu Gly  Ser Asp Ala Leu Asp  Asp Phe Gly Gly Gly  Ser Met Asp
    1445                1450                1455

Ser Leu  Leu Met Asn Arg Arg  Lys Phe Leu Tyr Gln  Phe Lys Asn
    1460                1465                1470
```

```
Val Arg  Trp Ala Lys Gly Arg  Arg Glu Thr Tyr Leu  Cys Tyr Val
    1475                 1480                 1485

Val Lys  Arg Arg Asp Ser Ala  Thr Ser Phe Ser Leu  Asp Phe Gly
    1490                 1495                 1500

Tyr Leu  Arg Asn Lys Asn Gly  Cys His Val Glu Leu  Leu Phe Leu
    1505                 1510                 1515

Arg Tyr  Ile Ser Asp Trp Asp  Leu Asp Pro Gly Arg  Cys Tyr Arg
    1520                 1525                 1530

Val Thr  Trp Phe Thr Ser Trp  Ser Pro Cys Tyr Asp  Cys Ala Arg
    1535                 1540                 1545

His Val  Ala Asp Phe Leu Arg  Gly Asn Pro Asn Leu  Ser Leu Arg
    1550                 1555                 1560

Ile Phe  Thr Ala Arg Leu Tyr  Phe Cys Glu Asp Arg  Lys Ala Glu
    1565                 1570                 1575

Pro Glu  Gly Leu Arg Arg Leu  His Arg Ala Gly Val  Gln Ile Ala
    1580                 1585                 1590

Ile Met  Thr Phe Lys Asp Tyr  Phe Tyr Cys Trp Asn  Thr Phe Val
    1595                 1600                 1605

Glu Asn  His Glu Arg Thr Phe  Lys Ala Trp Glu Gly  Leu His Glu
    1610                 1615                 1620

Asn Ser  Val Arg Leu Ser Arg  Gln Leu Arg Arg Ile  Leu Leu Pro
    1625                 1630                 1635

Leu Tyr  Glu Val Asp Asp Leu  Arg Asp Ala Phe Arg  Thr Trp Gly
    1640                 1645                 1650

Arg Asp  Tyr Lys Asp Asp Asp  Asp Lys
    1655                 1660
```

<210> SEQ ID NO 26
<211> LENGTH: 4941
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Coding sequence of dcas9-aidm

<400> SEQUENCE: 26

```
atggactata aggaccacga cggagactac aaggatcatg atattgatta caaagacgat     60

gacgataaga tggccccaaa gaagaagcgg aaggtcggta tccacggagt cccagcagct    120

accatggaca agaagtattc tatcggactg gccatcggga ctaatagcgt cgggtgggcc    180

gtgatcactg acgagtacaa ggtgccctct aagaagttca aggtgctcgg gaacaccgac    240

cggcattcca tcaagaaaaa tctgatcgga gctctcctct ttgattcagg ggagaccgct    300

gaagcaaccc gcctcaagcg gactgctaga cggcggtaca ccaggaggaa gaaccggatt    360

tgttaccttc aagagatatt ctccaacgaa atggcaaagg tcgacgacag cttcttccat    420

aggctggaag aatcattcct cgtggaagag gataagaagc atgaacggca tcccatcttc    480

ggtaatatcg tcgacgaggt ggcctatcac gagaaatacc caaccatcta ccatcttcgc    540

aaaaagctgg tggactcaac cgacaaggca gacctccggc ttatctacct ggccctggcc    600

cacatgatca agttcagagg ccacttcctg atcgagggcg acctcaatcc tgacaatagc    660

gatgtggata aactgttcat ccagctggtg cagacttaca accagctctt tgaagagaac    720

cccatcaatg caagcggagt cgatgccaag gccattctgt cagcccggct gtcaaagagc    780
```

-continued

```
cgcagacttg agaatcttat cgctcagctg ccgggtgaaa agaaaaatgg actgttcggg    840
aacctgattg ctctttcact tgggctgact cccaatttca agtctaattt cgacctggca    900
gaggatgcca agctgcaact gtccaaggac acctatgatg acgatctcga caacctcctg    960
gcccagatcg gtgaccaata cgccgacctt ttccttgctg ctaagaatct ttctgacgcc   1020
atcctgctgt ctgacattct ccgcgtgaac actgaaatca ccaaggcccc tctttcagct   1080
tcaatgatta agcggtatga tgagcaccac caggacctga ccctgcttaa ggcactcgtc   1140
cggcagcagc ttccggagaa gtacaaggaa atcttctttg accagtcaaa gaatggatac   1200
gccggctaca tcgacggagg tgcctcccaa gaggaatttt ataagtttat caaacctatc   1260
cttgagaaga tggacggcac cgaagagctc ctcgtgaaac tgaatcggga ggatctgctg   1320
cggaagcagc gcactttcga caatgggagc attccccacc agatccatct tggggagctt   1380
cacgccatcc ttcggcgcca agaggacttc taccccttc ttaaggacaa cagggagaag    1440
attgagaaaa ttctcacttt ccgcatcccc tactacgtgg gacccctcgc cagaggaaat   1500
agccggtttg cttggatgac cagaaagtca gaagaaacta tcactccctg gaacttcgaa   1560
gaggtggtgg acaagggagc cagcgctcag tcattcatcg aacggatgac taacttcgat   1620
aagaacctcc ccaatgagaa ggtcctgccg aaacattccc tgctctacga gtactttacc   1680
gtgtacaacg agctgaccaa ggtgaaatat gtcaccgaag ggatgaggaa gcccgcattc   1740
ctgtcaggcg aacaaaagaa ggcaattgtg gaccttctgt tcaagaccaa tagaaaggtg   1800
accgtgaagc agctgaagga ggactatttc aagaaaattg aatgcttcga ctctgtggag   1860
attagcgggg tcgaagatcg gttcaacgca agcctgggta cctaccatga tctgcttaag   1920
atcatcaagg acaaggattt tctggacaat gaggagaacg aggacatcct tgaggacatt   1980
gtcctgactc tcactctgtt cgaggaccgg gaaatgatcg aggagaggct taagacctac   2040
gcccatctgt tcgacgataa agtgatgaag caacttaaac ggagaagata taccggatgg   2100
ggacgcctta gccgcaaact catcaacgga atccgggaca aacagagcgg aaagaccatt   2160
cttgatttcc ttaagagcga cggattcgct aatcgcaact tcatgcaact tatccatgat   2220
gattccctga cctttaagga ggacatccag aaggcccaag tgtctggaca aggtgactca   2280
ctgcacgagc atatcgcaaa tctggctggt tcacccgcta ttaagaaggg tattctccag   2340
accgtgaaag tcgtggacga gctggtcaag gtgatgggtc gccataaacc agagaacatt   2400
gtcatcgaga tggccaggga aaaccagact acccagaagg gacagaagaa cagcagggag   2460
cggatgaaaa gaattgagga agggattaag gagctcgggt cacagatcct taaagagcac   2520
ccggtggaaa acacccagct tcagaatgag aagctctatc tgtactacct tcaaaatgga   2580
cgcgatatgt atgtggacca agagcttgat atcaacaggc tctcagacta cgacgtggac   2640
gccatcgtcc ctcagagctt cctcaaagac gactcaattg acaataaggt gctgactcgc   2700
tcagacaaga accggggaaa gtcagataac gtgccctcag aggaagtcgt gaaaaagatg   2760
aagaactatt ggcgccagct tctgaacgca aagctgatca ctcagcggaa gttcgacaat   2820
ctcactaagg ctgagagggg cggactgagc gaactggaca aagcaggatt cattaaacgg   2880
caacttgtgg agactcggca gattactaaa catgtcgccc aaatccttga ctcacgcatg   2940
aataccaagt acgacgaaaa cgacaaactt atccgcgagg tgaaggtgat taccctgaag   3000
tccaagctgg tcagcgattt cagaaaggac tttcaattct acaaagtgcg ggagatcaat   3060
aactatcatc atgctcatga cgcatatctg aatgccgtgg tgggaaccgc cctgatcaag   3120
aagtacccaa agctggaaag cgagttcgtg tacggagact acaaggtcta cgacgtgcgc   3180
```

```
aagatgattg ccaaatctga gcaggagatc ggaaaggcca ccgcaaagta cttcttctac   3240
agcaacatca tgaatttctt caagaccgaa atcacccttg caaacggtga gatccggaag   3300
aggccgctca tcgagactaa tggggagact ggcgaaatcg tgtgggacaa gggcagagat   3360
ttcgctaccg tgcgcaaagt gctttctatg cctcaagtga acatcgtgaa gaaaaccgag   3420
gtgcaaaccg gaggcttttc taaggaatca atcctcccca agcgcaactc cgacaagctc   3480
attgcaagga agaaggattg ggaccctaag aagtacggcg gattcgattc accaactgtg   3540
gcttattctg tcctggtcgt ggctaaggtg gaaaaaggaa agtctaagaa gctcaagagc   3600
gtgaaggaac tgctgggtat caccattatg gagcgcagct ccttcgagaa gaacccaatt   3660
gactttctcg aagccaaagg ttacaaggaa gtcaagaagg accttatcat caagctccca   3720
aagtatagcc tgttcgaact ggagaatggg cggaagcgga tgctcgcctc cgctggcgaa   3780
cttcagaagg gtaatgagct ggctctcccc tccaagtacg tgaatttcct ctaccttgca   3840
agccattacg agaagctgaa ggggagcccc gaggacaacg agcaaaagca actgtttgtg   3900
gagcagcata agcattatct ggacgagatc attgagcaga tttccgagtt ttctaaacgc   3960
gtcattctcg ctgatgccaa cctcgataaa gtccttagcg catacaataa gcacagagac   4020
aaaccaattc gggagcaggc tgagaatatc atccacctgt tcaccctcac caatcttggt   4080
gcccctgccg cattcaagta cttcgacacc accatcgacc ggaaacgcta tacctccacc   4140
aaagaagtgc tggacgccac cctcatccac cagagcatca ccggacttta cgaaactcgg   4200
attgacctct cacagctcgg aggggatgag ggagctccca agaaaaagcg caaggtaggt   4260
agttccggat ctccgaaaaa gaaacgcaaa gttggtagtg atgctttaga cgattttgac   4320
ttagatatgc ttggttcaga cgcgttagac gacttcggtg gaggatccat ggacagcctc   4380
ttgatgaacc ggaggaagtt tctttaccaa ttcaaaaatg tccgctgggc taagggtcgg   4440
cgtgagacct acctgtgcta cgtagtgaag aggcgtgaca gtgctacatc cttttcactg   4500
gactttggtt atcttcgcaa taagaacggc tgccacgtgg aattgctctt cctccgctac   4560
atctcggact gggacctaga ccctggccgc tgctaccgcg tcacctggtt cacctcctgg   4620
agcccctgct acgactgtgc ccgacatgtg gccgactttc tgcgagggaa ccccaacctc   4680
agtctgagga tcttcaccgc gcgcctctac ttctgtgagg accgcaaggc tgagcccgag   4740
gggctgcggc ggctgcaccg cgccggggtg caaatagcca tcatgacctt caaagattat   4800
ttttactgct ggaatacttt tgtagaaaac catgaaagaa ctttcaaagc ctgggaaggg   4860
ctgcatgaaa attcagttcg tctctccaga cagcttcggc gcatcctttt gcccgattac   4920
aaagacgatg acgataagtg a                                              4941
```

<210> SEQ ID NO 27
<211> LENGTH: 1646
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Amino acid sequence of dcas9-aidm

<400> SEQUENCE: 27

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30
```

```
Gly Ile His Gly Val Pro Ala Ala Thr Met Asp Lys Lys Tyr Ser Ile
        35                  40                  45

Gly Leu Ala Ile Gly Thr Asn Ser Val Gly Trp Ala Val Ile Thr Asp
    50                  55                  60

Glu Tyr Lys Val Pro Ser Lys Lys Phe Lys Val Leu Gly Asn Thr Asp
65                  70                  75                  80

Arg His Ser Ile Lys Lys Asn Leu Ile Gly Ala Leu Leu Phe Asp Ser
                85                  90                  95

Gly Glu Thr Ala Glu Ala Thr Arg Leu Lys Arg Thr Ala Arg Arg Arg
            100                 105                 110

Tyr Thr Arg Arg Lys Asn Arg Ile Cys Tyr Leu Gln Glu Ile Phe Ser
        115                 120                 125

Asn Glu Met Ala Lys Val Asp Asp Ser Phe Phe His Arg Leu Glu Glu
    130                 135                 140

Ser Phe Leu Val Glu Glu Asp Lys Lys His Glu Arg His Pro Ile Phe
145                 150                 155                 160

Gly Asn Ile Val Asp Glu Val Ala Tyr His Glu Lys Tyr Pro Thr Ile
                165                 170                 175

Tyr His Leu Arg Lys Lys Leu Val Asp Ser Thr Asp Lys Ala Asp Leu
            180                 185                 190

Arg Leu Ile Tyr Leu Ala Leu Ala His Met Ile Lys Phe Arg Gly His
        195                 200                 205

Phe Leu Ile Glu Gly Asp Leu Asn Pro Asp Asn Ser Asp Val Asp Lys
    210                 215                 220

Leu Phe Ile Gln Leu Val Gln Thr Tyr Asn Gln Leu Phe Glu Glu Asn
225                 230                 235                 240

Pro Ile Asn Ala Ser Gly Val Asp Ala Lys Ala Ile Leu Ser Ala Arg
                245                 250                 255

Leu Ser Lys Ser Arg Arg Leu Glu Asn Leu Ile Ala Gln Leu Pro Gly
            260                 265                 270

Glu Lys Lys Asn Gly Leu Phe Gly Asn Leu Ile Ala Leu Ser Leu Gly
        275                 280                 285

Leu Thr Pro Asn Phe Lys Ser Asn Phe Asp Leu Ala Glu Asp Ala Lys
    290                 295                 300

Leu Gln Leu Ser Lys Asp Thr Tyr Asp Asp Asp Leu Asp Asn Leu Leu
305                 310                 315                 320

Ala Gln Ile Gly Asp Gln Tyr Ala Asp Leu Phe Leu Ala Ala Lys Asn
                325                 330                 335

Leu Ser Asp Ala Ile Leu Leu Ser Asp Ile Leu Arg Val Asn Thr Glu
            340                 345                 350

Ile Thr Lys Ala Pro Leu Ser Ala Ser Met Ile Lys Arg Tyr Asp Glu
        355                 360                 365

His His Gln Asp Leu Thr Leu Leu Lys Ala Leu Val Arg Gln Gln Leu
    370                 375                 380

Pro Glu Lys Tyr Lys Glu Ile Phe Phe Asp Gln Ser Lys Asn Gly Tyr
385                 390                 395                 400

Ala Gly Tyr Ile Asp Gly Gly Ala Ser Gln Glu Glu Phe Tyr Lys Phe
                405                 410                 415

Ile Lys Pro Ile Leu Glu Lys Met Asp Gly Thr Glu Glu Leu Leu Val
            420                 425                 430

Lys Leu Asn Arg Glu Asp Leu Leu Arg Lys Gln Arg Thr Phe Asp Asn
        435                 440                 445
```

```
Gly Ser Ile Pro His Gln Ile His Leu Gly Glu Leu His Ala Ile Leu
    450                 455                 460

Arg Arg Gln Glu Asp Phe Tyr Pro Phe Leu Lys Asp Asn Arg Glu Lys
465                 470                 475                 480

Ile Glu Lys Ile Leu Thr Phe Arg Ile Pro Tyr Tyr Val Gly Pro Leu
                485                 490                 495

Ala Arg Gly Asn Ser Arg Phe Ala Trp Met Thr Arg Lys Ser Glu Glu
            500                 505                 510

Thr Ile Thr Pro Trp Asn Phe Glu Glu Val Val Asp Lys Gly Ala Ser
        515                 520                 525

Ala Gln Ser Phe Ile Glu Arg Met Thr Asn Phe Asp Lys Asn Leu Pro
    530                 535                 540

Asn Glu Lys Val Leu Pro Lys His Ser Leu Leu Tyr Glu Tyr Phe Thr
545                 550                 555                 560

Val Tyr Asn Glu Leu Thr Lys Val Lys Tyr Val Thr Glu Gly Met Arg
                565                 570                 575

Lys Pro Ala Phe Leu Ser Gly Glu Gln Lys Lys Ala Ile Val Asp Leu
            580                 585                 590

Leu Phe Lys Thr Asn Arg Lys Val Thr Val Lys Gln Leu Lys Glu Asp
        595                 600                 605

Tyr Phe Lys Lys Ile Glu Cys Phe Asp Ser Val Glu Ile Ser Gly Val
    610                 615                 620

Glu Asp Arg Phe Asn Ala Ser Leu Gly Thr Tyr His Asp Leu Leu Lys
625                 630                 635                 640

Ile Ile Lys Asp Lys Asp Phe Leu Asp Asn Glu Glu Asn Glu Asp Ile
                645                 650                 655

Leu Glu Asp Ile Val Leu Thr Leu Thr Leu Phe Glu Asp Arg Glu Met
            660                 665                 670

Ile Glu Glu Arg Leu Lys Thr Tyr Ala His Leu Phe Asp Asp Lys Val
        675                 680                 685

Met Lys Gln Leu Lys Arg Arg Arg Tyr Thr Gly Trp Gly Arg Leu Ser
    690                 695                 700

Arg Lys Leu Ile Asn Gly Ile Arg Asp Lys Gln Ser Gly Lys Thr Ile
705                 710                 715                 720

Leu Asp Phe Leu Lys Ser Asp Gly Phe Ala Asn Arg Asn Phe Met Gln
                725                 730                 735

Leu Ile His Asp Asp Ser Leu Thr Phe Lys Glu Asp Ile Gln Lys Ala
            740                 745                 750

Gln Val Ser Gly Gln Gly Asp Ser Leu His Glu His Ile Ala Asn Leu
        755                 760                 765

Ala Gly Ser Pro Ala Ile Lys Lys Gly Ile Leu Gln Thr Val Lys Val
    770                 775                 780

Val Asp Glu Leu Val Lys Val Met Gly Arg His Lys Pro Glu Asn Ile
785                 790                 795                 800

Val Ile Glu Met Ala Arg Glu Asn Gln Thr Thr Gln Lys Gly Gln Lys
                805                 810                 815

Asn Ser Arg Glu Arg Met Lys Arg Ile Glu Glu Gly Ile Lys Glu Leu
            820                 825                 830

Gly Ser Gln Ile Leu Lys Glu His Pro Val Glu Asn Thr Gln Leu Gln
        835                 840                 845

Asn Glu Lys Leu Tyr Leu Tyr Tyr Leu Gln Asn Gly Arg Asp Met Tyr
    850                 855                 860

Val Asp Gln Glu Leu Asp Ile Asn Arg Leu Ser Asp Tyr Asp Val Asp
```

```
865                 870                 875                 880

Ala Ile Val Pro Gln Ser Phe Leu Lys Asp Asp Ser Ile Asp Asn Lys
                885                 890                 895

Val Leu Thr Arg Ser Asp Lys Asn Arg Gly Lys Ser Asp Asn Val Pro
            900                 905                 910

Ser Glu Glu Val Val Lys Lys Met Lys Asn Tyr Trp Arg Gln Leu Leu
        915                 920                 925

Asn Ala Lys Leu Ile Thr Gln Arg Lys Phe Asp Asn Leu Thr Lys Ala
    930                 935                 940

Glu Arg Gly Gly Leu Ser Glu Leu Asp Lys Ala Gly Phe Ile Lys Arg
945                 950                 955                 960

Gln Leu Val Glu Thr Arg Gln Ile Thr Lys His Val Ala Gln Ile Leu
                965                 970                 975

Asp Ser Arg Met Asn Thr Lys Tyr Asp Glu Asn Asp Lys Leu Ile Arg
            980                 985                 990

Glu Val Lys Val Ile Thr Leu Lys  Ser Lys Leu Val Ser  Asp Phe Arg
        995                 1000                1005

Lys Asp  Phe Gln Phe Tyr Lys  Val Arg Glu Ile Asn  Asn Tyr His
    1010                 1015                 1020

His Ala  His Asp Ala Tyr Leu  Asn Ala Val Val Gly  Thr Ala Leu
    1025                 1030                 1035

Ile Lys  Lys Tyr Pro Lys Leu  Glu Ser Glu Phe Val  Tyr Gly Asp
    1040                 1045                 1050

Tyr Lys  Val Tyr Asp Val Arg  Lys Met Ile Ala Lys  Ser Glu Gln
    1055                 1060                 1065

Glu Ile  Gly Lys Ala Thr Ala  Lys Tyr Phe Phe Tyr  Ser Asn Ile
    1070                 1075                 1080

Met Asn  Phe Phe Lys Thr Glu  Ile Thr Leu Ala Asn  Gly Glu Ile
    1085                 1090                 1095

Arg Lys  Arg Pro Leu Ile Glu  Thr Asn Gly Glu Thr  Gly Glu Ile
    1100                 1105                 1110

Val Trp  Asp Lys Gly Arg Asp  Phe Ala Thr Val Arg  Lys Val Leu
    1115                 1120                 1125

Ser Met  Pro Gln Val Asn Ile  Val Lys Lys Thr Glu  Val Gln Thr
    1130                 1135                 1140

Gly Gly  Phe Ser Lys Glu Ser  Ile Leu Pro Lys Arg  Asn Ser Asp
    1145                 1150                 1155

Lys Leu  Ile Ala Arg Lys Lys  Asp Trp Asp Pro Lys  Lys Tyr Gly
    1160                 1165                 1170

Gly Phe  Asp Ser Pro Thr Val  Ala Tyr Ser Val Leu  Val Val Ala
    1175                 1180                 1185

Lys Val  Glu Lys Gly Lys Ser  Lys Lys Leu Lys Ser  Val Lys Glu
    1190                 1195                 1200

Leu Leu  Gly Ile Thr Ile Met  Glu Arg Ser Ser Phe  Glu Lys Asn
    1205                 1210                 1215

Pro Ile  Asp Phe Leu Glu Ala  Lys Gly Tyr Lys Glu  Val Lys Lys
    1220                 1225                 1230

Asp Leu  Ile Ile Lys Leu Pro  Lys Tyr Ser Leu Phe  Glu Leu Glu
    1235                 1240                 1245

Asn Gly  Arg Lys Arg Met Leu  Ala Ser Ala Gly Glu  Leu Gln Lys
    1250                 1255                 1260

Gly Asn  Glu Leu Ala Leu Pro  Ser Lys Tyr Val Asn  Phe Leu Tyr
    1265                 1270                 1275
```

```
Leu Ala  Ser His Tyr Glu Lys  Leu Lys Gly Ser Pro  Glu Asp Asn
    1280                 1285                 1290

Glu Gln  Lys Gln Leu Phe Val  Glu Gln His Lys His  Tyr Leu Asp
    1295                 1300                 1305

Glu Ile  Ile Glu Gln Ile Ser  Glu Phe Ser Lys Arg  Val Ile Leu
    1310                 1315                 1320

Ala Asp  Ala Asn Leu Asp Lys  Val Leu Ser Ala Tyr  Asn Lys His
    1325                 1330                 1335

Arg Asp  Lys Pro Ile Arg Glu  Gln Ala Glu Asn Ile  Ile His Leu
    1340                 1345                 1350

Phe Thr  Leu Thr Asn Leu Gly  Ala Pro Ala Ala Phe  Lys Tyr Phe
    1355                 1360                 1365

Asp Thr  Thr Ile Asp Arg Lys  Arg Tyr Thr Ser Thr  Lys Glu Val
    1370                 1375                 1380

Leu Asp  Ala Thr Leu Ile His  Gln Ser Ile Thr Gly  Leu Tyr Glu
    1385                 1390                 1395

Thr Arg  Ile Asp Leu Ser Gln  Leu Gly Gly Asp Glu  Gly Ala Pro
    1400                 1405                 1410

Lys Lys  Lys Arg Lys Val Gly  Ser Ser Gly Ser Pro  Lys Lys Lys
    1415                 1420                 1425

Arg Lys  Val Gly Ser Asp Ala  Leu Asp Asp Phe Asp  Leu Asp Met
    1430                 1435                 1440

Leu Gly  Ser Asp Ala Leu Asp  Asp Phe Gly Gly Gly  Ser Met Asp
    1445                 1450                 1455

Ser Leu  Leu Met Asn Arg Arg  Lys Phe Leu Tyr Gln  Phe Lys Asn
    1460                 1465                 1470

Val Arg  Trp Ala Lys Gly Arg  Arg Glu Thr Tyr Leu  Cys Tyr Val
    1475                 1480                 1485

Val Lys  Arg Arg Asp Ser Ala  Thr Ser Phe Ser Leu  Asp Phe Gly
    1490                 1495                 1500

Tyr Leu  Arg Asn Lys Asn Gly  Cys His Val Glu Leu  Leu Phe Leu
    1505                 1510                 1515

Arg Tyr  Ile Ser Asp Trp Asp  Leu Asp Pro Gly Arg  Cys Tyr Arg
    1520                 1525                 1530

Val Thr  Trp Phe Thr Ser Trp  Ser Pro Cys Tyr Asp  Cys Ala Arg
    1535                 1540                 1545

His Val  Ala Asp Phe Leu Arg  Gly Asn Pro Asn Leu  Ser Leu Arg
    1550                 1555                 1560

Ile Phe  Thr Ala Arg Leu Tyr  Phe Cys Glu Asp Arg  Lys Ala Glu
    1565                 1570                 1575

Pro Glu  Gly Leu Arg Arg Leu  His Arg Ala Gly Val  Gln Ile Ala
    1580                 1585                 1590

Ile Met  Thr Phe Lys Asp Tyr  Phe Tyr Cys Trp Asn  Thr Phe Val
    1595                 1600                 1605

Glu Asn  His Glu Arg Thr Phe  Lys Ala Trp Glu Gly  Leu His Glu
    1610                 1615                 1620

Asn Ser  Val Arg Leu Ser Arg  Gln Leu Arg Arg Ile  Leu Leu Pro
    1625                 1630                 1635

Asp Tyr  Lys Asp Asp Asp Asp  Lys
    1640                 1645
```

<210> SEQ ID NO 28
<211> LENGTH: 4731

```
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Coding sequence of AIDx-XTEN-dCas9

<400> SEQUENCE: 28

atggacagcc tcttgatgaa ccggaggaag tttctttacc aattcaaaaa tgtccgctgg     60
gctaagggtc ggcgtgagac ctacctgtgc tacgtagtga agaggcgtga cagtgctaca    120
tccttttcac tggactttgg ttatcttcgc aataagaacg gctgccacgt ggaattgctc    180
ttcctccgct acatctcgga ctgggaccta gaccctggcc gctgctaccg cgtcacctgg    240
ttcacctcct ggagcccctg ctacgactgt gcccgacatg tggccgactt tctgcgaggg    300
aaccccaacc tcagtctgag gatcttcacc gcgcgcctct acttctgtga ggaccgcaag    360
gctgagcccg aggggctgcg gcggctgcac cgcgccgggg tgcaaatagc catcatgacc    420
ttcaaagatt atttttactg ctggaatact tttgtagaaa accatgaaag aactttcaaa    480
gcctgggaag ggctgcatga aaattcagtt cgtctctcca gacagcttcg gcgcatcctt    540
ttgcccagcg gcagcgagac tcccgggacc tcagagtccg ccacacccga aagtgataaa    600
aagtattcta ttggtttagc catcggcact aattccgttg gatgggctgt cataaccgat    660
gaatacaaag taccttcaaa gaaatttaag gtgttgggga acacagaccg tcattcgatt    720
aaaaagaatc ttatcggtgc cctcctattc gatagtggcg aaacggcaga ggcgactcgc    780
ctgaaacgaa ccgctcggag aaggtataca cgtcgcaaga accgaatatg ttacttacaa    840
gaaattttta gcaatgagat ggccaaagtt gacgattctt tctttcaccg tttggaagag    900
tccttccttg tcgaagagga caagaaacat gaacggcacc ccatctttgg aaacatagta    960
gatgaggtgg catatcatga aaagtaccca acgatttatc acctcagaaa aaagctagtt   1020
gactcaactg ataaagcgga cctgaggtta atctacttgg ctcttgccca tatgataaag   1080
ttccgtgggc actttctcat tgagggtgat ctaaatccgg acaactcgga tgtcgacaaa   1140
ctgttcatcc agttagtaca aacctataat cagttgtttg aagagaaccc tataaatgca   1200
agtggcgtgg atgcgaaggc tattcttagc gcccgcctct ctaaatcccg acggctagaa   1260
aacctgatcg cacaattacc cggagagaag aaaaatgggt tgttcggtaa ccttatagcg   1320
ctctcactag gcctgacacc aaattttaag tcgaacttcg acttagctga agatgccaaa   1380
ttgcagctta gtaaggacac gtacgatgac gatctcgaca atctactggc acaaattgga   1440
gatcagtatg cggacttatt tttggctgcc aaaaacctta gcgatgcaat cctcctatct   1500
gacatactga gagttaatac tgagattacc aaggcgccgt tatccgcttc aatgatcaaa   1560
aggtacgatg aacatcacca agacttgaca cttctcaagg ccctagtccg tcagcaactg   1620
cctgagaaat ataaggaaat attctttgat cagtcgaaaa acgggtacgc aggttatatt   1680
gacggcggag cgagtcaaga ggaattctac aagtttatca aacccatatt agagaagatg   1740
gatgggacgg aagagttgct tgtaaaactc aatcgcgaag atctactgcg aaagcagcgg   1800
actttcgaca acggtagcat tccacatcaa atccacttag gcgaattgca tgctatactt   1860
agaaggcagg aggattttta tccgttcctc aaagacaatc gtgaaaagat tgagaaaatc   1920
ctaacctttc gcatacctta ctatgtggga cccctggccc gagggaactc tcggttcgca   1980
tggatgacaa gaaagtccga agaaacgatt actccatgga attttgagga agttgtcgat   2040
aaaggtgcgt cagctcaatc gttcatcgag aggatgacca actttgacaa gaatttaccg   2100
```

-continued

```
aacgaaaaag tattgcctaa gcacagttta ctttacgagt atttcacagt gtacaatgaa   2160
ctcacgaaag ttaagtatgt cactgagggc atgcgtaaac ccgcctttct aagcggagaa   2220
cagaagaaag caatagtaga tctgttattc aagaccaacc gcaaagtgac agttaagcaa   2280
ttgaaagagg actactttaa gaaaattgaa tgcttcgatt ctgtcgagat ctccggggta   2340
gaagatcgat ttaatgcgtc acttggtacg tatcatgacc tcctaaagat aattaaagat   2400
aaggacttcc tggataacga agagaatgaa gatatcttag aagatatagt gttgactctt   2460
accctctttg aagatcggga aatgattgag gaaagactaa aaacatacgc tcacctgttc   2520
gacgataagg ttatgaaaca gttaaagagg cgtcgctata cgggctgggg acgattgtcg   2580
cggaaactta tcaacgggat aagagacaag caaagtggta aaactattct cgattttcta   2640
aagagcgacg gcttcgccaa taggaacttt atgcagctga tccatgatga ctctttaacc   2700
ttcaaagagg atatacaaaa ggcacaggtt tccggacaag gggactcatt gcacgaacat   2760
attgcgaatc ttgctggttc gccagccatc aaaaagggca tactccagac agtcaaagta   2820
gtggatgagc tagttaaggt catgggacgt cacaaaccgg aaaacattgt aatcgagatg   2880
gcacgcgaaa atcaaacgac tcagaagggg caaaaaaaca gtcgagagcg gatgaagaga   2940
atagaagagg gtattaaaga actgggcagc cagatcttaa aggagcatcc tgtggaaaat   3000
acccaattgc agaacgagaa actttacctc tattacctac aaaatggaag ggacatgtat   3060
gttgatcagg aactggacat aaaccgttta tctgattacg acgtcgatgc cattgtaccc   3120
caatcctttt tgaaggacga ttcaatcgac aataaagtgc ttacacgctc ggataagaac   3180
cgagggaaaa gtgacaatgt tccaagcgag gaagtcgtaa agaaaatgaa gaactattgg   3240
cggcagctcc taaatgcgaa actgataacg caaagaaagt tcgataactt aactaaagct   3300
gagaggggtg gcttgtctga acttgacaag gccggattta ttaaacgtca gctcgtggaa   3360
acccgccaaa tcacaaagca tgttgcacag atactagatt cccgaatgaa tacgaaatac   3420
gacgagaacg ataagctgat tcgggaagtc aaagtaatca ctttaaagtc aaaattggtg   3480
tcggacttca gaaaggattt tcaattctat aaagttaggg agataaataa ctaccaccat   3540
gcgcacgacg cttatcttaa tgccgtcgta gggaccgcac tcattaagaa atacccgaag   3600
ctagaaagtg agtttgtgta tggtgattac aaagtttatg acgtccgtaa gatgatcgcg   3660
aaaagcgaac aggagatagg caaggctaca gccaaatact tcttttattc taacattatg   3720
aatttcttta agacggaaat cactctggca aacggagaga tacgcaaacg acctttaatt   3780
gaaaccaatg gggagacagg tgaaatcgta tgggataagg gccgggactt cgcgacggtg   3840
agaaaagttt tgtccatgcc ccaagtcaac atagtaaaga aaactgaggt gcagaccgga   3900
gggttttcaa aggaatcgat tcttccaaaa aggaatagtg ataagctcat cgctcgtaaa   3960
aaggactggg acccgaaaaa gtacggtggc ttcgatagcc ctacagttgc ctattctgtc   4020
ctagtagtgg caaaagttga gaagggaaaa tccaagaaac tgaagtcagt caaagaatta   4080
ttggggataa cgattatgga gcgctcgtct tttgaaaaga accccatcga cttccttgag   4140
gcgaaaggtt acaaggaagt aaaaaaggat ctcataatta aactaccaaa gtatagtctg   4200
tttgagttag aaaatggccg aaaacggatg ttggctagcg ccggagagct tcaaaagggg   4260
aacgaactcg cactaccgtc taaatacgtg aatttcctgt atttagcgtc ccattacgag   4320
aagttgaaag gttcacctga agataacgaa cagaagcaac tttttgttga gcagcacaaa   4380
cattatctcg acgaaatcat agagcaaatt tcggaattca gtaagagagt catcctagct   4440
```

```
gatgccaatc tggacaaagt attaagcgca tacaacaagc acagggataa acccatacgt   4500

gagcaggcgg aaaatattat ccatttgttt actcttacca acctcggcgc tccagccgca   4560

ttcaagtatt ttgacacaac gatagatcgc aaacgataca cttctaccaa ggaggtgcta   4620

gacgcgacac tgattcacca atccatcacg ggattatatg aaactcggat agatttgtca   4680

cagcttgggg gtgactctgg tggttctccc aagaagaaga ggaaagtcta a            4731


<210> SEQ ID NO 29
<211> LENGTH: 1576
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Amino acid sequence of AIDx-XTEN-dCas9

<400> SEQUENCE: 29

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Ser Gly Ser Glu Thr Pro Gly Thr Ser Glu
            180                 185                 190

Ser Ala Thr Pro Glu Ser Asp Lys Lys Tyr Ser Ile Gly Leu Ala Ile
        195                 200                 205

Gly Thr Asn Ser Val Gly Trp Ala Val Ile Thr Asp Glu Tyr Lys Val
    210                 215                 220

Pro Ser Lys Lys Phe Lys Val Leu Gly Asn Thr Asp Arg His Ser Ile
225                 230                 235                 240

Lys Lys Asn Leu Ile Gly Ala Leu Leu Phe Asp Ser Gly Glu Thr Ala
                245                 250                 255

Glu Ala Thr Arg Leu Lys Arg Thr Ala Arg Arg Arg Tyr Thr Arg Arg
            260                 265                 270

Lys Asn Arg Ile Cys Tyr Leu Gln Glu Ile Phe Ser Asn Glu Met Ala
        275                 280                 285

Lys Val Asp Asp Ser Phe Phe His Arg Leu Glu Glu Ser Phe Leu Val
    290                 295                 300
```

```
Glu Glu Asp Lys Lys His Glu Arg His Pro Ile Phe Gly Asn Ile Val
305                 310                 315                 320

Asp Glu Val Ala Tyr His Glu Lys Tyr Pro Thr Ile Tyr His Leu Arg
                325                 330                 335

Lys Lys Leu Val Asp Ser Thr Asp Lys Ala Asp Leu Arg Leu Ile Tyr
            340                 345                 350

Leu Ala Leu Ala His Met Ile Lys Phe Arg Gly His Phe Leu Ile Glu
        355                 360                 365

Gly Asp Leu Asn Pro Asp Asn Ser Asp Val Asp Lys Leu Phe Ile Gln
    370                 375                 380

Leu Val Gln Thr Tyr Asn Gln Leu Phe Glu Glu Asn Pro Ile Asn Ala
385                 390                 395                 400

Ser Gly Val Asp Ala Lys Ala Ile Leu Ser Ala Arg Leu Ser Lys Ser
                405                 410                 415

Arg Arg Leu Glu Asn Leu Ile Ala Gln Leu Pro Gly Glu Lys Lys Asn
            420                 425                 430

Gly Leu Phe Gly Asn Leu Ile Ala Leu Ser Leu Gly Leu Thr Pro Asn
        435                 440                 445

Phe Lys Ser Asn Phe Asp Leu Ala Glu Asp Ala Lys Leu Gln Leu Ser
    450                 455                 460

Lys Asp Thr Tyr Asp Asp Asp Leu Asp Asn Leu Leu Ala Gln Ile Gly
465                 470                 475                 480

Asp Gln Tyr Ala Asp Leu Phe Leu Ala Ala Lys Asn Leu Ser Asp Ala
                485                 490                 495

Ile Leu Leu Ser Asp Ile Leu Arg Val Asn Thr Glu Ile Thr Lys Ala
            500                 505                 510

Pro Leu Ser Ala Ser Met Ile Lys Arg Tyr Asp Glu His His Gln Asp
        515                 520                 525

Leu Thr Leu Leu Lys Ala Leu Val Arg Gln Gln Leu Pro Glu Lys Tyr
    530                 535                 540

Lys Glu Ile Phe Phe Asp Gln Ser Lys Asn Gly Tyr Ala Gly Tyr Ile
545                 550                 555                 560

Asp Gly Gly Ala Ser Gln Glu Glu Phe Tyr Lys Phe Ile Lys Pro Ile
                565                 570                 575

Leu Glu Lys Met Asp Gly Thr Glu Glu Leu Leu Val Lys Leu Asn Arg
            580                 585                 590

Glu Asp Leu Leu Arg Lys Gln Arg Thr Phe Asp Asn Gly Ser Ile Pro
        595                 600                 605

His Gln Ile His Leu Gly Glu Leu His Ala Ile Leu Arg Arg Gln Glu
    610                 615                 620

Asp Phe Tyr Pro Phe Leu Lys Asp Asn Arg Glu Lys Ile Glu Lys Ile
625                 630                 635                 640

Leu Thr Phe Arg Ile Pro Tyr Tyr Val Gly Pro Leu Ala Arg Gly Asn
                645                 650                 655

Ser Arg Phe Ala Trp Met Thr Arg Lys Ser Glu Glu Thr Ile Thr Pro
            660                 665                 670

Trp Asn Phe Glu Glu Val Val Asp Lys Gly Ala Ser Ala Gln Ser Phe
        675                 680                 685

Ile Glu Arg Met Thr Asn Phe Asp Lys Asn Leu Pro Asn Glu Lys Val
    690                 695                 700

Leu Pro Lys His Ser Leu Leu Tyr Glu Tyr Phe Thr Val Tyr Asn Glu
705                 710                 715                 720
```

-continued

```
Leu Thr Lys Val Lys Tyr Val Thr Glu Gly Met Arg Lys Pro Ala Phe
                725                 730                 735

Leu Ser Gly Glu Gln Lys Lys Ala Ile Val Asp Leu Leu Phe Lys Thr
            740                 745                 750

Asn Arg Lys Val Thr Val Lys Gln Leu Lys Glu Asp Tyr Phe Lys Lys
        755                 760                 765

Ile Glu Cys Phe Asp Ser Val Glu Ile Ser Gly Val Glu Asp Arg Phe
    770                 775                 780

Asn Ala Ser Leu Gly Thr Tyr His Asp Leu Leu Lys Ile Ile Lys Asp
785                 790                 795                 800

Lys Asp Phe Leu Asp Asn Glu Glu Asn Glu Asp Ile Leu Glu Asp Ile
                805                 810                 815

Val Leu Thr Leu Thr Leu Phe Glu Asp Arg Glu Met Ile Glu Glu Arg
            820                 825                 830

Leu Lys Thr Tyr Ala His Leu Phe Asp Asp Lys Val Met Lys Gln Leu
        835                 840                 845

Lys Arg Arg Arg Tyr Thr Gly Trp Gly Arg Leu Ser Arg Lys Leu Ile
    850                 855                 860

Asn Gly Ile Arg Asp Lys Gln Ser Gly Lys Thr Ile Leu Asp Phe Leu
865                 870                 875                 880

Lys Ser Asp Gly Phe Ala Asn Arg Asn Phe Met Gln Leu Ile His Asp
                885                 890                 895

Asp Ser Leu Thr Phe Lys Glu Asp Ile Gln Lys Ala Gln Val Ser Gly
            900                 905                 910

Gln Gly Asp Ser Leu His Glu His Ile Ala Asn Leu Ala Gly Ser Pro
        915                 920                 925

Ala Ile Lys Lys Gly Ile Leu Gln Thr Val Lys Val Val Asp Glu Leu
    930                 935                 940

Val Lys Val Met Gly Arg His Lys Pro Glu Asn Ile Val Ile Glu Met
945                 950                 955                 960

Ala Arg Glu Asn Gln Thr Thr Gln Lys Gly Gln Lys Asn Ser Arg Glu
                965                 970                 975

Arg Met Lys Arg Ile Glu Glu Gly Ile Lys Glu Leu Gly Ser Gln Ile
            980                 985                 990

Leu Lys Glu His Pro Val Glu Asn  Thr Gln Leu Gln Asn  Glu Lys Leu
        995                 1000                 1005

Tyr Leu  Tyr Tyr Leu Gln Asn  Gly Arg Asp Met Tyr  Val Asp Gln
    1010                 1015                 1020

Glu Leu  Asp Ile Asn Arg Leu  Ser Asp Tyr Asp Val  Asp Ala Ile
    1025                 1030                 1035

Val Pro  Gln Ser Phe Leu Lys  Asp Asp Ser Ile Asp  Asn Lys Val
    1040                 1045                 1050

Leu Thr  Arg Ser Asp Lys Asn  Arg Gly Lys Ser Asp  Asn Val Pro
    1055                 1060                 1065

Ser Glu  Glu Val Val Lys Lys  Met Lys Asn Tyr Trp  Arg Gln Leu
    1070                 1075                 1080

Leu Asn  Ala Lys Leu Ile Thr  Gln Arg Lys Phe Asp  Asn Leu Thr
    1085                 1090                 1095

Lys Ala  Glu Arg Gly Gly Leu  Ser Glu Leu Asp Lys  Ala Gly Phe
    1100                 1105                 1110

Ile Lys  Arg Gln Leu Val Glu  Thr Arg Gln Ile Thr  Lys His Val
    1115                 1120                 1125

Ala Gln  Ile Leu Asp Ser Arg  Met Asn Thr Lys Tyr  Asp Glu Asn
```

```
    1130                1135                1140

Asp Lys  Leu Ile Arg Glu Val  Lys Val Ile Thr Leu  Lys Ser Lys
    1145                1150                1155

Leu Val  Ser Asp Phe Arg Lys  Asp Phe Gln Phe Tyr  Lys Val Arg
    1160                1165                1170

Glu Ile  Asn Asn Tyr His His  Ala His Asp Ala Tyr  Leu Asn Ala
    1175                1180                1185

Val Val  Gly Thr Ala Leu Ile  Lys Lys Tyr Pro Lys  Leu Glu Ser
    1190                1195                1200

Glu Phe  Val Tyr Gly Asp Tyr  Lys Val Tyr Asp Val  Arg Lys Met
    1205                1210                1215

Ile Ala  Lys Ser Glu Gln Glu  Ile Gly Lys Ala Thr  Ala Lys Tyr
    1220                1225                1230

Phe Phe  Tyr Ser Asn Ile Met  Asn Phe Phe Lys Thr  Glu Ile Thr
    1235                1240                1245

Leu Ala  Asn Gly Glu Ile Arg  Lys Arg Pro Leu Ile  Glu Thr Asn
    1250                1255                1260

Gly Glu  Thr Gly Glu Ile Val  Trp Asp Lys Gly Arg  Asp Phe Ala
    1265                1270                1275

Thr Val  Arg Lys Val Leu Ser  Met Pro Gln Val Asn  Ile Val Lys
    1280                1285                1290

Lys Thr  Glu Val Gln Thr Gly  Gly Phe Ser Lys Glu  Ser Ile Leu
    1295                1300                1305

Pro Lys  Arg Asn Ser Asp Lys  Leu Ile Ala Arg Lys  Lys Asp Trp
    1310                1315                1320

Asp Pro  Lys Lys Tyr Gly Gly  Phe Asp Ser Pro Thr  Val Ala Tyr
    1325                1330                1335

Ser Val  Leu Val Val Ala Lys  Val Glu Lys Gly Lys  Ser Lys Lys
    1340                1345                1350

Leu Lys  Ser Val Lys Glu Leu  Leu Gly Ile Thr Ile  Met Glu Arg
    1355                1360                1365

Ser Ser  Phe Glu Lys Asn Pro  Ile Asp Phe Leu Glu  Ala Lys Gly
    1370                1375                1380

Tyr Lys  Glu Val Lys Lys Asp  Leu Ile Ile Lys Leu  Pro Lys Tyr
    1385                1390                1395

Ser Leu  Phe Glu Leu Glu Asn  Gly Arg Lys Arg Met  Leu Ala Ser
    1400                1405                1410

Ala Gly  Glu Leu Gln Lys Gly  Asn Glu Leu Ala Leu  Pro Ser Lys
    1415                1420                1425

Tyr Val  Asn Phe Leu Tyr Leu  Ala Ser His Tyr Glu  Lys Leu Lys
    1430                1435                1440

Gly Ser  Pro Glu Asp Asn Glu  Gln Lys Gln Leu Phe  Val Glu Gln
    1445                1450                1455

His Lys  His Tyr Leu Asp Glu  Ile Ile Glu Gln Ile  Ser Glu Phe
    1460                1465                1470

Ser Lys  Arg Val Ile Leu Ala  Asp Ala Asn Leu Asp  Lys Val Leu
    1475                1480                1485

Ser Ala  Tyr Asn Lys His Arg  Asp Lys Pro Ile Arg  Glu Gln Ala
    1490                1495                1500

Glu Asn  Ile Ile His Leu Phe  Thr Leu Thr Asn Leu  Gly Ala Pro
    1505                1510                1515

Ala Ala  Phe Lys Tyr Phe Asp  Thr Thr Ile Asp Arg  Lys Arg Tyr
    1520                1525                1530
```

```
Thr Ser  Thr Lys Glu Val Leu  Asp Ala Thr Leu Ile  His Gln Ser
    1535                 1540                 1545

Ile Thr  Gly Leu Tyr Glu Thr  Arg Ile Asp Leu Ser  Gln Leu Gly
    1550                 1555                 1560

Gly Asp  Ser Gly Gly Ser Pro  Lys Lys Lys Arg Lys  Val
    1565                 1570                 1575


<210> SEQ ID NO 30
<211> LENGTH: 4890
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Coding sequence of dCas9-XTEN-AID P182X K10E
      T82I E156G

<400> SEQUENCE: 30

atggactata aggaccacga cggagactac aaggatcatg atattgatta caaagacgat     60

gacgataaga tggccccaaa gaagaagcgg aaggtcggta tccacggagt cccagcagct    120

accatggaca agaagtattc tatcggactg gccatcggga ctaatagcgt cgggtgggcc    180

gtgatcactg acgagtacaa ggtgccctct aagaagttca aggtgctcgg gaacaccgac    240

cggcattcca tcaagaaaaa tctgatcgga gctctcctct ttgattcagg ggagaccgct    300

gaagcaaccc gcctcaagcg gactgctaga cggcggtaca ccaggaggaa gaaccggatt    360

tgttaccttc aagagatatt ctccaacgaa atggcaaagg tcgacgacag cttcttccat    420

aggctggaag aatcattcct cgtggaagag gataagaagc atgaacggca tcccatcttc    480

ggtaatatcg tcgacgaggt ggcctatcac gagaaatacc caaccatcta ccatcttcgc    540

aaaaagctgg tggactcaac cgacaaggca gacctccggc ttatctacct ggccctggcc    600

cacatgatca agttcagagg ccacttcctg atcgagggcg acctcaatcc tgacaatagc    660

gatgtggata aactgttcat ccagctggtg cagacttaca accagctctt tgaagagaac    720

cccatcaatg caagcggagt cgatgccaag gccattctgt cagcccggct gtcaaagagc    780

cgcagacttg agaatcttat cgctcagctg ccgggtgaaa agaaaaatgg actgttcggg    840

aacctgattg ctctttcact tgggctgact cccaatttca agtctaattt cgacctggca    900

gaggatgcca agctgcaact gtccaaggac acctatgatg acgatctcga caacctcctg    960

gcccagatcg gtgaccaata cgccgacctt ttccttgctg ctaagaatct ttctgacgcc   1020

atcctgctgt ctgacattct ccgcgtgaac actgaaatca ccaaggcccc tctttcagct   1080

tcaatgatta agcggtatga tgagcaccac caggacctga ccctgcttaa ggcactcgtc   1140

cggcagcagc ttccggagaa gtacaaggaa atcttctttg accagtcaaa gaatggatac   1200

gccggctaca tcgacggagg tgcctcccaa gaggaatttt ataagtttat caaacctatc   1260

cttgagaaga tggacggcac cgaagagctc ctcgtgaaac tgaatcggga ggatctgctg   1320

cggaagcagc gcactttcga caatgggagc attccccacc agatccatct tggggagctt   1380

cacgccatcc ttcggcgcca agaggacttc taccccttc ttaaggacaa cagggagaag    1440

attgagaaaa ttctcacttt ccgcatcccc tactacgtgg gacccctcgc cagaggaaat   1500

agccggtttg cttggatgac cagaaagtca gaagaaacta tcactccctg gaacttcgaa   1560

gaggtggtgg acaagggagc cagcgctcag tcattcatcg aacggatgac taacttcgat   1620

aagaacctcc ccaatgagaa ggtcctgccg aaacattccc tgctctacga gtactttacc   1680
```

-continued

```
gtgtacaacg agctgaccaa ggtgaaatat gtcaccgaag ggatgaggaa gcccgcattc   1740
ctgtcaggcg aacaaaagaa ggcaattgtg gaccttctgt tcaagaccaa tagaaaggtg   1800
accgtgaagc agctgaagga ggactatttc aagaaaattg aatgcttcga ctctgtggag   1860
attagcgggg tcgaagatcg gttcaacgca agcctgggta cctaccatga tctgcttaag   1920
atcatcaagg acaaggattt tctggacaat gaggagaaag aggacatcct tgaggacatt   1980
gtcctgactc tcactctgtt cgaggaccgg gaaatgatcg aggagaggct taagacctac   2040
gcccatctgt tcgacgataa agtgatgaag caacttaaac ggagaagata taccggatgg   2100
ggacgcctta gccgcaaact catcaacgga atccgggaca aacagagcgg aaagaccatt   2160
cttgatttcc ttaagagcga cggattcgct aatcgcaact tcatgcaact tatccatgat   2220
gattccctga cctttaagga ggacatccag aaggcccaag tgtctggaca aggtgactca   2280
ctgcacgagc atatcgcaaa tctggctggt tcacccgcta ttaagaaggg tattctccag   2340
accgtgaaag tcgtggacga gctggtcaag gtgatgggtc gccataaacc agagaacatt   2400
gtcatcgaga tggccaggga aaaccagact acccagaagg gacagaagaa cagcagggag   2460
cggatgaaaa gaattgagga agggattaag gagctcgggt cacagatcct taaagagcac   2520
ccggtggaaa acacccagct tcagaatgag aagctctatc tgtactacct tcaaaatgga   2580
cgcgatatgt atgtggacca agagcttgat atcaacaggc tctcagacta cgacgtggac   2640
gccatcgtcc ctcagagctt cctcaaagac gactcaattg acaataaggt gctgactcgc   2700
tcagacaaga accggggaaa gtcagataac gtgccctcag aggaagtcgt gaaaaagatg   2760
aagaactatt ggcgccagct tctgaacgca aagctgatca ctcagcggaa gttcgacaat   2820
ctcactaagg ctgagagggg cggactgagc gaactggaca aagcaggatt cattaaacgg   2880
caacttgtgg agactcggca gattactaaa catgtagccc aaatccttga ctcacgcatg   2940
aataccaagt acgacgaaaa cgacaaactt atccgcgagg tgaaggtgat taccctgaag   3000
tccaagctgg tcagcgattt cagaaaggac tttcaattct acaaagtgcg ggagatcaat   3060
aactatcatc atgctcatga cgcatatctg aatgccgtgg tgggaaccgc cctgatcaag   3120
aagtacccaa agctggaaag cgagttcgtg tacggagact acaaggtcta cgacgtgcgc   3180
aagatgattg ccaaatctga gcaggagatc ggaaaggcca ccgcaaagta cttcttctac   3240
agcaacatca tgaatttctt caagaccgaa atcacccttg caaacggtga gatccggaag   3300
aggccgctca tcgagactaa tggggagact ggcgaaatcg tgtgggacaa gggcagagat   3360
ttcgctaccg tgcgcaaagt gctttctatg cctcaagtga acatcgtgaa gaaaaccgag   3420
gtgcaaaccg gaggcttttc taaggaatca atcctcccca agcgcaactc cgacaagctc   3480
attgcaagga agaaggattg ggaccctaag aagtacggcg gattcgattc accaactgtg   3540
gcttattctg tcctggtcgt ggctaaggtg gaaaaaggaa agtctaagaa gctcaagagc   3600
gtgaaggaac tgctgggtat caccattatg gagcgcagct ccttcgagaa gaacccaatt   3660
gactttctcg aagccaaagg ttacaaggaa gtcaagaagg accttatcat caagctccca   3720
aagtatagcc tgttcgaact ggagaatggg cggaagcgga tgctcgcctc cgctggcgaa   3780
cttcagaagg gtaatgagct ggctctcccc tccaagtacg tgaatttcct ctaccttgca   3840
agccattacg agaagctgaa ggggagcccc gaggacaacg agcaaaagca actgtttgtg   3900
gagcagcata agcattatct ggacgagatc attgagcaga tttccgagtt ttctaaacgc   3960
gtcattctcg ctgatgccaa cctcgataaa gtccttagcg catacaataa gcacagagac   4020
```

```
aaaccaattc gggagcaggc tgagaatatc atccacctgt tcaccctcac caatcttggt   4080

gcccctgccg cattcaagta cttcgacacc accatcgacc ggaaacgcta tacctccacc   4140

aaagaagtgc tggacgccac cctcatccac cagagcatca ccggacttta cgaaactcgg   4200

attgacctct cacagctcgg aggggatgag ggagctccca agaaaaagcg caaggtaggt   4260

agttccggat ctccgaaaaa gaaacgcaaa gttagcggca gcgagactcc cgggacctca   4320

gagtccgcca cacccgaaag tatggacagc ctcttgatga accggaggga gtttctttac   4380

caattcaaaa atgtccgctg ggctaagggt cggcgtgaga cctacctgtg ctacgtagtg   4440

aagaggcgtg acagtgctac atccttttca ctggactttg gttatcttcg caataagaac   4500

ggctgccacg tggaattgct cttcctccgc tacatctcgg actgggacct agaccctggc   4560

cgctgctacc gcgtcacctg gttcatctcc tggagcccct gctacgactg tgcccgacat   4620

gtggccgact ttctgcgagg gaaccccaac ctcagtctga ggatcttcac cgcgcgcctc   4680

tacttctgtg aggaccgcaa ggctgagccc gaggggctgc ggcggctgca ccgcgccggg   4740

gtgcaaatag ccatcatgac cttcaaagat tatttttact gctggaatac ttttgtagaa   4800

aaccatggaa gaactttcaa agcctgggaa gggctgcatg aaaattcagt tcgtctctcc   4860

agacagcttc ggcgcatcct tttgccctga                                    4890


<210> SEQ ID NO 31
<211> LENGTH: 1629
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Amino acid sequence of dCas9-XTEN-AID P182X
      K10E T82I E156G

<400> SEQUENCE: 31

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Ile His Gly Val Pro Ala Ala Thr Met Asp Lys Lys Tyr Ser Ile
        35                  40                  45

Gly Leu Ala Ile Gly Thr Asn Ser Val Gly Trp Ala Val Ile Thr Asp
    50                  55                  60

Glu Tyr Lys Val Pro Ser Lys Lys Phe Lys Val Leu Gly Asn Thr Asp
65                  70                  75                  80

Arg His Ser Ile Lys Lys Asn Leu Ile Gly Ala Leu Leu Phe Asp Ser
                85                  90                  95

Gly Glu Thr Ala Glu Ala Thr Arg Leu Lys Arg Thr Ala Arg Arg Arg
            100                 105                 110

Tyr Thr Arg Arg Lys Asn Arg Ile Cys Tyr Leu Gln Glu Ile Phe Ser
        115                 120                 125

Asn Glu Met Ala Lys Val Asp Asp Ser Phe Phe His Arg Leu Glu Glu
    130                 135                 140

Ser Phe Leu Val Glu Glu Asp Lys Lys His Glu Arg His Pro Ile Phe
145                 150                 155                 160

Gly Asn Ile Val Asp Glu Val Ala Tyr His Glu Lys Tyr Pro Thr Ile
                165                 170                 175

Tyr His Leu Arg Lys Lys Leu Val Asp Ser Thr Asp Lys Ala Asp Leu
            180                 185                 190
```

```
Arg Leu Ile Tyr Leu Ala Leu Ala His Met Ile Lys Phe Arg Gly His
        195                 200                 205

Phe Leu Ile Glu Gly Asp Leu Asn Pro Asp Asn Ser Asp Val Asp Lys
    210                 215                 220

Leu Phe Ile Gln Leu Val Gln Thr Tyr Asn Gln Leu Phe Glu Glu Asn
225                 230                 235                 240

Pro Ile Asn Ala Ser Gly Val Asp Ala Lys Ala Ile Leu Ser Ala Arg
                245                 250                 255

Leu Ser Lys Ser Arg Arg Leu Glu Asn Leu Ile Ala Gln Leu Pro Gly
            260                 265                 270

Glu Lys Lys Asn Gly Leu Phe Gly Asn Leu Ile Ala Leu Ser Leu Gly
        275                 280                 285

Leu Thr Pro Asn Phe Lys Ser Asn Phe Asp Leu Ala Glu Asp Ala Lys
    290                 295                 300

Leu Gln Leu Ser Lys Asp Thr Tyr Asp Asp Asp Leu Asp Asn Leu Leu
305                 310                 315                 320

Ala Gln Ile Gly Asp Gln Tyr Ala Asp Leu Phe Leu Ala Ala Lys Asn
                325                 330                 335

Leu Ser Asp Ala Ile Leu Leu Ser Asp Ile Leu Arg Val Asn Thr Glu
            340                 345                 350

Ile Thr Lys Ala Pro Leu Ser Ala Ser Met Ile Lys Arg Tyr Asp Glu
        355                 360                 365

His His Gln Asp Leu Thr Leu Leu Lys Ala Leu Val Arg Gln Gln Leu
    370                 375                 380

Pro Glu Lys Tyr Lys Glu Ile Phe Phe Asp Gln Ser Lys Asn Gly Tyr
385                 390                 395                 400

Ala Gly Tyr Ile Asp Gly Gly Ala Ser Gln Glu Glu Phe Tyr Lys Phe
                405                 410                 415

Ile Lys Pro Ile Leu Glu Lys Met Asp Gly Thr Glu Glu Leu Leu Val
            420                 425                 430

Lys Leu Asn Arg Glu Asp Leu Leu Arg Lys Gln Arg Thr Phe Asp Asn
        435                 440                 445

Gly Ser Ile Pro His Gln Ile His Leu Gly Glu Leu His Ala Ile Leu
    450                 455                 460

Arg Arg Gln Glu Asp Phe Tyr Pro Phe Leu Lys Asp Asn Arg Glu Lys
465                 470                 475                 480

Ile Glu Lys Ile Leu Thr Phe Arg Ile Pro Tyr Tyr Val Gly Pro Leu
                485                 490                 495

Ala Arg Gly Asn Ser Arg Phe Ala Trp Met Thr Arg Lys Ser Glu Glu
            500                 505                 510

Thr Ile Thr Pro Trp Asn Phe Glu Glu Val Val Asp Lys Gly Ala Ser
        515                 520                 525

Ala Gln Ser Phe Ile Glu Arg Met Thr Asn Phe Asp Lys Asn Leu Pro
    530                 535                 540

Asn Glu Lys Val Leu Pro Lys His Ser Leu Leu Tyr Glu Tyr Phe Thr
545                 550                 555                 560

Val Tyr Asn Glu Leu Thr Lys Val Lys Tyr Val Thr Glu Gly Met Arg
                565                 570                 575

Lys Pro Ala Phe Leu Ser Gly Glu Gln Lys Lys Ala Ile Val Asp Leu
            580                 585                 590

Leu Phe Lys Thr Asn Arg Lys Val Thr Val Lys Gln Leu Lys Glu Asp
        595                 600                 605
```

-continued

```
Tyr Phe Lys Lys Ile Glu Cys Phe Asp Ser Val Glu Ile Ser Gly Val
    610                 615                 620

Glu Asp Arg Phe Asn Ala Ser Leu Gly Thr Tyr His Asp Leu Leu Lys
625                 630                 635                 640

Ile Ile Lys Asp Lys Asp Phe Leu Asp Asn Glu Glu Lys Glu Asp Ile
                645                 650                 655

Leu Glu Asp Ile Val Leu Thr Leu Thr Leu Phe Glu Asp Arg Glu Met
            660                 665                 670

Ile Glu Glu Arg Leu Lys Thr Tyr Ala His Leu Phe Asp Asp Lys Val
        675                 680                 685

Met Lys Gln Leu Lys Arg Arg Arg Tyr Thr Gly Trp Gly Arg Leu Ser
    690                 695                 700

Arg Lys Leu Ile Asn Gly Ile Arg Asp Lys Gln Ser Gly Lys Thr Ile
705                 710                 715                 720

Leu Asp Phe Leu Lys Ser Asp Gly Phe Ala Asn Arg Asn Phe Met Gln
                725                 730                 735

Leu Ile His Asp Asp Ser Leu Thr Phe Lys Glu Asp Ile Gln Lys Ala
            740                 745                 750

Gln Val Ser Gly Gln Gly Asp Ser Leu His Glu His Ile Ala Asn Leu
        755                 760                 765

Ala Gly Ser Pro Ala Ile Lys Lys Gly Ile Leu Gln Thr Val Lys Val
    770                 775                 780

Val Asp Glu Leu Val Lys Val Met Gly Arg His Lys Pro Glu Asn Ile
785                 790                 795                 800

Val Ile Glu Met Ala Arg Glu Asn Gln Thr Thr Gln Lys Gly Gln Lys
                805                 810                 815

Asn Ser Arg Glu Arg Met Lys Arg Ile Glu Glu Gly Ile Lys Glu Leu
            820                 825                 830

Gly Ser Gln Ile Leu Lys Glu His Pro Val Glu Asn Thr Gln Leu Gln
        835                 840                 845

Asn Glu Lys Leu Tyr Leu Tyr Tyr Leu Gln Asn Gly Arg Asp Met Tyr
    850                 855                 860

Val Asp Gln Glu Leu Asp Ile Asn Arg Leu Ser Asp Tyr Asp Val Asp
865                 870                 875                 880

Ala Ile Val Pro Gln Ser Phe Leu Lys Asp Asp Ser Ile Asp Asn Lys
                885                 890                 895

Val Leu Thr Arg Ser Asp Lys Asn Arg Gly Lys Ser Asp Asn Val Pro
            900                 905                 910

Ser Glu Glu Val Val Lys Lys Met Lys Asn Tyr Trp Arg Gln Leu Leu
        915                 920                 925

Asn Ala Lys Leu Ile Thr Gln Arg Lys Phe Asp Asn Leu Thr Lys Ala
    930                 935                 940

Glu Arg Gly Gly Leu Ser Glu Leu Asp Lys Ala Gly Phe Ile Lys Arg
945                 950                 955                 960

Gln Leu Val Glu Thr Arg Gln Ile Thr Lys His Val Ala Gln Ile Leu
                965                 970                 975

Asp Ser Arg Met Asn Thr Lys Tyr Asp Glu Asn Asp Lys Leu Ile Arg
            980                 985                 990

Glu Val Lys Val Ile Thr Leu Lys  Ser Lys Leu Val Ser  Asp Phe Arg
        995                 1000                1005

Lys Asp  Phe Gln Phe Tyr Lys  Val Arg Glu Ile Asn  Asn Tyr His
    1010                1015                1020

His Ala  His Asp Ala Tyr Leu  Asn Ala Val Val Gly  Thr Ala Leu
```

```
    1025                1030                1035

Ile Lys  Lys Tyr Pro Lys Leu  Glu Ser Glu Phe Val  Tyr Gly Asp
    1040                1045                1050

Tyr Lys  Val Tyr Asp Val Arg  Lys Met Ile Ala Lys  Ser Glu Gln
    1055                1060                1065

Glu Ile  Gly Lys Ala Thr Ala  Lys Tyr Phe Phe Tyr  Ser Asn Ile
    1070                1075                1080

Met Asn  Phe Phe Lys Thr Glu  Ile Thr Leu Ala Asn  Gly Glu Ile
    1085                1090                1095

Arg Lys  Arg Pro Leu Ile Glu  Thr Asn Gly Glu Thr  Gly Glu Ile
    1100                1105                1110

Val Trp  Asp Lys Gly Arg Asp  Phe Ala Thr Val Arg  Lys Val Leu
    1115                1120                1125

Ser Met  Pro Gln Val Asn Ile  Val Lys Lys Thr Glu  Val Gln Thr
    1130                1135                1140

Gly Gly  Phe Ser Lys Glu Ser  Ile Leu Pro Lys Arg  Asn Ser Asp
    1145                1150                1155

Lys Leu  Ile Ala Arg Lys Lys  Asp Trp Asp Pro Lys  Lys Tyr Gly
    1160                1165                1170

Gly Phe  Asp Ser Pro Thr Val  Ala Tyr Ser Val Leu  Val Val Ala
    1175                1180                1185

Lys Val  Glu Lys Gly Lys Ser  Lys Lys Leu Lys Ser  Val Lys Glu
    1190                1195                1200

Leu Leu  Gly Ile Thr Ile Met  Glu Arg Ser Ser Phe  Glu Lys Asn
    1205                1210                1215

Pro Ile  Asp Phe Leu Glu Ala  Lys Gly Tyr Lys Glu  Val Lys Lys
    1220                1225                1230

Asp Leu  Ile Ile Lys Leu Pro  Lys Tyr Ser Leu Phe  Glu Leu Glu
    1235                1240                1245

Asn Gly  Arg Lys Arg Met Leu  Ala Ser Ala Gly Glu  Leu Gln Lys
    1250                1255                1260

Gly Asn  Glu Leu Ala Leu Pro  Ser Lys Tyr Val Asn  Phe Leu Tyr
    1265                1270                1275

Leu Ala  Ser His Tyr Glu Lys  Leu Lys Gly Ser Pro  Glu Asp Asn
    1280                1285                1290

Glu Gln  Lys Gln Leu Phe Val  Glu Gln His Lys His  Tyr Leu Asp
    1295                1300                1305

Glu Ile  Ile Glu Gln Ile Ser  Glu Phe Ser Lys Arg  Val Ile Leu
    1310                1315                1320

Ala Asp  Ala Asn Leu Asp Lys  Val Leu Ser Ala Tyr  Asn Lys His
    1325                1330                1335

Arg Asp  Lys Pro Ile Arg Glu  Gln Ala Glu Asn Ile  Ile His Leu
    1340                1345                1350

Phe Thr  Leu Thr Asn Leu Gly  Ala Pro Ala Ala Phe  Lys Tyr Phe
    1355                1360                1365

Asp Thr  Thr Ile Asp Arg Lys  Arg Tyr Thr Ser Thr  Lys Glu Val
    1370                1375                1380

Leu Asp  Ala Thr Leu Ile His  Gln Ser Ile Thr Gly  Leu Tyr Glu
    1385                1390                1395

Thr Arg  Ile Asp Leu Ser Gln  Leu Gly Gly Asp Glu  Gly Ala Pro
    1400                1405                1410

Lys Lys  Lys Arg Lys Val Gly  Ser Ser Gly Ser Pro  Lys Lys Lys
    1415                1420                1425
```

Arg Lys Val Ser Gly Ser Glu Thr Pro Gly Thr Ser Glu Ser Ala
1430 1435 1440

Thr Pro Glu Ser Met Asp Ser Leu Leu Met Asn Arg Arg Glu Phe
1445 1450 1455

Leu Tyr Gln Phe Lys Asn Val Arg Trp Ala Lys Gly Arg Arg Glu
1460 1465 1470

Thr Tyr Leu Cys Tyr Val Val Lys Arg Arg Asp Ser Ala Thr Ser
1475 1480 1485

Phe Ser Leu Asp Phe Gly Tyr Leu Arg Asn Lys Asn Gly Cys His
1490 1495 1500

Val Glu Leu Leu Phe Leu Arg Tyr Ile Ser Asp Trp Asp Leu Asp
1505 1510 1515

Pro Gly Arg Cys Tyr Arg Val Thr Trp Phe Ile Ser Trp Ser Pro
1520 1525 1530

Cys Tyr Asp Cys Ala Arg His Val Ala Asp Phe Leu Arg Gly Asn
1535 1540 1545

Pro Asn Leu Ser Leu Arg Ile Phe Thr Ala Arg Leu Tyr Phe Cys
1550 1555 1560

Glu Asp Arg Lys Ala Glu Pro Glu Gly Leu Arg Arg Leu His Arg
1565 1570 1575

Ala Gly Val Gln Ile Ala Ile Met Thr Phe Lys Asp Tyr Phe Tyr
1580 1585 1590

Cys Trp Asn Thr Phe Val Glu Asn His Gly Arg Thr Phe Lys Ala
1595 1600 1605

Trp Glu Gly Leu His Glu Asn Ser Val Arg Leu Ser Arg Gln Leu
1610 1615 1620

Arg Arg Ile Leu Leu Pro
1625

<210> SEQ ID NO 32
<211> LENGTH: 4917
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Coding sequence of ncas9-P182x

<400> SEQUENCE: 32
atggactata aggaccacga cggagactac aaggatcatg atattgatta caaagacgat 60
gacgataaga tggccccaaa gaagaagcgg aaggtcggta tccacggagt cccagcagct 120
accatggaca agaagtattc tatcggactg gccatcggga ctaatagcgt cgggtgggcc 180
gtgatcactg acgagtacaa ggtgccctct aagaagttca aggtgctcgg gaacaccgac 240
cggcattcca tcaagaaaaa tctgatcgga gctctcctct ttgattcagg ggagaccgct 300
gaagcaaccc gcctcaagcg gactgctaga cggcggtaca ccaggaggaa gaaccggatt 360
tgttaccttc aagagatatt ctccaacgaa atggcaaagg tcgacgacag cttcttccat 420
aggctggaag aatcattcct cgtggaagag gataagaagc atgaacggca tcccatcttc 480
ggtaatatcg tcgacgaggt ggcctatcac gagaaatacc caaccatcta ccatcttcgc 540
aaaaagctgg tggactcaac cgacaaggca gacctccggc ttatctacct ggccctggcc 600
cacatgatca agttcagagg ccacttcctg atcgagggcg acctcaatcc tgacaatagc 660
gatgtggata aactgttcat ccagctggtg cagacttaca accagctctt tgaagagaac 720

-continued

```
cccatcaatg caagcggagt cgatgccaag gccattctgt cagcccggct gtcaaagagc     780
cgcagacttg agaatcttat cgctcagctg ccgggtgaaa agaaaaatgg actgttcggg     840
aacctgattg ctctttcact tggcctgact cccaatttca agtctaattt cgacctggca     900
gaggatgcca agctgcaact gtccaaggac acctatgatg acgatctcga caacctcctg     960
gcccagatcg gtgaccaata cgccgacctt ttccttgctg ctaagaatct ttctgacgcc    1020
atcctgctgt ctgacattct ccgcgtgaac actgaaatca ccaaggcccc tctttcagct    1080
tcaatgatta agcggtatga tgagcaccac caggacctga ccctgcttaa ggcactcgtc    1140
cggcagcagc ttccggagaa gtacaaggaa atcttctttg accagtcaaa gaatggatac    1200
gccggctaca tcgacggagg tgcctcccaa gaggaatttt ataagtttat caaacctatc    1260
cttgagaaga tggacggcac cgaagagctc ctcgtgaaac tgaatcggga ggatctgctg    1320
cggaagcagc gcactttcga caatgggagc attccccacc agatccatct tggggagctt    1380
cacgccatcc ttcggcgcca agaggacttc taccccttc ttaaggacaa cagggagaag    1440
attgagaaaa ttctcacttt ccgcatcccc tactacgtgg gacccctcgc cagaggaaat    1500
agccggtttg cttggatgac cagaaagtca gaagaaacta tcactccctg gaacttcgaa    1560
gaggtggtgg acaagggagc cagcgctcag tcattcatcg aacggatgac taacttcgat    1620
aagaacctcc ccaatgagaa ggtcctgccg aaacattccc tgctctacga gtactttacc    1680
gtgtacaacg agctgaccaa ggtgaaatat gtcaccgaag ggatgaggaa gcccgcattc    1740
ctgtcaggcg aacaaaagaa ggcaattgtg gaccttctgt tcaagaccaa tagaaaggtg    1800
accgtgaagc agctgaagga ggactatttc aagaaaattg aatgcttcga ctctgtggag    1860
attagcgggg tcgaagatcg gttcaacgca agcctgggta cctaccatga tctgcttaag    1920
atcatcaagg acaaggattt tctggacaat gaggagaaag aggacatcct tgaggacatt    1980
gtcctgactc tcactctgtt cgaggaccgg gaaatgatcg aggagaggct taagacctac    2040
gcccatctgt tcgacgataa agtgatgaag caacttaaac ggagaagata taccggatgg    2100
ggacgcctta gccgcaaact catcaacgga atccgggaca aacagagcgg aaagaccatt    2160
cttgatttcc ttaagagcga cggattcgct aatcgcaact tcatgcaact tatccatgat    2220
gattccctga cctttaagga ggacatccag aaggcccaag tgtctggaca aggtgactca    2280
ctgcacgagc atatcgcaaa tctggctggt tcacccgcta ttaagaaggg tattctccag    2340
accgtgaaag tcgtggacga gctggtcaag gtgatgggtc gccataaacc agagaacatt    2400
gtcatcgaga tggccaggga aaaccagact acccagaagg gacagaagaa cagcagggag    2460
cggatgaaaa gaattgagga agggattaag gagctcgggt cacagatcct taaagagcac    2520
ccggtggaaa acacccagct tcagaatgag aagctctatc tgtactacct tcaaaatgga    2580
cgcgatatgt atgtggacca agagcttgat atcaacaggc tctcagacta cgacgtggac    2640
catatcgtcc ctcagagctt cctcaaagac gactcaattg acaataaggt gctgactcgc    2700
tcagacaaga accggggaaa gtcagataac gtgccctcag aggaagtcgt gaaaaagatg    2760
aagaactatt ggcgccagct tctgaacgca aagctgatca ctcagcggaa gttcgacaat    2820
ctcactaagg ctgagagggg cggactgagc gaactggaca aagcaggatt cattaaacgg    2880
caacttgtgg agactcggca gattactaaa catgtagccc aaatccttga ctcacgcatg    2940
aataccaagt acgacgaaaa cgacaaactt atccgcgagg tgaaggtgat taccctgaag    3000
tccaagctgg tcagcgattt cagaaaggac tttcaattct acaaagtgcg ggagatcaat    3060
```

```
aactatcatc atgctcatga cgcatatctg aatgccgtgg tgggaaccgc cctgatcaag   3120

aagtacccaa agctggaaag cgagttcgtg tacggagact acaaggtcta cgacgtgcgc   3180

aagatgattg ccaaatctga gcaggagatc ggaaaggcca ccgcaaagta cttcttctac   3240

agcaacatca tgaatttctt caagaccgaa atcacccttg caaacggtga gatccggaag   3300

aggccgctca tcgagactaa tggggagact ggcgaaatcg tgtgggacaa gggcagagat   3360

ttcgctaccg tgcgcaaagt gctttctatg cctcaagtga acatcgtgaa gaaaaccgag   3420

gtgcaaaccg gaggcttttc taaggaatca atcctcccca agcgcaactc cgacaagctc   3480

attgcaagga agaaggattg ggaccctaag aagtacggcg gattcgattc accaactgtg   3540

gcttattctg tcctggtcgt ggctaaggtg gaaaaaggaa agtctaagaa gctcaagagc   3600

gtgaaggaac tgctgggtat caccattatg gagcgcagct ccttcgagaa gaacccaatt   3660

gactttctcg aagccaaagg ttacaaggaa gtcaagaagg accttatcat caagctccca   3720

aagtatagcc tgttcgaact ggagaatggg cggaagcgga tgctcgcctc cgctggcgaa   3780

cttcagaagg gtaatgagct ggctctcccc tccaagtacg tgaatttcct ctaccttgca   3840

agccattacg agaagctgaa ggggagcccc gaggacaacg agcaaaagca actgtttgtg   3900

gagcagcata agcattatct ggacgagatc attgagcaga tttccgagtt ttctaaacgc   3960

gtcattctcg ctgatgccaa cctcgataaa gtccttagcg catacaataa gcacagagac   4020

aaaccaattc gggagcaggc tgagaatatc atccacctgt tcaccctcac caatcttggt   4080

gcccctgccg cattcaagta cttcgacacc accatcgacc ggaaacgcta tacctccacc   4140

aaagaagtgc tggacgccac cctcatccac cagagcatca ccggacttta cgaaactcgg   4200

attgacctct cacagctcgg aggggatgag ggagctccca agaaaaagcg caaggtaggt   4260

agttccggat ctccgaaaaa gaaacgcaaa gttggtagtg atgctttaga cgattttgac   4320

ttagatatgc ttggttcaga cgcgttagac gacttcggtg gaggatccat ggacagcctc   4380

ttgatgaacc ggaggaagtt tctttaccaa ttcaaaaatg tccgctgggc taagggtcgg   4440

cgtgagacct acctgtgcta cgtagtgaag aggcgtgaca gtgctacatc cttttcactg   4500

gactttggtt atcttcgcaa taagaacggc tgccacgtgg aattgctctt cctccgctac   4560

atctcggact gggacctaga ccctggccgc tgctaccgcg tcacctggtt cacctcctgg   4620

agcccctgct acgactgtgc ccgacatgtg gccgactttc tgcgagggaa ccccaacctc   4680

agtctgagga tcttcaccgc gcgcctctac ttctgtgagg accgcaaggc tgagcccgag   4740

gggctgcggc ggctgcaccg cgccggggtg caaatagcca tcatgacctt caaagattat   4800

ttttactgct ggaatacttt tgtagaaaac catgaaagaa ctttcaaagc ctgggaaggg   4860

ctgcatgaaa attcagttcg tctctccaga cagcttcggc gcatcctttt gccctga      4917
```

<210> SEQ ID NO 33
<211> LENGTH: 1638
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Amino acid sequence of ncas9-P182x

<400> SEQUENCE: 33

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
```

```
            20                  25                  30

Gly Ile His Gly Val Pro Ala Ala Thr Met Asp Lys Lys Tyr Ser Ile
        35                  40                  45

Gly Leu Ala Ile Gly Thr Asn Ser Val Gly Trp Ala Val Ile Thr Asp
    50                  55                  60

Glu Tyr Lys Val Pro Ser Lys Lys Phe Lys Val Leu Gly Asn Thr Asp
65                  70                  75                  80

Arg His Ser Ile Lys Lys Asn Leu Ile Gly Ala Leu Leu Phe Asp Ser
                85                  90                  95

Gly Glu Thr Ala Glu Ala Thr Arg Leu Lys Arg Thr Ala Arg Arg Arg
            100                 105                 110

Tyr Thr Arg Arg Lys Asn Arg Ile Cys Tyr Leu Gln Glu Ile Phe Ser
        115                 120                 125

Asn Glu Met Ala Lys Val Asp Asp Ser Phe Phe His Arg Leu Glu Glu
    130                 135                 140

Ser Phe Leu Val Glu Glu Asp Lys Lys His Glu Arg His Pro Ile Phe
145                 150                 155                 160

Gly Asn Ile Val Asp Glu Val Ala Tyr His Glu Lys Tyr Pro Thr Ile
                165                 170                 175

Tyr His Leu Arg Lys Lys Leu Val Asp Ser Thr Asp Lys Ala Asp Leu
            180                 185                 190

Arg Leu Ile Tyr Leu Ala Leu Ala His Met Ile Lys Phe Arg Gly His
        195                 200                 205

Phe Leu Ile Glu Gly Asp Leu Asn Pro Asp Asn Ser Asp Val Asp Lys
    210                 215                 220

Leu Phe Ile Gln Leu Val Gln Thr Tyr Asn Gln Leu Phe Glu Glu Asn
225                 230                 235                 240

Pro Ile Asn Ala Ser Gly Val Asp Ala Lys Ala Ile Leu Ser Ala Arg
                245                 250                 255

Leu Ser Lys Ser Arg Arg Leu Glu Asn Leu Ile Ala Gln Leu Pro Gly
            260                 265                 270

Glu Lys Lys Asn Gly Leu Phe Gly Asn Leu Ile Ala Leu Ser Leu Gly
        275                 280                 285

Leu Thr Pro Asn Phe Lys Ser Asn Phe Asp Leu Ala Glu Asp Ala Lys
    290                 295                 300

Leu Gln Leu Ser Lys Asp Thr Tyr Asp Asp Asp Leu Asp Asn Leu Leu
305                 310                 315                 320

Ala Gln Ile Gly Asp Gln Tyr Ala Asp Leu Phe Leu Ala Ala Lys Asn
                325                 330                 335

Leu Ser Asp Ala Ile Leu Leu Ser Asp Ile Leu Arg Val Asn Thr Glu
            340                 345                 350

Ile Thr Lys Ala Pro Leu Ser Ala Ser Met Ile Lys Arg Tyr Asp Glu
        355                 360                 365

His His Gln Asp Leu Thr Leu Leu Lys Ala Leu Val Arg Gln Gln Leu
    370                 375                 380

Pro Glu Lys Tyr Lys Glu Ile Phe Phe Asp Gln Ser Lys Asn Gly Tyr
385                 390                 395                 400

Ala Gly Tyr Ile Asp Gly Gly Ala Ser Gln Glu Glu Phe Tyr Lys Phe
                405                 410                 415

Ile Lys Pro Ile Leu Glu Lys Met Asp Gly Thr Glu Glu Leu Leu Val
            420                 425                 430

Lys Leu Asn Arg Glu Asp Leu Leu Arg Lys Gln Arg Thr Phe Asp Asn
        435                 440                 445
```

```
Gly Ser Ile Pro His Gln Ile His Leu Gly Glu Leu His Ala Ile Leu
    450                 455                 460

Arg Arg Gln Glu Asp Phe Tyr Pro Phe Leu Lys Asp Asn Arg Glu Lys
465                 470                 475                 480

Ile Glu Lys Ile Leu Thr Phe Arg Ile Pro Tyr Tyr Val Gly Pro Leu
                485                 490                 495

Ala Arg Gly Asn Ser Arg Phe Ala Trp Met Thr Arg Lys Ser Glu Glu
            500                 505                 510

Thr Ile Thr Pro Trp Asn Phe Glu Glu Val Val Asp Lys Gly Ala Ser
        515                 520                 525

Ala Gln Ser Phe Ile Glu Arg Met Thr Asn Phe Asp Lys Asn Leu Pro
    530                 535                 540

Asn Glu Lys Val Leu Pro Lys His Ser Leu Leu Tyr Glu Tyr Phe Thr
545                 550                 555                 560

Val Tyr Asn Glu Leu Thr Lys Val Lys Tyr Val Thr Glu Gly Met Arg
                565                 570                 575

Lys Pro Ala Phe Leu Ser Gly Glu Gln Lys Lys Ala Ile Val Asp Leu
            580                 585                 590

Leu Phe Lys Thr Asn Arg Lys Val Thr Val Lys Gln Leu Lys Glu Asp
        595                 600                 605

Tyr Phe Lys Lys Ile Glu Cys Phe Asp Ser Val Glu Ile Ser Gly Val
    610                 615                 620

Glu Asp Arg Phe Asn Ala Ser Leu Gly Thr Tyr His Asp Leu Leu Lys
625                 630                 635                 640

Ile Ile Lys Asp Lys Asp Phe Leu Asp Asn Glu Glu Lys Glu Asp Ile
                645                 650                 655

Leu Glu Asp Ile Val Leu Thr Leu Thr Leu Phe Glu Asp Arg Glu Met
            660                 665                 670

Ile Glu Glu Arg Leu Lys Thr Tyr Ala His Leu Phe Asp Asp Lys Val
        675                 680                 685

Met Lys Gln Leu Lys Arg Arg Arg Tyr Thr Gly Trp Gly Arg Leu Ser
    690                 695                 700

Arg Lys Leu Ile Asn Gly Ile Arg Asp Lys Gln Ser Gly Lys Thr Ile
705                 710                 715                 720

Leu Asp Phe Leu Lys Ser Asp Gly Phe Ala Asn Arg Asn Phe Met Gln
                725                 730                 735

Leu Ile His Asp Asp Ser Leu Thr Phe Lys Glu Asp Ile Gln Lys Ala
            740                 745                 750

Gln Val Ser Gly Gln Gly Asp Ser Leu His Glu His Ile Ala Asn Leu
        755                 760                 765

Ala Gly Ser Pro Ala Ile Lys Lys Gly Ile Leu Gln Thr Val Lys Val
    770                 775                 780

Val Asp Glu Leu Val Lys Val Met Gly Arg His Lys Pro Glu Asn Ile
785                 790                 795                 800

Val Ile Glu Met Ala Arg Glu Asn Gln Thr Thr Gln Lys Gly Gln Lys
                805                 810                 815

Asn Ser Arg Glu Arg Met Lys Arg Ile Glu Glu Gly Ile Lys Glu Leu
            820                 825                 830

Gly Ser Gln Ile Leu Lys Glu His Pro Val Glu Asn Thr Gln Leu Gln
        835                 840                 845

Asn Glu Lys Leu Tyr Leu Tyr Tyr Leu Gln Asn Gly Arg Asp Met Tyr
    850                 855                 860
```

-continued

```
Val Asp Gln Glu Leu Asp Ile Asn Arg Leu Ser Asp Tyr Asp Val Asp
865                 870                 875                 880

His Ile Val Pro Gln Ser Phe Leu Lys Asp Asp Ser Ile Asp Asn Lys
                885                 890                 895

Val Leu Thr Arg Ser Asp Lys Asn Arg Gly Lys Ser Asp Asn Val Pro
            900                 905                 910

Ser Glu Glu Val Val Lys Lys Met Lys Asn Tyr Trp Arg Gln Leu Leu
        915                 920                 925

Asn Ala Lys Leu Ile Thr Gln Arg Lys Phe Asp Asn Leu Thr Lys Ala
    930                 935                 940

Glu Arg Gly Gly Leu Ser Glu Leu Asp Lys Ala Gly Phe Ile Lys Arg
945                 950                 955                 960

Gln Leu Val Glu Thr Arg Gln Ile Thr Lys His Val Ala Gln Ile Leu
                965                 970                 975

Asp Ser Arg Met Asn Thr Lys Tyr Asp Glu Asn Asp Lys Leu Ile Arg
            980                 985                 990

Glu Val Lys Val Ile Thr Leu Lys  Ser Lys Leu Val Ser  Asp Phe Arg
        995                 1000                1005

Lys Asp  Phe Gln Phe Tyr Lys  Val Arg Glu Ile Asn  Asn Tyr His
    1010                1015                1020

His Ala  His Asp Ala Tyr Leu  Asn Ala Val Val Gly  Thr Ala Leu
    1025                1030                1035

Ile Lys  Lys Tyr Pro Lys Leu  Glu Ser Glu Phe Val  Tyr Gly Asp
    1040                1045                1050

Tyr Lys  Val Tyr Asp Val Arg  Lys Met Ile Ala Lys  Ser Glu Gln
    1055                1060                1065

Glu Ile  Gly Lys Ala Thr Ala  Lys Tyr Phe Phe Tyr  Ser Asn Ile
    1070                1075                1080

Met Asn  Phe Phe Lys Thr Glu  Ile Thr Leu Ala Asn  Gly Glu Ile
    1085                1090                1095

Arg Lys  Arg Pro Leu Ile Glu  Thr Asn Gly Glu Thr  Gly Glu Ile
    1100                1105                1110

Val Trp  Asp Lys Gly Arg Asp  Phe Ala Thr Val Arg  Lys Val Leu
    1115                1120                1125

Ser Met  Pro Gln Val Asn Ile  Val Lys Lys Thr Glu  Val Gln Thr
    1130                1135                1140

Gly Gly  Phe Ser Lys Glu Ser  Ile Leu Pro Lys Arg  Asn Ser Asp
    1145                1150                1155

Lys Leu  Ile Ala Arg Lys Lys  Asp Trp Asp Pro Lys  Lys Tyr Gly
    1160                1165                1170

Gly Phe  Asp Ser Pro Thr Val  Ala Tyr Ser Val Leu  Val Val Ala
    1175                1180                1185

Lys Val  Glu Lys Gly Lys Ser  Lys Lys Leu Lys Ser  Val Lys Glu
    1190                1195                1200

Leu Leu  Gly Ile Thr Ile Met  Glu Arg Ser Ser Phe  Glu Lys Asn
    1205                1210                1215

Pro Ile  Asp Phe Leu Glu Ala  Lys Gly Tyr Lys Glu  Val Lys Lys
    1220                1225                1230

Asp Leu  Ile Ile Lys Leu Pro  Lys Tyr Ser Leu Phe  Glu Leu Glu
    1235                1240                1245

Asn Gly  Arg Lys Arg Met Leu  Ala Ser Ala Gly Glu  Leu Gln Lys
    1250                1255                1260

Gly Asn  Glu Leu Ala Leu Pro  Ser Lys Tyr Val Asn  Phe Leu Tyr
```

```
    1265                1270                1275

Leu Ala  Ser His Tyr Glu Lys  Leu Lys Gly Ser Pro  Glu Asp Asn
    1280                1285                1290

Glu Gln  Lys Gln Leu Phe Val  Glu Gln His Lys His  Tyr Leu Asp
    1295                1300                1305

Glu Ile  Ile Glu Gln Ile Ser  Glu Phe Ser Lys Arg  Val Ile Leu
    1310                1315                1320

Ala Asp  Ala Asn Leu Asp Lys  Val Leu Ser Ala Tyr  Asn Lys His
    1325                1330                1335

Arg Asp  Lys Pro Ile Arg Glu  Gln Ala Glu Asn Ile  Ile His Leu
    1340                1345                1350

Phe Thr  Leu Thr Asn Leu Gly  Ala Pro Ala Ala Phe  Lys Tyr Phe
    1355                1360                1365

Asp Thr  Thr Ile Asp Arg Lys  Arg Tyr Thr Ser Thr  Lys Glu Val
    1370                1375                1380

Leu Asp  Ala Thr Leu Ile His  Gln Ser Ile Thr Gly  Leu Tyr Glu
    1385                1390                1395

Thr Arg  Ile Asp Leu Ser Gln  Leu Gly Gly Asp Glu  Gly Ala Pro
    1400                1405                1410

Lys Lys  Lys Arg Lys Val Gly  Ser Ser Gly Ser Pro  Lys Lys Lys
    1415                1420                1425

Arg Lys  Val Gly Ser Asp Ala  Leu Asp Asp Phe Asp  Leu Asp Met
    1430                1435                1440

Leu Gly  Ser Asp Ala Leu Asp  Asp Phe Gly Gly Gly  Ser Met Asp
    1445                1450                1455

Ser Leu  Leu Met Asn Arg Arg  Lys Phe Leu Tyr Gln  Phe Lys Asn
    1460                1465                1470

Val Arg  Trp Ala Lys Gly Arg  Arg Glu Thr Tyr Leu  Cys Tyr Val
    1475                1480                1485

Val Lys  Arg Arg Asp Ser Ala  Thr Ser Phe Ser Leu  Asp Phe Gly
    1490                1495                1500

Tyr Leu  Arg Asn Lys Asn Gly  Cys His Val Glu Leu  Leu Phe Leu
    1505                1510                1515

Arg Tyr  Ile Ser Asp Trp Asp  Leu Asp Pro Gly Arg  Cys Tyr Arg
    1520                1525                1530

Val Thr  Trp Phe Thr Ser Trp  Ser Pro Cys Tyr Asp  Cys Ala Arg
    1535                1540                1545

His Val  Ala Asp Phe Leu Arg  Gly Asn Pro Asn Leu  Ser Leu Arg
    1550                1555                1560

Ile Phe  Thr Ala Arg Leu Tyr  Phe Cys Glu Asp Arg  Lys Ala Glu
    1565                1570                1575

Pro Glu  Gly Leu Arg Arg Leu  His Arg Ala Gly Val  Gln Ile Ala
    1580                1585                1590

Ile Met  Thr Phe Lys Asp Tyr  Phe Tyr Cys Trp Asn  Thr Phe Val
    1595                1600                1605

Glu Asn  His Glu Arg Thr Phe  Lys Ala Trp Glu Gly  Leu His Glu
    1610                1615                1620

Asn Ser  Val Arg Leu Ser Arg  Gln Leu Arg Arg Ile  Leu Leu Pro
    1625                1630                1635
```

<210> SEQ ID NO 34
<211> LENGTH: 3
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: PAM sequence
<220> FEATURE:
<221> NAME/KEY: misc_feature
<222> LOCATION: (1)..(1)
<223> OTHER INFORMATION: n is a, c, g or t

<400> SEQUENCE: 34 ngg 3

<210> SEQ ID NO 35
<211> LENGTH: 5
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: PAM sequence
<220> FEATURE:
<221> NAME/KEY: misc_feature
<222> LOCATION: (1)..(2)
<223> OTHER INFORMATION: n is a, c, g or t
<220> FEATURE:
<221> NAME/KEY: misc_feature
<222> LOCATION: (4)..(5)
<223> OTHER INFORMATION: r is a or g

<400> SEQUENCE: 35 nngrr 5

<210> SEQ ID NO 36
<211> LENGTH: 6
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: PAM sequence
<220> FEATURE:
<221> NAME/KEY: misc_feature
<222> LOCATION: (1)..(2)
<223> OTHER INFORMATION: n is a, c, g or t

<400> SEQUENCE: 36 nnagaa 6

<210> SEQ ID NO 37
<211> LENGTH: 6
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: PAM sequence
<220> FEATURE:
<221> NAME/KEY: misc_feature
<222> LOCATION: (1)..(2)
<223> OTHER INFORMATION: n is a, c, g or t
<220> FEATURE:
<221> NAME/KEY: misc_feature
<222> LOCATION: (4)..(5)
<223> OTHER INFORMATION: r is a or g

<400> SEQUENCE: 37 nngrrt 6

<210> SEQ ID NO 38
<211> LENGTH: 3
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: PAM sequence

<400> SEQUENCE: 38 tgg 3

<210> SEQ ID NO 39
<211> LENGTH: 6
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: PAM sequence
<220> FEATURE:
<221> NAME/KEY: misc_feature
<222> LOCATION: (1)..(3)
<223> OTHER INFORMATION: n is a, c, g or t
<220> FEATURE:
<221> NAME/KEY: misc_feature
<222> LOCATION: (4)..(5)
<223> OTHER INFORMATION: r is a or g

<400> SEQUENCE: 39 nnnrrt 6

<210> SEQ ID NO 40
<211> LENGTH: 4
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: linker

<400> SEQUENCE: 40

Ser Gly Gly Ser
1

<210> SEQ ID NO 41
<211> LENGTH: 5
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: linker

<400> SEQUENCE: 41

Gly Ser Ser Gly Ser
1 5

<210> SEQ ID NO 42
<211> LENGTH: 4
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: linker

<400> SEQUENCE: 42

Gly Gly Gly Ser
1

<210> SEQ ID NO 43
<211> LENGTH: 5
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: linker

<400> SEQUENCE: 43

Gly Gly Gly Gly Ser
1               5

<210> SEQ ID NO 44
<211> LENGTH: 5
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: linker

<400> SEQUENCE: 44

Ser Ser Ser Ser Gly
1               5

<210> SEQ ID NO 45
<211> LENGTH: 5
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: linker

<400> SEQUENCE: 45

Gly Ser Gly Ser Ala
1               5

<210> SEQ ID NO 46
<211> LENGTH: 5
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: linker

<400> SEQUENCE: 46

Gly Gly Ser Gly Gly
1               5

<210> SEQ ID NO 47
<211> LENGTH: 4890
<212> TYPE: DNA
<213> ORGANISM: Artificial Sequence
<220> FEATURE:
<223> OTHER INFORMATION: synthesized
<220> FEATURE:

<221> NAME/KEY: misc_feature
<223> OTHER INFORMATION: Coding sequence of dCas9-XTEN-AID P182X

<400> SEQUENCE: 47

```
atggactata aggaccacga cggagactac aaggatcatg atattgatta caaagacgat      60
gacgataaga tggccccaaa gaagaagcgg aaggtcggta tccacggagt cccagcagct     120
accatggaca agaagtattc tatcggactg gccatcggga ctaatagcgt cgggtgggcc     180
gtgatcactg acgagtacaa ggtgccctct aagaagttca aggtgctcgg gaacaccgac     240
cggcattcca tcaagaaaaa tctgatcgga gctctcctct ttgattcagg ggagaccgct     300
gaagcaaccc gcctcaagcg gactgctaga cggcggtaca ccaggaggaa gaaccggatt     360
tgttaccttc aagagatatt ctccaacgaa atggcaaagg tcgacgacag cttcttccat     420
aggctggaag aatcattcct cgtggaagag gataagaagc atgaacggca tcccatcttc     480
ggtaatatcg tcgacgaggt ggcctatcac gagaaatacc caaccatcta ccatcttcgc     540
aaaaagctgg tggactcaac cgacaaggca gacctccggc ttatctacct ggccctggcc     600
cacatgatca agttcagagg ccacttcctg atcgagggcg acctcaatcc tgacaatagc     660
gatgtggata aactgttcat ccagctggtg cagacttaca accagctctt tgaagagaac     720
cccatcaatg caagcggagt cgatgccaag gccattctgt cagcccggct gtcaaagagc     780
cgcagacttg agaatcttat cgctcagctg ccgggtgaaa agaaaaatgg actgttcggg     840
aacctgattg ctctttcact tgggctgact cccaatttca agtctaattt cgacctggca     900
gaggatgcca agctgcaact gtccaaggac acctatgatg acgatctcga caacctcctg     960
gcccagatcg gtgaccaata cgccgacctt ttccttgctg ctaagaatct ttctgacgcc    1020
atcctgctgt ctgacattct ccgcgtgaac actgaaatca ccaaggcccc tctttcagct    1080
tcaatgatta agcggtatga tgagcaccac caggacctga ccctgcttaa ggcactcgtc    1140
cggcagcagc ttccggagaa gtacaaggaa atcttctttg accagtcaaa gaatggatac    1200
gccggctaca tcgacggagg tgcctcccaa gaggaatttt ataagtttat caaacctatc    1260
cttgagaaga tggacggcac cgaagagctc ctcgtgaaac tgaatcggga ggatctgctg    1320
cggaagcagc gcactttcga caatgggagc attccccacc agatccatct tggggagctt    1380
cacgccatcc ttcggcgcca agaggacttc taccccttc  ttaaggacaa cagggagaag    1440
attgagaaaa ttctcacttt ccgcatcccc tactacgtgg gacccctcgc cagaggaaat    1500
agccggtttg cttggatgac cagaaagtca gaagaaacta tcactccctg gaacttcgaa    1560
gaggtggtgg acaagggagc cagcgctcag tcattcatcg aacggatgac taacttcgat    1620
aagaacctcc ccaatgagaa ggtcctgccg aaacattccc tgctctacga gtactttacc    1680
gtgtacaacg agctgaccaa ggtgaaatat gtcaccgaag ggatgaggaa gcccgcattc    1740
ctgtcaggcg aacaaaagaa ggcaattgtg gaccttctgt tcaagaccaa tagaaaggtg    1800
accgtgaagc agctgaagga ggactatttc aagaaaattg aatgcttcga ctctgtggag    1860
attagcgggg tcgaagatcg gttcaacgca agcctgggta cctaccatga tctgcttaag    1920
atcatcaagg acaaggattt tctggacaat gaggagaaag aggacatcct tgaggacatt    1980
gtcctgactc tcactctgtt cgaggaccgg gaaatgatcg aggagaggct taagacctac    2040
gcccatctgt tcgacgataa agtgatgaag caacttaaac ggagaagata taccggatgg    2100
ggacgcctta gccgcaaact catcaacgga atccgggaca aacagagcgg aaagaccatt    2160
cttgatttcc ttaagagcga cggattcgct aatcgcaact tcatgcaact tatccatgat    2220
```

```
gattccctga cctttaagga ggacatccag aaggcccaag tgtctggaca aggtgactca   2280
ctgcacgagc atatcgcaaa tctggctggt tcacccgcta ttaagaaggg tattctccag   2340
accgtgaaag tcgtggacga gctggtcaag gtgatgggtc gccataaacc agagaacatt   2400
gtcatcgaga tggccaggga aaaccagact acccagaagg gacagaagaa cagcagggag   2460
cggatgaaaa gaattgagga agggattaag gagctcgggt cacagatcct taaagagcac   2520
ccggtggaaa acacccagct tcagaatgag aagctctatc tgtactacct tcaaaatgga   2580
cgcgatatgt atgtggacca agagcttgat atcaacaggc tctcagacta cgacgtggac   2640
gccatcgtcc ctcagagctt cctcaaagac gactcaattg acaataaggt gctgactcgc   2700
tcagacaaga accggggaaa gtcagataac gtgccctcag aggaagtcgt gaaaaagatg   2760
aagaactatt ggcgccagct tctgaacgca aagctgatca ctcagcggaa gttcgacaat   2820
ctcactaagg ctgagagggg cggactgagc gaactggaca aagcaggatt cattaaacgg   2880
caacttgtgg agactcggca gattactaaa catgtagccc aaatccttga ctcacgcatg   2940
aataccaagt acgacgaaaa cgacaaactt atccgcgagg tgaaggtgat taccctgaag   3000
tccaagctgg tcagcgattt cagaaaggac tttcaattct acaaagtgcg ggagatcaat   3060
aactatcatc atgctcatga cgcatatctg aatgccgtgg tgggaaccgc cctgatcaag   3120
aagtacccaa agctggaaag cgagttcgtg tacggagact acaaggtcta cgacgtgcgc   3180
aagatgattg ccaaatctga gcaggagatc ggaaaggcca ccgcaaagta cttcttctac   3240
agcaacatca tgaatttctt caagaccgaa atcacccttg caaacggtga gatccggaag   3300
aggccgctca tcgagactaa tggggagact ggcgaaatcg tgtgggacaa gggcagagat   3360
ttcgctaccg tgcgcaaagt gctttctatg cctcaagtga acatcgtgaa gaaaaccgag   3420
gtgcaaaccg gaggcttttc taaggaatca atcctcccca agcgcaactc cgacaagctc   3480
attgcaagga agaaggattg ggaccctaag aagtacggcg gattcgattc accaactgtg   3540
gcttattctg tcctggtcgt ggctaaggtg gaaaaaggaa agtctaagaa gctcaagagc   3600
gtgaaggaac tgctgggtat caccattatg gagcgcagct ccttcgagaa gaacccaatt   3660
gactttctcg aagccaaagg ttacaaggaa gtcaagaagg accttatcat caagctccca   3720
aagtatagcc tgttcgaact ggagaatggg cggaagcgga tgctcgcctc cgctggcgaa   3780
cttcagaagg gtaatgagct ggctctcccc tccaagtacg tgaatttcct ctaccttgca   3840
agccattacg agaagctgaa ggggagcccc gaggacaacg agcaaaagca actgtttgtg   3900
gagcagcata agcattatct ggacgagatc attgagcaga tttccgagtt ttctaaacgc   3960
gtcattctcg ctgatgccaa cctcgataaa gtccttagcg catacaataa gcacagagac   4020
aaaccaattc gggagcaggc tgagaatatc atccacctgt tcaccctcac caatcttggt   4080
gcccctgccg cattcaagta cttcgacacc accatcgacc ggaaacgcta tacctccacc   4140
aaagaagtgc tggacgccac cctcatccac cagagcatca ccggacttta cgaaactcgg   4200
attgacctct cacagctcgg aggggatgag ggagctccca agaaaaagcg caaggtaggt   4260
agttccggat ctccgaaaaa gaaacgcaaa gttagcggca gcgagactcc cgggacctca   4320
gagtccgcca cacccgaaag tatggacagc ctcttgatga accggaggaa gtttctttac   4380
caattcaaaa atgtccgctg ggctaagggt cggcgtgaga cctacctgtg ctacgtagtg   4440
aagaggcgtg acagtgctac atccttttca ctggactttg gttatcttcg caataagaac   4500
ggctgccacg tggaattgct cttcctccgc tacatctcgg actgggacct agaccctggc   4560
cgctgctacc gcgtcacctg gttcacctcc tggagcccct gctacgactg tgcccgacat   4620
```

gtggccgact ttctgcgagg gaaccccaac ctcagtctga ggatcttcac cgcgcgcctc 4680
tacttctgtg aggaccgcaa ggctgagccc gaggggctgc ggcggctgca ccgcgccggg 4740
gtgcaaatag ccatcatgac cttcaaagat tatttttact gctggaatac ttttgtagaa 4800
aaccatgaaa gaactttcaa agcctgggaa gggctgcatg aaaattcagt tcgtctctcc 4860
agacagcttc ggcgcatcct tttgccctga 4890

<210> SEQ ID NO 48
<211> LENGTH: 1629
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Amino acid sequence of dCas9-XTEN-AID P182X

<400> SEQUENCE: 48

Met Asp Tyr Lys Asp His Asp Gly Asp Tyr Lys Asp His Asp Ile Asp
1 5 10 15

Tyr Lys Asp Asp Asp Asp Lys Met Ala Pro Lys Lys Lys Arg Lys Val
20 25 30

Gly Ile His Gly Val Pro Ala Ala Thr Met Asp Lys Lys Tyr Ser Ile
35 40 45

Gly Leu Ala Ile Gly Thr Asn Ser Val Gly Trp Ala Val Ile Thr Asp
50 55 60

Glu Tyr Lys Val Pro Ser Lys Lys Phe Lys Val Leu Gly Asn Thr Asp
65 70 75 80

Arg His Ser Ile Lys Lys Asn Leu Ile Gly Ala Leu Leu Phe Asp Ser
85 90 95

Gly Glu Thr Ala Glu Ala Thr Arg Leu Lys Arg Thr Ala Arg Arg Arg
100 105 110

Tyr Thr Arg Arg Lys Asn Arg Ile Cys Tyr Leu Gln Glu Ile Phe Ser
115 120 125

Asn Glu Met Ala Lys Val Asp Asp Ser Phe Phe His Arg Leu Glu Glu
130 135 140

Ser Phe Leu Val Glu Glu Asp Lys Lys His Glu Arg His Pro Ile Phe
145 150 155 160

Gly Asn Ile Val Asp Glu Val Ala Tyr His Glu Lys Tyr Pro Thr Ile
165 170 175

Tyr His Leu Arg Lys Lys Leu Val Asp Ser Thr Asp Lys Ala Asp Leu
180 185 190

Arg Leu Ile Tyr Leu Ala Leu Ala His Met Ile Lys Phe Arg Gly His
195 200 205

Phe Leu Ile Glu Gly Asp Leu Asn Pro Asp Asn Ser Asp Val Asp Lys
210 215 220

Leu Phe Ile Gln Leu Val Gln Thr Tyr Asn Gln Leu Phe Glu Glu Asn
225 230 235 240

Pro Ile Asn Ala Ser Gly Val Asp Ala Lys Ala Ile Leu Ser Ala Arg
245 250 255

Leu Ser Lys Ser Arg Arg Leu Glu Asn Leu Ile Ala Gln Leu Pro Gly
260 265 270

Glu Lys Lys Asn Gly Leu Phe Gly Asn Leu Ile Ala Leu Ser Leu Gly
275 280 285

Leu Thr Pro Asn Phe Lys Ser Asn Phe Asp Leu Ala Glu Asp Ala Lys

```
    290                 295                 300

Leu Gln Leu Ser Lys Asp Thr Tyr Asp Asp Asp Leu Asp Asn Leu Leu
305                 310                 315                 320

Ala Gln Ile Gly Asp Gln Tyr Ala Asp Leu Phe Leu Ala Ala Lys Asn
                325                 330                 335

Leu Ser Asp Ala Ile Leu Leu Ser Asp Ile Leu Arg Val Asn Thr Glu
            340                 345                 350

Ile Thr Lys Ala Pro Leu Ser Ala Ser Met Ile Lys Arg Tyr Asp Glu
        355                 360                 365

His His Gln Asp Leu Thr Leu Leu Lys Ala Leu Val Arg Gln Gln Leu
    370                 375                 380

Pro Glu Lys Tyr Lys Glu Ile Phe Phe Asp Gln Ser Lys Asn Gly Tyr
385                 390                 395                 400

Ala Gly Tyr Ile Asp Gly Gly Ala Ser Gln Glu Glu Phe Tyr Lys Phe
                405                 410                 415

Ile Lys Pro Ile Leu Glu Lys Met Asp Gly Thr Glu Glu Leu Leu Val
            420                 425                 430

Lys Leu Asn Arg Glu Asp Leu Leu Arg Lys Gln Arg Thr Phe Asp Asn
        435                 440                 445

Gly Ser Ile Pro His Gln Ile His Leu Gly Glu Leu His Ala Ile Leu
    450                 455                 460

Arg Arg Gln Glu Asp Phe Tyr Pro Phe Leu Lys Asp Asn Arg Glu Lys
465                 470                 475                 480

Ile Glu Lys Ile Leu Thr Phe Arg Ile Pro Tyr Tyr Val Gly Pro Leu
                485                 490                 495

Ala Arg Gly Asn Ser Arg Phe Ala Trp Met Thr Arg Lys Ser Glu Glu
            500                 505                 510

Thr Ile Thr Pro Trp Asn Phe Glu Glu Val Val Asp Lys Gly Ala Ser
        515                 520                 525

Ala Gln Ser Phe Ile Glu Arg Met Thr Asn Phe Asp Lys Asn Leu Pro
    530                 535                 540

Asn Glu Lys Val Leu Pro Lys His Ser Leu Leu Tyr Glu Tyr Phe Thr
545                 550                 555                 560

Val Tyr Asn Glu Leu Thr Lys Val Lys Tyr Val Thr Glu Gly Met Arg
                565                 570                 575

Lys Pro Ala Phe Leu Ser Gly Glu Gln Lys Lys Ala Ile Val Asp Leu
            580                 585                 590

Leu Phe Lys Thr Asn Arg Lys Val Thr Val Lys Gln Leu Lys Glu Asp
        595                 600                 605

Tyr Phe Lys Lys Ile Glu Cys Phe Asp Ser Val Glu Ile Ser Gly Val
    610                 615                 620

Glu Asp Arg Phe Asn Ala Ser Leu Gly Thr Tyr His Asp Leu Leu Lys
625                 630                 635                 640

Ile Ile Lys Asp Lys Asp Phe Leu Asp Asn Glu Glu Lys Glu Asp Ile
                645                 650                 655

Leu Glu Asp Ile Val Leu Thr Leu Thr Leu Phe Glu Asp Arg Glu Met
            660                 665                 670

Ile Glu Glu Arg Leu Lys Thr Tyr Ala His Leu Phe Asp Asp Lys Val
        675                 680                 685

Met Lys Gln Leu Lys Arg Arg Arg Tyr Thr Gly Trp Gly Arg Leu Ser
    690                 695                 700

Arg Lys Leu Ile Asn Gly Ile Arg Asp Lys Gln Ser Gly Lys Thr Ile
705                 710                 715                 720
```

```
Leu Asp Phe Leu Lys Ser Asp Gly Phe Ala Asn Arg Asn Phe Met Gln
                725                 730                 735

Leu Ile His Asp Asp Ser Leu Thr Phe Lys Glu Asp Ile Gln Lys Ala
            740                 745                 750

Gln Val Ser Gly Gln Gly Asp Ser Leu His Glu His Ile Ala Asn Leu
        755                 760                 765

Ala Gly Ser Pro Ala Ile Lys Lys Gly Ile Leu Gln Thr Val Lys Val
    770                 775                 780

Val Asp Glu Leu Val Lys Val Met Gly Arg His Lys Pro Glu Asn Ile
785                 790                 795                 800

Val Ile Glu Met Ala Arg Glu Asn Gln Thr Thr Gln Lys Gly Gln Lys
                805                 810                 815

Asn Ser Arg Glu Arg Met Lys Arg Ile Glu Glu Gly Ile Lys Glu Leu
            820                 825                 830

Gly Ser Gln Ile Leu Lys Glu His Pro Val Glu Asn Thr Gln Leu Gln
        835                 840                 845

Asn Glu Lys Leu Tyr Leu Tyr Tyr Leu Gln Asn Gly Arg Asp Met Tyr
    850                 855                 860

Val Asp Gln Glu Leu Asp Ile Asn Arg Leu Ser Asp Tyr Asp Val Asp
865                 870                 875                 880

Ala Ile Val Pro Gln Ser Phe Leu Lys Asp Asp Ser Ile Asp Asn Lys
                885                 890                 895

Val Leu Thr Arg Ser Asp Lys Asn Arg Gly Lys Ser Asp Asn Val Pro
            900                 905                 910

Ser Glu Glu Val Val Lys Lys Met Lys Asn Tyr Trp Arg Gln Leu Leu
        915                 920                 925

Asn Ala Lys Leu Ile Thr Gln Arg Lys Phe Asp Asn Leu Thr Lys Ala
    930                 935                 940

Glu Arg Gly Gly Leu Ser Glu Leu Asp Lys Ala Gly Phe Ile Lys Arg
945                 950                 955                 960

Gln Leu Val Glu Thr Arg Gln Ile Thr Lys His Val Ala Gln Ile Leu
                965                 970                 975

Asp Ser Arg Met Asn Thr Lys Tyr Asp Glu Asn Asp Lys Leu Ile Arg
            980                 985                 990

Glu Val Lys Val Ile Thr Leu Lys  Ser Lys Leu Val Ser  Asp Phe Arg
        995                  1000                 1005

Lys Asp  Phe Gln Phe Tyr Lys  Val Arg Glu Ile Asn  Asn Tyr His
    1010                 1015                 1020

His Ala  His Asp Ala Tyr Leu  Asn Ala Val Val Gly  Thr Ala Leu
    1025                 1030                 1035

Ile Lys  Lys Tyr Pro Lys Leu  Glu Ser Glu Phe Val  Tyr Gly Asp
    1040                 1045                 1050

Tyr Lys  Val Tyr Asp Val Arg  Lys Met Ile Ala Lys  Ser Glu Gln
    1055                 1060                 1065

Glu Ile  Gly Lys Ala Thr Ala  Lys Tyr Phe Phe Tyr  Ser Asn Ile
    1070                 1075                 1080

Met Asn  Phe Phe Lys Thr Glu  Ile Thr Leu Ala Asn  Gly Glu Ile
    1085                 1090                 1095

Arg Lys  Arg Pro Leu Ile Glu  Thr Asn Gly Glu Thr  Gly Glu Ile
    1100                 1105                 1110

Val Trp  Asp Lys Gly Arg Asp  Phe Ala Thr Val Arg  Lys Val Leu
    1115                 1120                 1125
```

```
Ser Met  Pro Gln Val Asn Ile  Val Lys Lys Thr Glu  Val Gln Thr
    1130                 1135                 1140

Gly Gly  Phe Ser Lys Glu Ser  Ile Leu Pro Lys Arg  Asn Ser Asp
    1145                 1150                 1155

Lys Leu  Ile Ala Arg Lys Lys  Asp Trp Asp Pro Lys  Lys Tyr Gly
    1160                 1165                 1170

Gly Phe  Asp Ser Pro Thr Val  Ala Tyr Ser Val Leu  Val Val Ala
    1175                 1180                 1185

Lys Val  Glu Lys Gly Lys Ser  Lys Lys Leu Lys Ser  Val Lys Glu
    1190                 1195                 1200

Leu Leu  Gly Ile Thr Ile Met  Glu Arg Ser Ser Phe  Glu Lys Asn
    1205                 1210                 1215

Pro Ile  Asp Phe Leu Glu Ala  Lys Gly Tyr Lys Glu  Val Lys Lys
    1220                 1225                 1230

Asp Leu  Ile Ile Lys Leu Pro  Lys Tyr Ser Leu Phe  Glu Leu Glu
    1235                 1240                 1245

Asn Gly  Arg Lys Arg Met Leu  Ala Ser Ala Gly Glu  Leu Gln Lys
    1250                 1255                 1260

Gly Asn  Glu Leu Ala Leu Pro  Ser Lys Tyr Val Asn  Phe Leu Tyr
    1265                 1270                 1275

Leu Ala  Ser His Tyr Glu Lys  Leu Lys Gly Ser Pro  Glu Asp Asn
    1280                 1285                 1290

Glu Gln  Lys Gln Leu Phe Val  Glu Gln His Lys His  Tyr Leu Asp
    1295                 1300                 1305

Glu Ile  Ile Glu Gln Ile Ser  Glu Phe Ser Lys Arg  Val Ile Leu
    1310                 1315                 1320

Ala Asp  Ala Asn Leu Asp Lys  Val Leu Ser Ala Tyr  Asn Lys His
    1325                 1330                 1335

Arg Asp  Lys Pro Ile Arg Glu  Gln Ala Glu Asn Ile  Ile His Leu
    1340                 1345                 1350

Phe Thr  Leu Thr Asn Leu Gly  Ala Pro Ala Ala Phe  Lys Tyr Phe
    1355                 1360                 1365

Asp Thr  Thr Ile Asp Arg Lys  Arg Tyr Thr Ser Thr  Lys Glu Val
    1370                 1375                 1380

Leu Asp  Ala Thr Leu Ile His  Gln Ser Ile Thr Gly  Leu Tyr Glu
    1385                 1390                 1395

Thr Arg  Ile Asp Leu Ser Gln  Leu Gly Gly Asp Glu  Gly Ala Pro
    1400                 1405                 1410

Lys Lys  Lys Arg Lys Val Gly  Ser Ser Gly Ser Pro  Lys Lys Lys
    1415                 1420                 1425

Arg Lys  Val Ser Gly Ser Glu  Thr Pro Gly Thr Ser  Glu Ser Ala
    1430                 1435                 1440

Thr Pro  Glu Ser Met Asp Ser  Leu Leu Met Asn Arg  Arg Lys Phe
    1445                 1450                 1455

Leu Tyr  Gln Phe Lys Asn Val  Arg Trp Ala Lys Gly  Arg Arg Glu
    1460                 1465                 1470

Thr Tyr  Leu Cys Tyr Val Val  Lys Arg Arg Asp Ser  Ala Thr Ser
    1475                 1480                 1485

Phe Ser  Leu Asp Phe Gly Tyr  Leu Arg Asn Lys Asn  Gly Cys His
    1490                 1495                 1500

Val Glu  Leu Leu Phe Leu Arg  Tyr Ile Ser Asp Trp  Asp Leu Asp
    1505                 1510                 1515

Pro Gly  Arg Cys Tyr Arg Val  Thr Trp Phe Thr Ser  Trp Ser Pro
```

```
    1520                1525                1530

Cys Tyr  Asp Cys Ala Arg His  Val Ala Asp Phe Leu  Arg Gly Asn
    1535                1540                1545

Pro Asn  Leu Ser Leu Arg Ile  Phe Thr Ala Arg Leu  Tyr Phe Cys
    1550                1555                1560

Glu Asp  Arg Lys Ala Glu Pro  Glu Gly Leu Arg Arg  Leu His Arg
    1565                1570                1575

Ala Gly  Val Gln Ile Ala Ile  Met Thr Phe Lys Asp  Tyr Phe Tyr
    1580                1585                1590

Cys Trp  Asn Thr Phe Val Glu  Asn His Glu Arg Thr  Phe Lys Ala
    1595                1600                1605

Trp Glu  Gly Leu His Glu Asn  Ser Val Arg Leu Ser  Arg Gln Leu
    1610                1615                1620

Arg Arg  Ile Leu Leu Pro
    1625


<210> SEQ ID NO 49
<211> LENGTH: 4089
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Coding sequence of AIDx-saCas9(KKH nickase)-Ugi

<400> SEQUENCE: 49

atggacagcc tcttgatgaa ccggaggaag tttctttacc aattcaaaaa tgtccgctgg     60

gctaagggtc ggcgtgagac ctacctgtgc tacgtagtga agaggcgtga cagtgctaca    120

tcctttttcac tggactttgg ttatcttcgc aataagaacg gctgccacgt ggaattgctc    180

ttcctccgct acatctcgga ctgggaccta gaccctggcc gctgctaccg cgtcacctgg    240

ttcacctcct ggagcccctg ctacgactgt gcccgacatg tggccgactt tctgcgaggg    300

aaccccaacc tcagtctgag gatcttcacc gcgcgcctct acttctgtga ggaccgcaag    360

gctgagcccg aggggctgcg gcggctgcac cgcgccgggg tgcaaatagc catcatgacc    420

ttcaaagatt atttttactg ctggaatact tttgtagaaa accatgaaag aactttcaaa    480

gcctgggaag ggctgcatga aaattcagtt cgtctctcca gacagcttcg gcgcatcctt    540

ttgcccagcg gcagcgagac tcccgggacc tcagagtccg ccacacccga aagtgggaaa    600

cggaactaca tcctggggct tgacattggg ataaccagcg ttggctacgg aattattgat    660

tatgagacac gcgatgtgat tgacgccggg gttaggctgt tcaaagaggc caacgttgaa    720

aacaacgagg gaagacggag taagcgcgga gcaagaagac tcaagcgcag acggagacat    780

cggattcaga gggtgaaaaa gctgctcttc gattacaatc tcctgaccga tcatagtgag    840

ctgagcggaa tcaaccccta cgaggcgcga gtgaaagggc tttcccagaa gctgtccgaa    900

gaggagttct ccgccgcgtt gctgcacctg gccaaacgga ggggggttca caatgtaaac    960

gaagtggagg aggacacggg caatgaactt agtacgaaag aacagatcag taggaactct   1020

aaggctctcg aagagaaata cgtcgctgag ttgcagcttg agagactgaa aaaagacggc   1080

gaagtacgcg gatctattaa taggttcaag acttcagatt acgtaaagga agccaagcag   1140

ctcctgaaag tacagaaagc gtaccatcag ctcgatcaga gcttcatcga tacctacata   1200

gatttgctgg agacacggag gacatactac gagggcccag gggaaggatc tccttttggg   1260

tggaaggaca tcaaggaatg gtacgagatg cttatgggac attgtacata ttttccggag   1320
```

```
gagctcagga gcgtcaagta cgcctacaat gccgacctgt acaatgccct caatgacctc   1380
aataacctcg tgattaccag ggacgagaac gagaagctgg agtactatga aaagttccag   1440
attatcgaga atgtgtttaa gcagaagaag aagccgacac ttaagcagat tgcaaaggaa   1500
atcctcgtga atgaggaaga tatcaaggga tacagagtga caagtacagg caagcccgag   1560
ttcacaaatc tgaaggtgta ccacgatatt aaggacataa ccgcacgaaa ggagataatc   1620
gaaaacgctg agctcctcga tcagatcgca aaaattctta ccatctacca gtctagtgag   1680
gacattcagg aggaactgac taatctgaac agtgagctca cccaagagga aattgagcag   1740
atttcaaacc tgaaaggcta caccgggacg cacaatctga gcctcaaagc aatcaacctc   1800
attctggatg aactttggca cacaaatgac aaccaaattg ccatattcaa ccgcctgaaa   1860
ctggtgccaa aaaaagtgga tctgtcacag caaaaggaaa tccctacaac cttggttgac   1920
gattttattc tgtcccccgt tgtcaagcgg agcttcatcc agtcaatcaa ggtgatcaat   1980
gccatcatta aaaaatacgg attgccaaac gatataatta tcgagcttgc acgagagaag   2040
aactcaaagg acgcccagaa gatgattaac gaaatgcaga agcgcaaccg ccagacaaac   2100
gaacgcatag aggaaattat aagaacaacc ggcaaagaga atgccaagta tctgatcgag   2160
aaaatcaagc tgcacgacat gcaagaaggc aagtgcctgt actctctgga agctatccca   2220
ctcgaagatc tgctgaataa tccattcaat tacgaggtgg accacatcat ccctagatcc   2280
gtaagctttg acaattcctt caataacaaa gttctggtta aacaggagga aaattctaaa   2340
aaagggaacc ggaccccgtt ccagtacctg agctccagtg acagcaagat tagctacgag   2400
acttttaaga aacatattct gaatctggcc aaaggcaaag gcaggatcag caagaccaag   2460
aaggagtacc tcctcgaaga acgcgacatt aacagattta gtgtgcagaa agatttcatc   2520
aaccgaaacc ttgtcgatac tcggtacgcc acgagaggcc tgatgaatct cctcaggagc   2580
tacttccgcg tcaataatct ggacgttaaa gtcaagagca taaatggggg attcaccagc   2640
tttctgagga gaaagtggaa gtttaagaag gaacgaaaca aaggatacaa gcaccatgct   2700
gaggatgctt tgatcatcgc taacgcggac tttatcttta aggaatggaa aaagctggat   2760
aaggcaaaga aagtgatgga aaaccagatg ttcgaggaga agcaggcaga gtcaatgcct   2820
gagatcgaga cagagcagga atacaaggaa attttcatca cccctcatca gattaaacac   2880
ataaaggact tcaaagacta taaatactct catagggtgg acaaaaaacc caatcgcaag   2940
ctcattaatg acaccctgta ctcaacacgg aaggatgata aaggtaatac cttgattgtg   3000
aataatctta atggattgta tgacaaagat aacgacaagc tcaagaagct gatcaacaag   3060
tctccagaga agctccttat gtatcaccac gacccacaga cttatcagaa attgaaactg   3120
atcatggagc aatacgggga tgagaagaac ccactctaca aatattatga ggaaacaggt   3180
aattacctga ccaagtactc caagaaggat aacggaccag tgatcaaaaa gataaagtac   3240
tatggcaaca aacttaatgc gcatttggac ataactgacg attaccccaa ttctcgaaac   3300
aaggttgtga agctctccct gaagccttat agatttgacg tgtacctgga taatggggtt   3360
tataaattcg tcaccgtgaa aaatctggac gtgatcaaaa aggagaacta ttatgaagta   3420
aactcaaagt gctatgagga ggcgaagaag ctgaagaaga tctccaatca ggccgagttc   3480
atcgcttcct tctataagaa cgatctcatc aagatcaatg gagagcttta tcgcgtcatt   3540
ggtgtgaaca atgacttgct gaacaggatc gaagtcaata tgatagacat tacctaccgg   3600
gagtatctcg aaaacatgaa tgataaacgg ccgcctcaca tcatcaagac aatcgcatct   3660
```

-continued

```
aaaactcagt caataaaaaa gtactctacc gatatcctgg ggaatctcta tgaagtgaag   3720

tcaaagaagc acccacaaat cattaaaaaa ggtggatcct ctggtggttc tactaatctg   3780

tcagatatta ttgaaaagga gaccggtaag caactggtta tccaggaatc catcctcatg   3840

ctcccagagg aggtggaaga agtcattggg aacaagccgg aaagcgatat actcgtgcac   3900

accgcctacg acgagagcac cgacgagaat gtcatgcttc tgactagcga cgcccctgaa   3960

tacaagcctt gggctctggt catacaggat agcaacggtg agaacaagat taagatgctc   4020

tctggtggtt ctcccaagaa gaagaggaaa gtcggatcct acccatacga tgttccagat   4080

tacgcttaa                                                           4089


<210> SEQ ID NO 50
<211> LENGTH: 1362
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Amino acid sequence of AIDx-saCas9(KKH
      nickase)-Ugi

<400> SEQUENCE: 50

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Ser Gly Ser Glu Thr Pro Gly Thr Ser Glu
            180                 185                 190

Ser Ala Thr Pro Glu Ser Gly Lys Arg Asn Tyr Ile Leu Gly Leu Asp
        195                 200                 205

Ile Gly Ile Thr Ser Val Gly Tyr Gly Ile Ile Asp Tyr Glu Thr Arg
    210                 215                 220

Asp Val Ile Asp Ala Gly Val Arg Leu Phe Lys Glu Ala Asn Val Glu
225                 230                 235                 240

Asn Asn Glu Gly Arg Arg Ser Lys Arg Gly Ala Arg Arg Leu Lys Arg
                245                 250                 255

Arg Arg Arg His Arg Ile Gln Arg Val Lys Lys Leu Leu Phe Asp Tyr
```

-continued

```
            260                 265                 270

Asn Leu Leu Thr Asp His Ser Glu Leu Ser Gly Ile Asn Pro Tyr Glu
        275                 280                 285

Ala Arg Val Lys Gly Leu Ser Gln Lys Leu Ser Glu Glu Glu Phe Ser
    290                 295                 300

Ala Ala Leu Leu His Leu Ala Lys Arg Arg Gly Val His Asn Val Asn
305                 310                 315                 320

Glu Val Glu Glu Asp Thr Gly Asn Glu Leu Ser Thr Lys Glu Gln Ile
                325                 330                 335

Ser Arg Asn Ser Lys Ala Leu Glu Glu Lys Tyr Val Ala Glu Leu Gln
            340                 345                 350

Leu Glu Arg Leu Lys Lys Asp Gly Glu Val Arg Gly Ser Ile Asn Arg
        355                 360                 365

Phe Lys Thr Ser Asp Tyr Val Lys Glu Ala Lys Gln Leu Leu Lys Val
    370                 375                 380

Gln Lys Ala Tyr His Gln Leu Asp Gln Ser Phe Ile Asp Thr Tyr Ile
385                 390                 395                 400

Asp Leu Leu Glu Thr Arg Arg Thr Tyr Tyr Glu Gly Pro Gly Glu Gly
                405                 410                 415

Ser Pro Phe Gly Trp Lys Asp Ile Lys Glu Trp Tyr Glu Met Leu Met
            420                 425                 430

Gly His Cys Thr Tyr Phe Pro Glu Glu Leu Arg Ser Val Lys Tyr Ala
        435                 440                 445

Tyr Asn Ala Asp Leu Tyr Asn Ala Leu Asn Asp Leu Asn Asn Leu Val
    450                 455                 460

Ile Thr Arg Asp Glu Asn Glu Lys Leu Glu Tyr Tyr Glu Lys Phe Gln
465                 470                 475                 480

Ile Ile Glu Asn Val Phe Lys Gln Lys Lys Lys Pro Thr Leu Lys Gln
                485                 490                 495

Ile Ala Lys Glu Ile Leu Val Asn Glu Glu Asp Ile Lys Gly Tyr Arg
            500                 505                 510

Val Thr Ser Thr Gly Lys Pro Glu Phe Thr Asn Leu Lys Val Tyr His
        515                 520                 525

Asp Ile Lys Asp Ile Thr Ala Arg Lys Glu Ile Ile Glu Asn Ala Glu
    530                 535                 540

Leu Leu Asp Gln Ile Ala Lys Ile Leu Thr Ile Tyr Gln Ser Ser Glu
545                 550                 555                 560

Asp Ile Gln Glu Glu Leu Thr Asn Leu Asn Ser Glu Leu Thr Gln Glu
                565                 570                 575

Glu Ile Glu Gln Ile Ser Asn Leu Lys Gly Tyr Thr Gly Thr His Asn
            580                 585                 590

Leu Ser Leu Lys Ala Ile Asn Leu Ile Leu Asp Glu Leu Trp His Thr
        595                 600                 605

Asn Asp Asn Gln Ile Ala Ile Phe Asn Arg Leu Lys Leu Val Pro Lys
    610                 615                 620

Lys Val Asp Leu Ser Gln Gln Lys Glu Ile Pro Thr Thr Leu Val Asp
625                 630                 635                 640

Asp Phe Ile Leu Ser Pro Val Val Lys Arg Ser Phe Ile Gln Ser Ile
                645                 650                 655

Lys Val Ile Asn Ala Ile Ile Lys Lys Tyr Gly Leu Pro Asn Asp Ile
            660                 665                 670

Ile Ile Glu Leu Ala Arg Glu Lys Asn Ser Lys Asp Ala Gln Lys Met
        675                 680                 685
```

```
Ile Asn Glu Met Gln Lys Arg Asn Arg Gln Thr Asn Glu Arg Ile Glu
    690                 695                 700

Glu Ile Ile Arg Thr Thr Gly Lys Glu Asn Ala Lys Tyr Leu Ile Glu
705                 710                 715                 720

Lys Ile Lys Leu His Asp Met Gln Glu Gly Lys Cys Leu Tyr Ser Leu
                725                 730                 735

Glu Ala Ile Pro Leu Glu Asp Leu Leu Asn Asn Pro Phe Asn Tyr Glu
            740                 745                 750

Val Asp His Ile Ile Pro Arg Ser Val Ser Phe Asp Asn Ser Phe Asn
        755                 760                 765

Asn Lys Val Leu Val Lys Gln Glu Glu Asn Ser Lys Lys Gly Asn Arg
    770                 775                 780

Thr Pro Phe Gln Tyr Leu Ser Ser Ser Asp Ser Lys Ile Ser Tyr Glu
785                 790                 795                 800

Thr Phe Lys Lys His Ile Leu Asn Leu Ala Lys Gly Lys Gly Arg Ile
                805                 810                 815

Ser Lys Thr Lys Lys Glu Tyr Leu Leu Glu Glu Arg Asp Ile Asn Arg
            820                 825                 830

Phe Ser Val Gln Lys Asp Phe Ile Asn Arg Asn Leu Val Asp Thr Arg
        835                 840                 845

Tyr Ala Thr Arg Gly Leu Met Asn Leu Leu Arg Ser Tyr Phe Arg Val
    850                 855                 860

Asn Asn Leu Asp Val Lys Val Lys Ser Ile Asn Gly Gly Phe Thr Ser
865                 870                 875                 880

Phe Leu Arg Arg Lys Trp Lys Phe Lys Lys Glu Arg Asn Lys Gly Tyr
                885                 890                 895

Lys His His Ala Glu Asp Ala Leu Ile Ile Ala Asn Ala Asp Phe Ile
            900                 905                 910

Phe Lys Glu Trp Lys Lys Leu Asp Lys Ala Lys Lys Val Met Glu Asn
        915                 920                 925

Gln Met Phe Glu Glu Lys Gln Ala Glu Ser Met Pro Glu Ile Glu Thr
    930                 935                 940

Glu Gln Glu Tyr Lys Glu Ile Phe Ile Thr Pro His Gln Ile Lys His
945                 950                 955                 960

Ile Lys Asp Phe Lys Asp Tyr Lys Tyr Ser His Arg Val Asp Lys Lys
                965                 970                 975

Pro Asn Arg Lys Leu Ile Asn Asp Thr Leu Tyr Ser Thr Arg Lys Asp
            980                 985                 990

Asp Lys Gly Asn Thr Leu Ile Val  Asn Asn Leu Asn Gly  Leu Tyr Asp
        995                 1000                1005

Lys Asp  Asn Asp Lys Leu Lys  Lys Leu Ile Asn Lys  Ser Pro Glu
    1010                 1015                 1020

Lys Leu  Leu Met Tyr His His  Asp Pro Gln Thr Tyr  Gln Lys Leu
    1025                 1030                 1035

Lys Leu  Ile Met Glu Gln Tyr  Gly Asp Glu Lys Asn  Pro Leu Tyr
    1040                 1045                 1050

Lys Tyr  Tyr Glu Glu Thr Gly  Asn Tyr Leu Thr Lys  Tyr Ser Lys
    1055                 1060                 1065

Lys Asp  Asn Gly Pro Val Ile  Lys Lys Ile Lys Tyr  Tyr Gly Asn
    1070                 1075                 1080

Lys Leu  Asn Ala His Leu Asp  Ile Thr Asp Asp Tyr  Pro Asn Ser
    1085                 1090                 1095
```

```
Arg Asn  Lys Val Val Lys Leu  Ser Leu Lys Pro Tyr  Arg Phe Asp
    1100                 1105                 1110

Val Tyr  Leu Asp Asn Gly Val  Tyr Lys Phe Val Thr  Val Lys Asn
    1115                 1120                 1125

Leu Asp  Val Ile Lys Lys Glu  Asn Tyr Tyr Glu Val  Asn Ser Lys
    1130                 1135                 1140

Cys Tyr  Glu Glu Ala Lys Lys  Leu Lys Lys Ile Ser  Asn Gln Ala
    1145                 1150                 1155

Glu Phe  Ile Ala Ser Phe Tyr  Lys Asn Asp Leu Ile  Lys Ile Asn
    1160                 1165                 1170

Gly Glu  Leu Tyr Arg Val Ile  Gly Val Asn Asn Asp  Leu Leu Asn
    1175                 1180                 1185

Arg Ile  Glu Val Asn Met Ile  Asp Ile Thr Tyr Arg  Glu Tyr Leu
    1190                 1195                 1200

Glu Asn  Met Asn Asp Lys Arg  Pro Pro His Ile Ile  Lys Thr Ile
    1205                 1210                 1215

Ala Ser  Lys Thr Gln Ser Ile  Lys Lys Tyr Ser Thr  Asp Ile Leu
    1220                 1225                 1230

Gly Asn  Leu Tyr Glu Val Lys  Ser Lys Lys His Pro  Gln Ile Ile
    1235                 1240                 1245

Lys Lys  Gly Gly Ser Ser Gly  Gly Ser Thr Asn Leu  Ser Asp Ile
    1250                 1255                 1260

Ile Glu  Lys Glu Thr Gly Lys  Gln Leu Val Ile Gln  Glu Ser Ile
    1265                 1270                 1275

Leu Met  Leu Pro Glu Glu Val  Glu Glu Val Ile Gly  Asn Lys Pro
    1280                 1285                 1290

Glu Ser  Asp Ile Leu Val His  Thr Ala Tyr Asp Glu  Ser Thr Asp
    1295                 1300                 1305

Glu Asn  Val Met Leu Leu Thr  Ser Asp Ala Pro Glu  Tyr Lys Pro
    1310                 1315                 1320

Trp Ala  Leu Val Ile Gln Asp  Ser Asn Gly Glu Asn  Lys Ile Lys
    1325                 1330                 1335

Met Leu  Ser Gly Gly Ser Pro  Lys Lys Lys Arg Lys  Val Gly Ser
    1340                 1345                 1350

Tyr Pro  Tyr Asp Val Pro Asp  Tyr Ala
    1355                 1360
```

<210> SEQ ID NO 51
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: sgRNA DMD EXON50 5'SS

<400> SEQUENCE: 51
acttacaggc tccaatagtg 20

<210> SEQ ID NO 52
<211> LENGTH: 103
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: sgRNA Backbond sequence
<220> FEATURE:
<221> NAME/KEY: misc_feature
<222> LOCATION: (1)..(20)
<223> OTHER INFORMATION: n is a, c, g or t

<400> SEQUENCE: 52
nnnnnnnnnn nnnnnnnnnn gttatagtac tctggaaaca gaatctacta taacaaggca 60
aaatgccgtg tttatctcgt caacttgttg gcgagatttt ttt 103

<210> SEQ ID NO 53
<211> LENGTH: 26
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: intron-exon junction sequence

<400> SEQUENCE: 53
ctcactttcc taccttaggt gtttca 26

<210> SEQ ID NO 54
<211> LENGTH: 26
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: intron-exon junction sequence

<400> SEQUENCE: 54
ccaggcagca atgctatctc aggttt 26

<210> SEQ ID NO 55
<211> LENGTH: 11
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: exon-intron junction sequence

<400> SEQUENCE: 55
tgctatctca g 11

<210> SEQ ID NO 56
<211> LENGTH: 27
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: exon/intron junction sequence

<400> SEQUENCE: 56
ctggagattg gatcacaggt ataattc 27

<210> SEQ ID NO 57
<211> LENGTH: 27
<212> TYPE: DNA
<213> ORGANISM: Artificial Sequence
<220> FEATURE:
<223> OTHER INFORMATION: synthesized
<220> FEATURE:

<221> NAME/KEY: misc_feature
<223> OTHER INFORMATION: exon/intron junction sequence

<400> SEQUENCE: 57
tgagctggag attggatcac aggtata 27

<210> SEQ ID NO 58
<211> LENGTH: 26
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: exon/intron junction sequence

<400> SEQUENCE: 58
cccccaggga gcactaagcg aggtaa 26

<210> SEQ ID NO 59
<211> LENGTH: 26
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: intron-exon junction sequence

<400> SEQUENCE: 59
cctttccttg cctctttcct agcact 26

<210> SEQ ID NO 60
<211> LENGTH: 26
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: intron-exon junction sequence

<400> SEQUENCE: 60
ccccccattt cctacagaac gacctg 26

<210> SEQ ID NO 61
<211> LENGTH: 29
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: intron-exon junction sequence

<400> SEQUENCE: 61
cctctggacg gatgttgctc ccctagatt 29

<210> SEQ ID NO 62
<211> LENGTH: 26
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: intron-exon junction sequence

<400> SEQUENCE: 62
ctcaccaagt ctggcaggta ggaggc 26

<210> SEQ ID NO 63
<211> LENGTH: 26
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: exon/intron junction sequence

<400> SEQUENCE: 63
cctaccctaa accttacaga tagctc 26

<210> SEQ ID NO 64
<211> LENGTH: 26
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: exon/intron junction sequence

<400> SEQUENCE: 64
ctcacggagt ctggcaggta gggccc 26

<210> SEQ ID NO 65
<211> LENGTH: 26
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: intron-exon junction sequence

<400> SEQUENCE: 65
cctgctcgtg gaagatttcg gtaaga 26

<210> SEQ ID NO 66
<211> LENGTH: 26
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: intron-exon junction sequence

<400> SEQUENCE: 66
ctttcctttc ctcatcgcag gtgtca 26

<210> SEQ ID NO 67
<211> LENGTH: 12
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: GANAB exon 6 multiple Cs region

<400> SEQUENCE: 67
ctcctgcccc ag 12

<210> SEQ ID NO 68
<211> LENGTH: 12
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: GANAB exon 6 multiple Cs region with Cs converting to Ts

<400> SEQUENCE: 68
tttttgtttt ag 12

<210> SEQ ID NO 69
<211> LENGTH: 26
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: exon/intron junction sequence

<400> SEQUENCE: 69
ctcctgcccc agtttctcgg ataagg 26

<210> SEQ ID NO 70
<211> LENGTH: 28
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: exon/intron junction sequence

<400> SEQUENCE: 70
ccactgattc agtgagctgg agattgga 28

<210> SEQ ID NO 71
<211> LENGTH: 31
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: reference sequence

<400> SEQUENCE: 71
gccactgatt cagtgagctg gagattggat c 31

<210> SEQ ID NO 72
<211> LENGTH: 23
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: exon/intron junction sequence

<400> SEQUENCE: 72
ccactattgg agcctgtaag tat 23

<210> SEQ ID NO 73
<211> LENGTH: 24
<212> TYPE: DNA

<213> ORGANISM: Artificial Sequence
<220> FEATURE:
<223> OTHER INFORMATION: synthesized
<220> FEATURE:
<221> NAME/KEY: misc_feature
<223> OTHER INFORMATION: DMD gene fragment

<400> SEQUENCE: 73
actcagccag tgaagaggaa gtta 24

<210> SEQ ID NO 74
<211> LENGTH: 24
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: DMD gene fragment

<400> SEQUENCE: 74
actattggag cctgcaacaa tgca 24

<210> SEQ ID NO 75
<211> LENGTH: 24
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: DMD gene fragment

<400> SEQUENCE: 75
actcagccag tgaaggcaac aatg 24

<210> SEQ ID NO 76
<211> LENGTH: 35
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: exon/intron junction sequence

<400> SEQUENCE: 76
actgaccact attggagcct gtaagtatac tggat 35

<210> SEQ ID NO 77
<211> LENGTH: 26
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: off-target sequence

<400> SEQUENCE: 77
cttttcaaat tccaatagtg aggagt 26

<210> SEQ ID NO 78
<211> LENGTH: 26
<212> TYPE: DNA
<213> ORGANISM: Artificial Sequence
<220> FEATURE:
<223> OTHER INFORMATION: synthesized
<220> FEATURE:

```
<221> NAME/KEY: misc_feature
<223> OTHER INFORMATION: on-target sequence

<400> SEQUENCE: 78

acttacaggc tccaatagtg gtcagt                                   26
```

METHOD FOR MODULATING RNA SPLICING BY INDUCING BASE MUTATION AT SPLICE SITE OR BASE SUBSTITUTION IN POLYPYRIMIDINE REGION

CROSS REFERENCE TO RELATED APPLICATIONS

This application is a U.S. National Phase application under 35 U.S.C. 371 of International Application No. PCT/CN2018/096810, filed Jul. 24, 2018, which claims priority to and the benefit of Chinese Application No. CN201710611651.8 filed Jul. 25, 2017, each of which is incorporated herein by reference in their entirety.

TECHNICAL FIELD

The disclosure relates to a method for modulating RNA splicing by inducing base mutation at splice site or base substitution in polypyrimidine region.

INCORPORATION OF SEQUENCE LISTING

This application contains a sequence listing submitted in Computer Readable Form (CRF). The CFR file containing the sequence listing entitled "SequenceListing.txt", which was created on Jan. 5, 2026, and is 181,013 bytes in size. The information in the sequence listing is incorporated herein by reference in its entirety.

BACKGROUND

The correct expression of eukaryotic genes requires the removal of introns in the pre-mRNA and the splicing of exons to form mature mRNA. More than 98% of introns are excised by a highly dynamic protein complex, the spliceosome. The spliceosome consists of more than 150 small nuclear ribonucleoproteins (snRNPs), such as U1, U2, U4, U5, and U6. During the splicing process, the U1 snRNP recognizes the GU sequence at the 5' splice site of the intron, splicing factor 1 (SF1) binds to the bifurcation point of the intron, and the 35KD subunit of the U2 auxiliary factor (U2AF) binds to the AG sequence at the 3' splice site of the intron, and its 65KD subunit binds to the polypyrimidine region sequence to complete the exon recognition process; then U5 and U6 proteins catalyze the intron removal process by regulating RNA structure reconstruction and RNA-protein interaction. The RNA splicing process plays an important role in the regulation of gene expression. Studies have found that 15% of heritable human diseases are caused by abnormal processing of pre-mRNAs, therefore the RNA splicing process can be a possible therapeutic target for these diseases. For example, the use of antisense oligonucleotides (ASO) to regulate RNA splicing of a disease-related gene can alleviate Duchenne muscular dystrophy and spinal muscular atrophy.

In addition to intron splicing, 75% of human genes undergo alternative RNA splicing during expression, greatly increasing the abundance of the human proteome. However, functions of most alternative splicing protein isoforms are not clear due to the lack of convenient and effective methods to regulate the alternative splicing process.

Antisense oligonucleotides can bind to cis-acting elements of RNA (such as exonic splicing enhancers) to block splicing of exons, but the use of antisense oligonucleotides to regulate splicing requires careful design and strict screening, and also requires continuous administration during treatment. Meanwhile, the synthesis of the antisense oligonucleotides is time-consuming and very expensive. Therefore, there is a dire need to provide a one-time cure for these diseases.

SUMMARY

Provided herein is a method for regulating RNA splicing of a gene of interest in a cell, characterized in that the method includes expressing targeting cytosine deaminase in the cell to induce mutation of the 3' splice site AG of an intron of interest of the gene of interest in the cell to AA, or mutation of the 5' splice site GT of an intron of interest of the gene of interest in the cell to AT, or mutation of multiple Cs in the polypyrimidine region of an intron of interest of the gene of interest in the cell to Ts.

In one or more embodiments, the targeting cytosine deaminase used in the methods described herein may be selected from the group consisting of:

(1) a fusion protein of a cytosine deaminase, or a fragment or mutant thereof retaining enzyme activity, and a CRISPR-associated (Cas) enzyme with helicase activity and partial or no nuclease activity;

(2) a fusion protein of a cytosine deaminase, or a fragment or mutant thereof retaining enzyme activity, and a transcription activator-like effector nuclease (TALEN) protein that specifically recognizes a target sequence;

(3) a fusion protein of a cytosine deaminase, or a fragment or mutant thereof retaining enzyme activity, and a zinc finger protein that specifically recognizes a target sequence;

(4) a fusion protein of a cytosine deaminase, or a fragment or mutant thereof retaining enzyme activity, and a CRISPR from prevotella and francisella (Cpf) enzyme with helicase activity and partial or no nuclease activity; and (5) a fusion protein of a cytosine deaminase, or a fragment or mutant thereof retaining enzyme activity, and an argonaute (Ago) protein.

In one or more embodiments, the targeting cytosine deaminase is the fusion protein of a cytosine deaminase, or a fragment or mutant thereof retaining enzyme activity, and a Cas enzyme with helicase activity and partial or no nuclease activity, or the fusion protein of a cytosine deaminase, or a fragment or mutant thereof retaining enzyme activity, and a Cpf enzyme with helicase activity and partial or no nuclease activity; the method includes expressing the targeting cytosine deaminase and a single guide RNA (sgRNA) in the cell, wherein the sgRNA is specifically recognized by the Cas enzyme or Cpf enzyme and binds to the sequence having a splice site of an intron of interest of the gene of interest, or binds to the complementary sequence of a polypyrimidine region of interest.

In one or more embodiments, the targeting cytosine deaminase is the fusion protein of a cytosine deaminase, or a fragment or mutant thereof retaining enzyme activity, and an Ago protein; the method includes a step of expressing in the cell the targeting cytosine deaminase and a guide DNA (gDNA) recognized by the Ago protein.

In one or more embodiments, provided herein is a method of regulating RNA splicing of a gene of interest in a cell, the method comprising a step of expressing in the cell (1) a fusion protein of a Cas protein with helicase activity and partial or no nuclease activity, and cytosine deaminase activation-induced cytidine deaminase (AID) or a mutant thereof, and (2) an sgRNA; wherein, the Cas protein recognition region of the sgRNA is specifically recognized by the Cas protein, and the sgRNA binds to the sequence having a splice site of an intron of interest of the gene of interest, or binds to the complementary sequence of a polypyrimidine region of interest.

In one or more embodiments, the sgRNA binds to the sequence having the 5' splice site of the intron of interest of the gene of interest, and the fusion protein mutates the GT at the 5' splice site to AT, thereby inducing exon skipping, activating alternative splice sites, inducing mutually exclusive exon switching or intron retention.

In one or more embodiments, the sgRNA binds to the sequence having the 3' splice site of the intron of interest of the gene of interest, and the fusion protein mutates the AG at the 3' splice site to AA, thereby inducing exon skipping, activating alternative splice sites, inducing mutually exclusive exon switching or intron retention.

In one or more embodiments, the sgRNA binds to the complementary sequence of the polypyrimidine region of interest, and induces the C at the polypyrimidine region to T, thereby enhancing exon inclusion.

In one or more embodiments, RNA splicing of the gene of interest in the cell is regulated by transferring expression vector(s) of the fusion protein and the sgRNA into the cell.

In one or more embodiments, the method further includes a step of simultaneously transferring an expression plasmid of uracil glycosylase inhibitor (UGI).

In one or more embodiments, the method further includes a step of simultaneously transferring expression plasmid(s) of a fusion protein of a nuclease-deficient or nuclease-partially-deficient Cas9 protein, AID or a mutant thereof, and an UGI.

In one or more embodiments, the fusion protein and AID, a fragment or a mutant thereof are as described in any part or any embodiment herein.

In one or more embodiments, the cell of interest and the gene of interest are as described in any part or any embodiment herein.

In certain embodiments, provided herein is a method for inducing exon skipping, the method comprising a step of expressing in the cell (1) a fusion protein of a Cas protein with helicase activity and partial or no nuclease activity, cytosine deaminase AID or a mutant thereof, and an optional UGI fusion protein, and (2) an sgRNA; wherein, the Cas protein recognition region of the sgRNA is specifically recognized by the Cas protein, and the sgRNA binds to the sequence having a splice site of an intron of interest of the gene of interest.

In certain embodiments, provided herein is a method for activating alternative splice site(s), the method comprising a step of expressing in the cell (1) a fusion protein of a Cas protein with helicase activity and partial or no nuclease activity, cytosine deaminase AID or a mutant thereof, and an optional UGI fusion protein, and (2) an sgRNA; wherein, the Cas protein recognition region of the sgRNA is specifically recognized by the Cas protein, and the sgRNA binds to the sequence having a splice site of an intron of interest of the gene of interest, wherein the intron of interest has alternative splice site(s) nearby.

In certain embodiments, provided herein is a method for inducing mutually exclusive exon switching, the method comprising a step of expressing in the cell (1) a fusion protein of a Cas protein with helicase activity and partial or no nuclease activity, cytosine deaminase AID or a mutant thereof, and optional an UGI, and (2) an sgRNA; wherein, the Cas protein recognition region of the sgRNA is specifically recognized by the Cas protein, and the target binding region of the sgRNA comprises the sequence of a splice site of an intron of interest of the gene of interest, wherein the gene of interest is selected from a group consisting of pyruvate kinase M isoforms (PKMs).

In certain embodiments, provided herein is a method for inducing intron retention, the method comprising a step of expressing in the cell (1) a fusion protein of a Cas protein with helicase activity and partial or no nuclease activity, cytosine deaminase AID or a mutant thereof, and optional an UGI fusion protein, and (2) an sgRNA; wherein, the Cas protein recognition region of the sgRNA is specifically recognized by the Cas protein, and the sgRNA comprises a splice site of the intron of interest, wherein the intron of interest is short in length (<150 bp) and rich in G/C bases.

In certain embodiments, provided herein is a method for enhancing exon inclusion, the method comprising a step of expressing in the cell (1) a fusion protein of a Cas protein with helicase activity and partial or no nuclease activity, cytosine deaminase AID or a mutant thereof, and optional an UGI, and (2) an sgRNA; wherein, the Cas protein recognition region of the sgRNA is specifically recognized by the Cas protein, and the sgRNA comprises the complementary sequence of the polypyrimidine region upstream of the exon of interest.

Also provided herein is a fusion protein that contains a Cas protein with helicase activity and partial or no nuclease activity and cytosine deaminase AID or a mutant thereof.

In one or more embodiments, the fusion protein herein also contains UGI.

Also provided herein is a fusion protein for generating a point mutation in a cell, or for regulating RNA splicing of a gene of interest in a cell, or for inducing exon skipping, activating alternative splicing sites, inducing mutually exclusion exon switching, inducing intron retention, or enhancing exon inclusion in a cell of interest, wherein the fusion protein contains a Cas protein with helicase activity and partial or no nuclease activity and cytosine deaminase AID or a mutant thereof, and optional a linker sequence, a nuclear localization sequence, and UGI.

Also provided herein is a method for treating a disease using the method for regulating RNA splicing described herein.

Also provided herein is use of the fusion protein described herein or its expression vector and the corresponding sgRNA or its expression vector in the preparation of a kit for regulating RNA splicing, as well as a kit comprising the fusion protein described herein or its expression and the corresponding sgRNA or its expression vector.

BRIEF DESCRIPTION OF DRAWINGS

As shown in FIG. 1, 293T cells were transfected with the expression plasmid(s) of AIDx-nCas9-UGI and the sgRNA targeting Stat3 exon 23 (E23-3'SS-) or sgRNA targeting AAVS1 (Ctrl). Intron-exon junctions (SEQ ID NO: 60) were amplified from DNA (top 2 panels) or cDNA (bottom 2 panels) and analyzed by high-throughput sequencing. The base composition of nucleotides having detectable mutations (>0.1%) is depicted. Note that TAM also induced two mutations in exon 23, which is much less than cDNA (26% and 6%) of cDNA (54% and 16%). The data are representative of two independent experiments. (C) TAM enhanced the use of the distal 3'SS in Stat3 exon 23. The splicing junctions were amplified from cDNA and analyzed by high-throughput sequencing. The Figure shows the coverage and percentage of each splicing junction of the cells treated with control sgRNA (top panel) or E23-3'SS sgRNA (bottom panel). Intersections that account for more than 1% of total transcripts are depicted. The count and percentage (in parentheses) of the junction readings are depicted on the top of each junction arc. Note that only in cells treated with Stat3-E23-3'SS, sgRNAs were cryptic splice sites activated in about 10% of the transcripts. The data are representative of two independent experiments. (E-F) TAM converted Stat3α to Stat3β. The expression of Stat3α and Stat3β in TAM treated cells was detected by RT-PCR (D) and isoform-specific real-time fluorescence quantitative PCR (E), and the ratio of Stat3α to Stat3β was determined (F).

DETAILED DESCRIPTION

Figure 1:
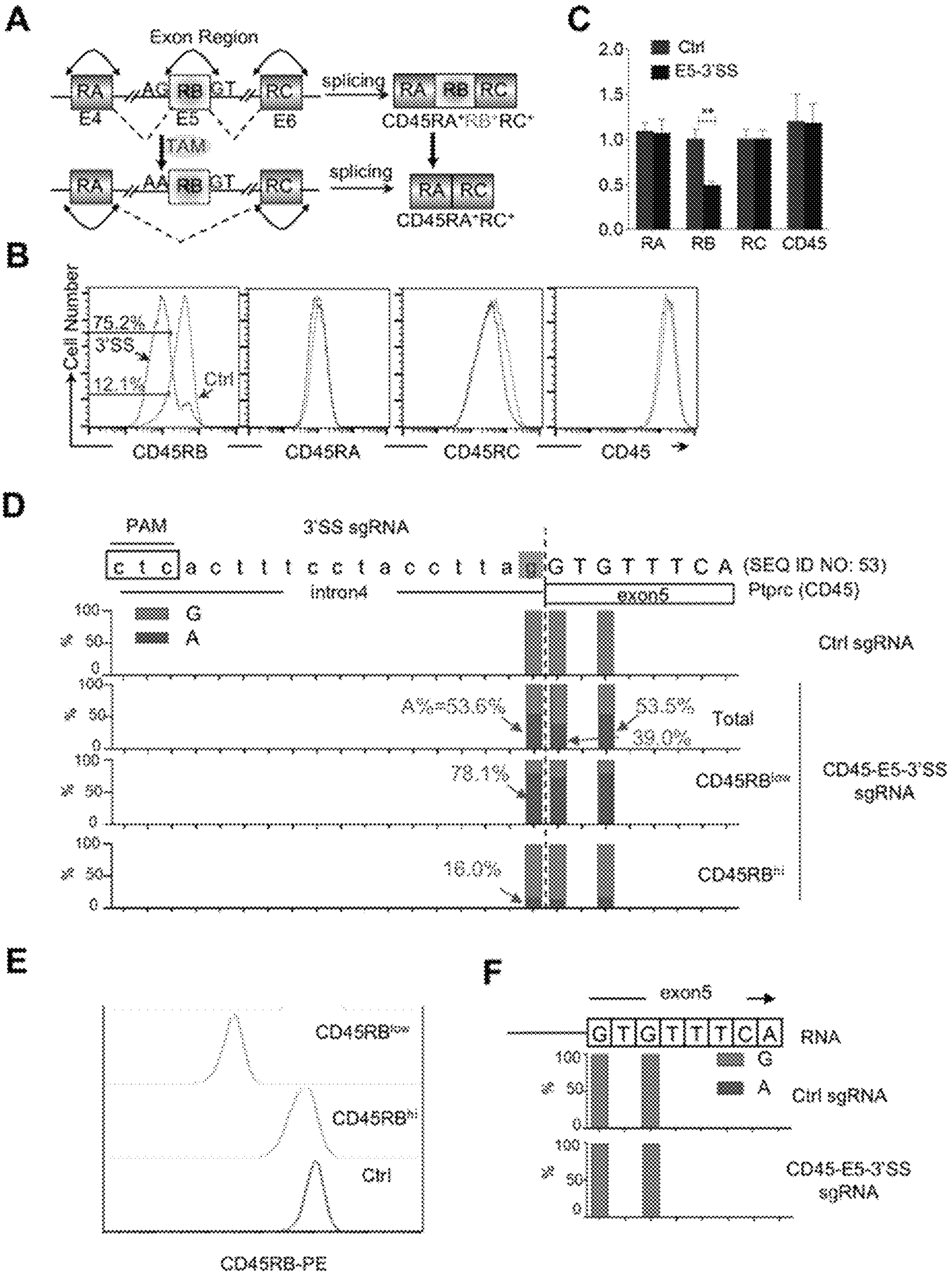
FIG. 1: Targeted AID-mediated mutagenesis (TAM) induced exon 5 skipping in cluster of differentiation 45 (CD45) by converting the invariant guanine to adenine at the 3' splice site. (A) A schematic diagram of using TAM to convert guanine to adenine at the 3' splice site of CD45 RB exon and induce exon skipping. In WT Raji cells, combined splicing exon 5 of CD45 produced the longest CD45 isoform ($CD45RA^+RB^+RC^+$, top panel); TAM converted the AG dinucleotide to AA at 3'SS of exon 5, thereby eliminating this splice site and disrupting exon recognition, leading exon 5 skipping and production of the CD45 isoform lacking the CD45RB ($CD45RA^+RC^+$, botton panel). (B, C) TAM caused CD45RB exon skipping. Raji cells were transfected with the expression plasmid(s) of AIDx-nickase Cas9 (nCas9)-UGI and the targeting sgRNA (CD45-E5-3'SS) or a control sgRNA targeting the AAVS1 (Ctrl). Seven days after transfection, expression of the targeted exon (CD45RB), its upstream exon (exon 4, CD45RA), downstream exon (Exon 6, CD45RC) and total CD45 was determined by flow cytometry using exon-specific antibodies (B); or the expression of the corresponding exons was detected by exon-specific real-time polymerase chain reaction (PCR) (C). The data are representative (B) or summary (C) of two independent experiments. **, p<0.01 in Student's t test. (D) In CD45RB$^{low}$ cells, the G>A mutation at the 3'SS was enriched. Intron-exon junctions were amplified from the genomic DNA of the cells shown in B and the sorted CD45RB$^{hi}$ and CD45RB$^{low}$ cells from TAM-treated cells. The amplicons were analyzed by high-throughput sequencing with over 8000× coverage. The base composition of each nucleotide having a detectable mutation (mutant reading/WT reading >0.1%) is depicted, and the percentage of G>A conversion of the mutated Gs is marked. The locations of the sgRNA and protospacer adjacent motif (PAM) sequences are shown on the top of the intron-exon junction sequence (SEQ ID NO: 53). Intron/exon junctions are depicted using dashed lines. The data are representative of two independent experiments. (E) Flow cytometric analysis of CD45RB expression in control Raji cells or sorted CD45RB$^{hi}$ and CD45RB$^{low}$ cells from TAM-treated cells. (F) TAM induced CD45RB skipping without changing the coding sequence of CD45. As in D, the exon-intron junctions were amplified from cDNA and analyzed for base substitution by high-throughput sequencing. Note that the two exon mutations are not detectable in the cDNA of TAM-treated cells as compared with genomic DNA.

It should be understood that, within the scope of the present disclosure, the above technical features of the present disclosure and the technical features specifically described in the following (e.g., Examples) can be combined with each other, thereby forming preferred technical solution(s).

In this disclosure, by generating a point mutation in a cell, especially by mutating the 3' splice site AG of an intron of interest of a gene of interest in the cell to AA, or mutating the 5' splice site GT of an intron of interest of a gene of interest in the cell to AT, or mutating the multiple Cs (for example, 2-10) in the polypyrimidine region of an intron of interest of a gene of interest in the cell to Ts, RNA splicing of the gene of interest in the cell can be regulated, so that to induce exon skipping, activate alternative splice sites, induce mutually exclusive exon switching, induce intron retention or enhance exon inclusion. "Regulating" herein means to change the conventional splicing manner of the RNA.

The present disclosure can be implemented using targeting cytosine deaminase. In this disclosure, the targeting cytosine deaminase is constructed by fusing cytosine deaminase with a protein with a targeting effect.

As used herein, cytosine deaminase refers to various enzymes with cytosine deaminase activity, including but not limited to enzymes of the apolipoprotein B mRNA editing enzyme catalytic polypeptide-like (APOBEC) family, such as APOBEC-2, AID, APOBEC-3A, APOBEC-3B, APOBEC-3C, APOBEC-3DE, APOBEC-3G, APOBEC-3F, APOBEC-3H, APOBEC4, APOBECI and *Petromyzon marinus* cytidine deaminase 1 (pmCDA1). The cytosine deaminase suitable for use herein can be derived from any species, preferably mammalian, especially human cytosine deaminase. It is preferred that the cytosine deaminase suitable for use herein is an activated cytosine deaminase, such as a human-derived activated cytosine deaminase. The cytosine deaminases of the APOBEC family are RNA editing enzymes with a nuclear localization signal at the N-terminus and a nuclear export signal at the C-terminus. The catalytic domain of these enzymes is shared by the APOBEC family. Generally, the N-terminal structure is considered necessary for somatic hypermutation (SHM). The function of cytosine deaminases is to deaminate cytosine and transform cytosine into uracil, and then DNA repairing can transform uracil into other bases. It should be understood that the cytosine deaminases well known in the art or fragments or mutants thereof that retain the biological activity of deaminating cytosine and converting cytosine into uracil can be used herein.

In certain embodiments, AID is used herein as the cytosine deaminase in the targeting cytosine deaminase. Amino acid residues 9-26 of AID are nuclear localization signal (NLS) domain, especially amino acid residues 13-26, which are involved in DNA binding; amino acid residues 56-94 are catalytic domain; amino acid residues 109-182 are APOBEC-like domain; amino acid residues 193-198 are nuclear export signal (NES) domain; amino acid residues 39-42 interact with catenin-like protein 1 (CTNNBL1); and amino acid residues 113-123 are hotspot recognition loop.

The full-length AID (as shown in SEQ ID NO: 25, amino acids 1457-1654), or a fragment of AID can be used in this disclosure. Preferably, the fragment includes at least the NLS domain, the catalytic domain, and the APOBEC-like domain. Therefore, in certain embodiments, the fragment comprises at least amino acid residues 9-182 of AID (i.e., amino acid residues 1465-1638 of SEQ ID NO: 25). In other embodiments, the fragment comprises at least amino acid residues 1-182 of AID (i.e., amino acid residues 1457-1638 of SEQ ID NO: 25). For example, in certain embodiments, the AID fragment used herein consists of amino acid residues 1-182, amino acid residues 1-186, or amino acid residues 1-190. Therefore, in certain embodiments, the AID fragment used herein consists of amino acid residues 1457-1638 of SEQ ID NO: 25, amino acid residues 1457-1642 of SEQ ID NO: 25, or amino acid residues 1457-1646 of SEQ ID NO: 25.

A variant of AID that retains its cytosine deaminase activity (i.e., the biological activity of deaminating cytosine and converting cytosine into uracil) can also be used herein. For example, such variants may have 1-10, such as 1-8, 1-5, or 1-3 amino acid variations, including amino acid deletions, substitutions, and mutations, with respect to the sequence of the wild-type AID. Preferably, these amino acid variations do not present in the above-mentioned NLS domain, catalytic domain, or APOBEC-like domain, or even if they occur in these domains, they do not affect the original biological functions of these domains. For example, it is preferable that these variations do not occur at the amino acid residue 24, 27, 38, 56, 58, 87, 90, 112, 140 of the AID amino acid sequence. In certain embodiments, these variations also do not occur within amino acids 39-42, amino acids 113-123. Thus, for example, variations can occur in amino acids 1-8, amino acids 28-37, amino acids 43-55 and/or amino acids 183-198. In certain embodiments, variations occur at amino acids 10, 82, and 156. For example, substitutions occur at amino acids 10, 82, and 156, which may be K10E, T82I, and E156G. In these embodiments, the amino acid sequence of the exemplary AID mutant contains or consists of the amino acid sequence shown as residues 1447-1629 of SEQ ID NO: 31. Examples of other AIDs, fragments or mutants thereof can refer to CN201710451424.3, the entire contents of which are incorporated herein by reference.

Herein, the protein with a targeting effect may be a protein known in the art that can target a gene of interest in the cell genome, including but not limited to a TALEN protein that specifically recognizes the target sequence, a zinc finger protein that recognizes the target sequence by mutation, an Ago protein, a Cpf enzyme and a Cas enzyme. This disclosure can be implemented using TALEN proteins, zinc finger proteins, Ago proteins, and Cpf enzymes and Cas enzymes, which are well known in the art.

Therefore, in certain embodiments, the targeting cytosine deaminase suitable for use herein may be selected from the group consisting of:

(1) a fusion protein of a cytosine deaminase, or a fragment or mutant thereof retaining enzyme activity, and a Cas enzyme with helicase activity and partial or no nuclease activity;

(2) a fusion protein of a cytosine deaminase, or a fragment or mutant thereof retaining enzyme activity, and a TALEN protein that specifically recognizes a target sequence;

(3) a fusion protein of a cytosine deaminase, or a fragment or mutant thereof retaining enzyme activity, and a zinc finger protein that specifically recognizes a target sequence;

(4) a fusion protein of a cytosine deaminase, or a fragment or mutant thereof retaining enzyme activity, and a Cpf enzyme with helicase activity and partial or no nuclease activity; and (5) a fusion protein of a cytosine deaminase, or a fragment or mutant thereof retaining enzyme activity, and a Ago protein.

When Cpf enzymes are used, it is preferable to use a Cpf enzyme in which nuclease activity is partially or completely absent but helicase activity retains. The Cpf enzyme, under the guidance of its recognized sgRNA, binds to the specific DNA sequence, allowing the cytosine deaminase fused thereto to perform the mutations described herein. The Ago protein needs to bind to the specific DNA sequence under the guidance of its recognized gDNA.

In certain embodiments, the targeting cytosine deaminase AID-mediated gene mutation technology (TAM) is used herein to mutate guanine to adenine at the splice site of the intron, specifically block the exon recognition process, and regulate the alternative splicing process of endogenous mRNA. The TAM technique herein uses a fusion protein of a Cas protein lacking nuclease activity and cytosine deaminase AID, an active fragment or a mutant thereof. Under the guidance of sgRNA, the fusion protein is recruited to the specific DNA sequence, wherein AID, active fragments or mutants thereof mutates guanine (G) into adenine (A), or mutates cytosine (C) into thymine (T).

CRISPR (Clustered Regularly Interspaced Short Palindromic Repeats) is a gene editing system of bacteria to resist viruses or evade mammalian immune responses. The system has been modified and optimized, and has been widely used in in vitro biochemical reactions, gene editing of cells and individuals. Generally, the complex formed by the Cas protein with endonuclease activity (also called Cas enzyme) and its specifically recognized sgRNA is complementary paired with the template strand in the target DNA through the matching region (i.e., target binding region) of the sgRNA, and the double-stranded DNA is cut at a specific location by Cas. The above-mentioned characteristics of Cas/sgRNA are used in this disclosure, that is, the Cas is localized to the desired location through the specific binding of the sgRNA to the target, where the AID or its active fragment or mutant in the fusion protein mutates guanine (G) to adenine (A), or cytosine (C) to thymine (T).

The Cas protein suitable for this disclosure having helicase activity and partial (only having DNA single-strand break ability) or no nuclease activity (no DNA double-strand break ability), especially those having helicase activity and partial or no endonuclease activity, can be derived from various Cas proteins well known in the art and variants thereof, including but not limited to Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, their homologues or modified variants.

In some embodiments, a Cas9 enzyme lacking nuclease activity together with its specifically recognized single-stranded sgRNA are used. Cas9 enzymes may be Cas9 enzymes from different species, including but not limited to Cas9 from *Streptococcus pyogenes* (SpCas9), Cas9 from *Staphylococcus aureus* (SaCas9), and Cas9 from *Streptococcus thermophilus* (St1Cas9), etc. Various variants of the Cas9 enzyme can be used, provided that the Cas9 enzyme can specifically recognize its sgRNA and lack nuclease activity.

Cas proteins lacking nuclease activity can be prepared by methods well known in the art. These methods include, but are not limited to, deleting the entire catalytic domain of the endonuclease in the Cas proteins, or mutating one or several amino acids in the catalytic domain, thereby producing Cas proteins lacking nuclease activity. The mutation may be deletion or substitution of one or several (for example, 2 or more, 3 or more, 4 or more, 5 or more, 10 or more to the entire catalytic domain) amino acid residues, or insertion of one or several (e.g., 1 or more, 2 or more, 3 or more, 4 or more, 5 or more, 10 or more, or 1-10, 1-15) new amino acids residues. Conventional methods in the art can be used to perform the above deletion of the domain or mutation of amino acid residue, and to detect whether the mutated Cas protein has nuclease activity. For example, for Cas9, the two endonuclease catalytic domains RuvC1 and HNH can be mutated separately, e.g., the amino acid 10 asparagine of the enzyme (in RuvC1 domain) is mutated to alanine or other amino acids, the amino acid 841 histidine (in HNH domain) is mutated to alanine or other amino acids. These two mutations make Cas9 lose endonuclease activity. Preferably, the Cas enzyme has no nuclease activity at all. In one or more embodiments, the amino acid sequence of the nuclease-activity-free Cas9 enzyme used herein is shown as residues 42-1452 of SEQ ID NO: 25. In other embodiments, the Cas enzyme used herein partially lacks nuclease activity, i.e., the Cas enzyme can cause DNA single-strand breaks. A representative example of such Cas enzymes can be shown as amino acid residues 42-1419 of SEQ ID NO: 33. In other embodiments, the amino acid sequence of the Cas enzyme used herein is shown as residues 199-1566 of SEQ ID NO: 23, or is shown as residues 199-1262 of SEQ ID NO: 50. Examples of other Cas enzymes can refer to CN201710451424.3, the entire contents of which are incorporated herein by reference.

The Cas/sgRNA complex's function requires a protospacer adjacent motif (PAM) in the non-template strand (3' to 5') of the DNA. The corresponding PAMs of different Cas enzymes are not exactly the same. For example, generally, the PAM for SpCas9 is NGG (SEQ ID NO: 34); the PAM for SaCas9 is NNGRR (SEQ ID NO: 35); the PAM for St1Cas9 is NNAGAA (SEQ ID NO: 36); wherein N is A, C, T or G, and R is G or A.

In certain preferred embodiments, the PAM for SaCas9 is NNGRRT (SEQ ID NO: 37). In certain preferred embodiments, the PAM for SpCas9 is TGG (SEQ ID NO: 38); in certain preferred embodiments, the PAM for SaCas9 enzyme KKH mutant is NNNRRT (SEQ ID NO: 39); wherein, N is A, C, T or G, and R is G or A.

Generally, sgRNA contains two parts: target binding region and protein recognition region (such as Cas enzyme recognition region or Cpf enzyme recognition region). The target binding region and the protein recognition region are usually connected in a 5' to 3' direction. The length of the target binding region is usually 15 to 25 bases, more usually 18 to 22 bases, such as 20 bases. The target binding region specifically binds to the template strand of DNA, thereby recruiting the fusion protein to a predetermined site. Generally, the opposite complementary region of the sgRNA binding region on the DNA template strand is immediately adjacent to PAM, or separated from PAM by several bases (for example, within 10, or within 8, or within 5 bases). Therefore, when designing sgRNA, the enzyme's PAM is determined according to the used splicing enzyme (such as Cas enzyme), and then the non-template strand of DNA is searched for a site that can be used as PAM, and then a fragment of 15 bp-20 bp in length, more usually 18 bp-22 bp in length, which is downstream from the PAM site of the non-template strand (3' to 5') and immediately adjacent to the PAM site or separated from the PAM site within 10 bp (e.g., within 8 bp or 5 bp) serves as the sequence of the target binding region of sgRNA. The protein recognition region of sgRNA is determined according to the used splicing enzyme, which is known by those skilled in the art.

Therefore, the sequence of the target binding region of the sgRNA herein comprises the fragment of 15 bp-20 bp in length, more usually 18 bp-22 bp in length, downstream from the PAM site recognized by the selected splicing enzyme (such as Cas enzyme or Cpf enzyme) and immediately adjacent to the PAM site or separated from the PAM site within 10 bp (e.g., within 8 bp or 5 bp); its protein recognition region is specifically recognized by the selected splicing enzyme.

Given that the purpose of this disclosure is to mutate guanine to adenine at the intron splice site, or mutate C to T in the polypyrimidine strand upstream of the 3' splice site, it should be considered whether a PAM sequence is present near the splice site, and the distance between the PAM sequence and the splice site(s), when designing an sgRNA for this disclosure. Therefore, in general, the sgRNA binds to the sequence containing the splice site(s) of the intron of interest of the gene of interest, or to the complementary sequence of the polypyrimidine region of interest. Alternatively, the target binding region of the sgRNA contains the complementary sequence of the splice site(s) of the intron of interest of the gene of interest, or contains the sequence of the polypyrimidine region of the intron of interest of the gene of interest.

The sgRNA can be prepared by conventional methods in the art, for example, synthesized by conventional chemical synthesis methods. The sgRNA can also be transferred into cells via an expression vector, and expressed in the cells; or it can be introduced into animals/humans via adeno-associated viruses. The expression vector of the sgRNA can be constructed using methods well known in the art.

In certain embodiments, sgRNA sequences or complementary sequences thereof are also provided herein, which include a target binding region and a protein recognition region, wherein the target binding region binds to a sequence containing a splice site of the intron of interest of the gene of interest, or to a complementary sequence of the polypyrimidine region of interest. Generally, the target binding region is 15-25 bp in length, such as 18-22 bp, preferably 20 bp. In certain embodiments, the target binding region of the sgRNA binds to the sequence in DMD exon 50 having the 3' splice site; preferably, the target binding region of the sgRNA is as shown in SEQ ID NO: 17 or 51.

The targeting cytosine deaminase used herein is preferably a fusion protein of the aforementioned Cas enzyme and the aforementioned AID or fragments or mutants thereof. The Cas enzyme is usually at the N-terminus of the amino acid sequence of the fusion protein, and the AID or its fragment or mutant is at the C-terminus. Of course, the AID or its fragment or mutant can be at the N-terminus of the amino acid sequence of the fusion protein, and the Cas enzyme is at the C-terminus. In certain embodiments, provided herein are fusion proteins substantially formed by a Cas enzyme and AID or a fragment or mutant thereof. It should be understood that the fusion protein "substantially formed by . . . " or similar references herein does not indicate that the fusion protein only contains Cas enzyme and AID or its fragment or mutant thereof. The phrase should be understood that the fusion protein can only contain Cas enzyme and AID or its fragment or mutant thereof, or the fusion protein can further contain other parts that do not affect the targeting effect of the Cas enzyme and the function to mutate target sequence(s) by AID or its fragment or mutant thereof in the fusion protein. Said other parts include but are not limited to various linker sequences, nuclear localization sequences, UGI sequences, and amino acid sequences introduced into the fusion protein due to gene cloning process and/or to construct the fusion protein, to promote expression of the recombinant proteins, to obtain the recombinant proteins automatically secreted from the host cells, or to facilitate the detection and/or purification of the recombinant proteins, as described below.

Cas enzymes can be fused to AID or fragments or mutants thereof via linkers. The linker may be a peptide of 3 to 25 residues, for example, a peptide of 3 to 15, 5 to 15, 10 to 20 residues. Suitable examples of the peptide linkers are well known in the art. Generally, a linker contains one or more motifs that repeat in sequence, which usually contain Gly and/or Ser. For example, the motif may be SGGS (SEQ ID NO: 40), GSSGS (SEQ ID NO: 41), GGGS (SEQ ID NO: 42), GGGGS (SEQ ID NO: 43), SSSSG (SEQ ID NO: 44), GSGSA (SEQ ID NO: 45) and GGSGG (SEQ ID NO: 46). Preferably, the motifs are adjacent to each other in the linker sequence, with no amino acid residue inserted between the repeated motifs. The linker sequence may comprise or consist of 1, 2, 3, 4 or 5 repeated motifs. In certain embodiments, the linker sequence is a polyglycine linker sequence. The number of glycine in the linker sequence is not particularly limited, but is usually 2-20, such as 2-15, 2-10, 2-8. In addition to glycine and serine, the linker can also contain other known amino acid residues, such as alanine (A), leucine (L), threonine (T), glutamic acid (E), phenylalanine (F), arginine (R), glutamine (Q), etc. In certain embodiments, the linker sequence is XTEN, and its amino acid sequence is shown as amino acid residues 183-198 of SEQ ID NO:29. Other exemplary linker sequences can be the linker sequences described in CN201710451424.3, such as SEQ ID NO: 21-31 described therein.

It should be understood that it is often necessary to add appropriate restriction site(s) during the gene cloning process, which will inevitably introduce one or more irrelevant residues at the end(s) of the expressed amino acid sequence(s), while not affect the activity of the obtained sequence. In order to construct the fusion protein, promote the expression of the recombinant protein, obtain the recombinant proteins automatically secreted from the host cells, or facilitate the purification of the recombinant proteins, it is often necessary to add amino acid(s) to the N-terminus, C-terminus, or within other suitable regions of the recombinant protein, and the added amino acid(s) include but are not limited to suitable linker peptides, signal peptides, leader peptides, terminally extended amino acid(s), etc. Therefore, the N-terminus or C-terminus of the fusion protein herein may futher contains one or more polypeptide fragments as protein labels. Any suitable label can be used for this disclosure. For example, the labels may be FLAG, HA, HA1, c-Myc, Poly-His, Poly-Arg, Strep-TagII, AU1, EE, T7, 4A6, ε, B, gE, and Ty1. These labels can be used to purify proteins.

The fusion protein herein may also contain a nuclear localization sequence (NLS). Nucleus localization sequences known in the art derived from various sources and with various amino acid compositions can be used. Such nuclear localization sequences include, but are not limited to: NLS from SV40 virus large T antigen; NLS from nucleoplasmic proteins, for example, nucleoplasmic protein bipartite NLS; NLS from c-myc; NLS from hRNPA1M9; sequences from importin beta binding domain (IBB domain) of importin-α; sequences from myoma T protein; sequences from mouse c-ablIV; sequences from influenza virus NS1; sequences from hepatitis virus 6 antigen; sequences from mouse Mx1 protein; sequences from human poly(ADP-ribose) polymerase; and sequences from steroid hormone receptor (human) glucocorticoid; etc. The amino acid sequences of these NLS sequences can be found in CN201710451424.3 as SEQ ID NO: 33-47. In certain specific embodiments, the sequence shown by amino acid residues 26-33 of SEQ ID NO: 25 is used herein as NLS. The NLS can be located at the N-terminus, C-terminus of the fusion protein; it can also be located within the sequence of the fusion protein, such as located at the N-terminus and/or C-terminus of the Cas9 enzyme in the fusion protein, or located at the N-terminal and/or C-terminal of the AID or its fragment or mutant in the fusion protein.

The accumulation of the fusion protein disclosed herein in the nucleus can be detected by any suitable technique. For example, detection labels can be fused to the Cas enzyme so that the location of the fusion proteins within cells can be visualized when combined with methods of detecting nucleus location (e.g., a dye specific to the nucleus, such as 4',6-Diamidino-2-Phenylindole (DAPI)). In some embodiments, 3*flag is used as a label herein, and the peptide sequence may be amino acid residues 1 to 23 of SEQ ID NO:25. It should be understood that, generally, if a label sequence is used, the label sequence is at the N-terminus of the fusion protein. The label sequence can be directly connected to NLS, or may be connected via an appropriate linker sequence. The NLS sequence may be directly connected to the Cas enzyme or AID or its fragment or mutant, or it may be connected to the Cas enzyme or AID or its fragment or mutant through an appropriate linker sequence.

Therefore, in certain embodiments, the fusion protein herein consists of a Cas enzyme and a AID or its fragment or mutant. In other embodiments, the fusion protein herein is formed by connection of a Cas enzyme to a AID or its fragment or mutant via a linker. In certain embodiments, the fusion protein herein consists of a NLS, a Cas enzyme, a AID or its fragment or mutant, and optionally a linker sequence between the Cas enzyme and the AID or its fragment or mutant. In certain embodiments, in addition to the NLS, Cas enzyme and AID or a fragment or mutate thereof, the fusion protein herein may also contain a phage protein, such as UGI as an UNG inhibitor. The amino acid sequence of an exemplary UGI may be amino acid residues 1576-1659 of SEQ ID NO: 23 of the present disclosure. Therefore, in certain embodiments, the fusion protein herein contains the Cas9 enzyme described herein, the AID or a fragment or mutant thereof, UGI and NLS described herein, or consists of these parts, optional linker(s) between them and optional amino acid sequence(s) for detection, isolation or purification. The UGI sequence may be located at the N-terminus, C-terminus of the fusion protein, or within the fusion protein, for example, located between the NLS sequence and the Cas enzyme or between the Cas enzyme and the AID or a fragment or mutant thereof. In certain embodiments, the fusion protein herein contains or consists of, from the N-terminus to the C-terminus, AID or a fragment or mutant thereof, Cas enzyme, UGI and NLS, or contains or consists of, from the N-terminus to the C-terminus, Cas enzyme, AID or a fragment or mutant thereof, UGI and NLS; they can be connected by linker(s).

In certain embodiments, the fusion proteins disclosed in CN 201710451424.3 are used herein. More specifically, the amino acid sequence of the used fusion protein disclosed in this disclosure is SEQ ID NO: 25, 27, 29, 31, 33, 48, or 50, or amino acids 26-1654 of SEQ ID NO: 25, or amino acids 26-1638 of SEQ ID NO: 27, or amino acids 26-1629 of SEQ ID NO: 31, or amino acids 26-1638 of SEQ ID NO: 33, or amino acids 26-1629 of SEQ ID NO: 48. In certain embodiments, the fusion protein herein is shown by SEQ ID NO: 23 of the present disclosure.

An expression vector/plasmid expressing the above fusion protein and a vector/plasmid expressing the desired sgRNA can be constructed and transferred into cells of interest to regulate their RNA splicing by inducing mutations at the splice site(s) of the gene of interest.

The "expression vector" may be various bacterial plasmids, bacteriophages, yeast plasmids, plant cell viruses, mammalian cell viruses such as adenovirus, retrovirus, or other vectors well known in the art. Any plasmid or vector can be used, provided that it can replicate and be stable in the host. An important characteristic of an expression vector is that it usually contains an origin of replication, a promoter, a marker gene and a translation control element. The expression vector may also include a ribosome binding site for translation initiation and a transcription terminator. The polynucleotide sequences described herein are operably linked to appropriate promoters in the expression vectors, so that mRNA synthesis is directed by the promoters. Representative examples of these promoters are: the lac or trp promoter of *E. coli*; the PL promoter of phage λ; eukaryotic promoters including the CMV immediate early promoter, the HSV thymidine kinase promoter, the early and late SV40 promoters, LTRs of retroviruses, and other known promoters that can control gene expression in prokaryotic or eukaryotic cells or their viruses. Marker genes can provide phenotypic traits for selection of transformed host cells, including but not limited to dihydrofolate reductase, neomycin resistance, and green fluorescent protein (GFP) for eukaryotic cell, or tetracycline or ampicillin resistance for *E. coli*. When the polynucleotides described herein are expressed in higher eukaryotic cells, transcription will be enhanced if an enhancer sequence is inserted into the vector. Enhancers are cis-acting factors of DNA, usually are about 10 bp to 300 bp, which act on the promoter to enhance gene transcription.

Those skilled in the art know how to select appropriate vectors, promoters, enhancers and host cells. Methods well known to those skilled in the art can be used to construct expression vectors containing the polynucleotide sequences described herein and appropriate transcription/translation control signals. These methods include in vitro recombinant DNA technology, DNA synthesis technology, in vivo recombinant technology and so on.

The fusion protein herein, its coding sequence or expression vector, and/or the sgRNA, its coding sequence or expression vector may be provided in the form of a composition. For example, the composition may contain the fusion protein herein and the sgRNA or the vector expressing the sgRNA, or may contain the vector expressing the fusion protein herein and the sgRNA or the vector expressing the sgRNA. In the composition, the fusion protein or its expression vector, or sgRNA or its expression vector may be provided as a mixture, or may be packaged separately. The composition may be in the form of a solution or a lyophilized form. Preferably, the fusion protein in the composition is a fusion protein of the AID or a fragment or mutant thereof described herein and the Cas enzyme described herein.

The composition may be provided in a kit. Accordingly, provided herein are kits containing the compositions described herein. Alternatively, provided herein is a kit containing the fusion protein herein and the sgRNA or the vector expressing the sgRNA, or containing the vector expressing the fusion protein herein and the sgRNA or the vector expressing the sgRNA. In the kit, the fusion protein or its expression vector, or sgRNA or its expression vector may be packaged separately, or may be provided as a mixture. The kit may further include, for example, reagents for transferring into cells the fusion protein or its expression vector and/or sgRNA or its expression vector, and instructions for the transfer. Alternatively, the kit may also include instructions for implementing the various methods and uses described herein using the ingredients contained in the kit. The kit also includes other reagents, such as reagents for PCR.

The fusion protein herein, its coding sequence or expression vector, and/or the sgRNA or its expression vector can be used to induce base mutations at a splice site of the gene of interest to regulate its RNA splicing. Therefore, provided herein is a method for inducing base mutation in a splice site of a gene of interest in a cell of interest, wherein the method comprises the step of expressing the fusion protein described herein in the cell, the method also comprises the step of expressing sgRNAs or gDNAs based on the expressed fusion protein. For example, in certain embodiments, the fusion protein described herein of the AID or a fragment or mutant thereof and the Cas enzyme, together with its recognized sgRNA, are expressed in cells. In certain embodiments, the fusion protein of a cytosine deaminase, or a fragment or mutant thereof retaining enzyme activity, and a TALEN protein that specifically recognizes a target sequence is expressed in cells. In certain embodiments, the fusion protein of a cytosine deaminase, or a fragment or mutant thereof retaining enzyme activity, and a zinc finger protein that specifically recognizes a target sequence is expressed in cells. In certain embodiments, the fusion protein of a cytosine deaminase or a fragment or mutant thereof retaining enzyme activity and a Cpf enzyme with helicase activity and partial or no nuclease activity, together with the sgRNA recognized by the Cpf enzyme, are expressed in cells. In other embodiments, the fusion protein of a cytosine deaminase or a fragment or mutant thereof retaining enzyme activity and an Ago protein, together with the gDNA recognized by the Ago protein, are expressed in cells.

In this disclosure, cells of interest especially also include those in which a splice site of a gene of interest needs to be mutated to regulate its RNA splicing. Such cells include prokaryotic cells and eukaryotic cells, such as plant cells, animal cells, microbial cells, and the like. Especially preferred are animal cells, such as mammalian cells, rodent cells, including cells of humans, horses, cattles, sheeps, mice, rabbits, and the like. Microbial cells include cells from various microbial species that are well known in the art, especially cells from microbial species valuable in medical research and production (e.g., production of fuel such as ethanol, protein, and oil such as DHA). The cells may also be cells from various organs, such as cells from human liver, kidney, or skin, etc, or may be blood cells. The cells may also be various mature cell lines that are commercially available, such as 293 cells, COS cells. In some embodiments, the cells are those from healthy individuals; in other embodiments, the cells are those from diseased tissues of diseased individuals, such as cells from inflammatory tissues, or tumor cells. In certain embodiments, the cells of interest are induced pluripotent stem cells. Cells can be those genetically engineered to have a specific function (e.g., to produce a protein of interest) or to generate a phenotype of interest. It should be understood that cells of interest include somatic cells and germ cells. In certain embodiments, the cells are specific cells in animals or humans.

The genes of interest may be any nucleic acid sequences of interest, especially various genes or nucleic acid sequences related to diseases, or related to the production of various proteins of interest, or related to biological functions of interest. Such genes or nucleic acid sequences of interest include, but are not limited to, nucleic acid sequences encoding various functional proteins. Herein, a functional protein refers to a protein capable of achieving the physiological function of an organism, including a catalytic protein, a transport protein, an immune protein, and a regulatory protein. In certain specific embodiments, the functional proteins include, but are not limited to: proteins involved in the occurrence, development and metastasis of diseases, proteins involved in cell differentiation, proliferation and apoptosis, proteins involved in metabolism, development-related proteins, and various medicinal targets, etc. For example, functional proteins may be antibodies, enzymes, lipoproteins, hormone-like proteins, transport and storage proteins, kinetic proteins, receptor proteins, membrane proteins, and the like.

As illustrative examples, genes of interest include but are not limited to RPS24, CD45, DMD, PKM, BAP1, TP53, STAT3, GANAB, ThyN1, OS9, survival motor neuron 2 (SMN2), 0-hemoglobin gene, lamin A/C gene (LMNA), murine double minute 4 (MDM4), B-cell lymphoma 2 (Bc12), and low-density lipoprotein receptor-related protein 8 (LRP8), etc.

In certain embodiments, the methods described herein include transferring the fusion protein or its expression vector and its recognized sgRNA or expression vector thereof or gDNA or expression vector thereof into the cell. In the case where the cell constitutively expresses the fusion protein described herein, the corresponding sgRNA or expression vector thereof or its recognized gDNA or expression vector thereof can be transferred into the cell alone. In the case where the cell inducibly expresses the fusion protein described herein, after being transfered with the sgRNA or gDNA, the cell can also be incubated with an inducing agent, or the cell can be subjected to corresponding induction means (such as lighting). Preferably, the method herein is implemented using the fusion protein of the AID or a fragment or mutant thereof described herein and the Cas enzyme described herein, together with its recognized sgRNA.

Conventional transfection methods can be used to transfer into cells the fusion protein or its expression vector and/or its recognized sgRNA or expression vector thereof or gDNA or expression vector thereof. For example, when the cell of interest is a prokaryotic organism such as *E. coli*, competent cells that can absorb DNAs can be harvested after the exponential growth phase and treated with the $CaCl_2$) method, which is well known in the art. Another method is to use $MgCl_2$. If necessary, transformation can also be carried out by electroporation. When the host is a eukaryote, the following DNA transfection methods can be used: the calcium phosphate co-precipitation method, conventional mechanical methods such as microinjection, electroporation, liposome packaging, etc. For example, during transfection, the plasmid DNA-liposome complex is prepared and co-transfected into the cell together with the corresponding sgRNA or gDNA. Commercially available transfection kits or reagents can be used to transfer the vectors or plasmids described herein into cells of interest, such reagents include but are not limited to Lipofectamine® 2000 reagents. After transforming the cells, the obtained transformants can be cultured by conventional methods to express the fusion proteins described herein. According to the used cells, the culture medium can be selected from various conventional culture media.

Generally, for different cells, expression vectors expressing the fusion protein and sgRNA or gDNA of the present disclosure can be designed using known techniques, so that these expression vectors are suitable for expression in the cells. For example, a promoter and other related regulatory sequences that facilitate starting expression in the cell can be provided in the expression vector. These can be selected and implemented by technicians according to actual practice.

For the sgRNA used in this disclosure, the site that suitable as a PAM can be found near the splice site of interest of the gene of interest, and the Cas enzyme that recognizes the PAM can be selected based on the PAM, and then the fusion protein herein containing the Cas enzyme together with its corresponding sgRNA can be designed and prepared as described herein. Therefore, the target recognition region of the sgRNA used herein usually contains the complementary sequence of the splice site(s) of the intron of interest of the gene of interest.

The splice site described herein has a well-known meaning in the art, including 5' splice site and 3' splice site. Herein, both the 5' splice site and the 3'splice site are relative to an intron. Generally, the site that can serve as a PAM is selected near the splice site of the exon/intron of interest of the gene of interest. For example, the exon or intron of interest of the gene of interest may be exon 5 of RPS, exon 5 of CD45, exon 8 or 9 of TP53 gene, exon 9 or 10 of PKM, intron 2 of BAP1 and intron 8 of TP53, etc. Alternatively, in certain embodiments, the site that can serve as a PAM is selected near the polypyrimidine chain present within the intron upstream of the 3' splice site of the gene of interest. Therefore, the target binding region of such sgRNA contains the sequence of the polypyrimidine region of the intron of interest of the gene of interest.

The method herein may be a method in vitro or a method in vivo; in addition, the method herein includes a method for therapeutic purposes and a method for non-therapeutic purposes. When implemented in vivo, the fusion protein herein or its expression vector and its recognized sgRNA or expression vector thereof or gDNA or expression vector thereof can be transferred into the body of the subject, such as corresponding tissue cells, by methods well known in the art. It should be understood that when implemented in vivo, the subjects may be humans or various non-human animals, including various non-human model organisms commonly used in the art. Experiments in vivo should meet ethical requirements.

The method described herein for inducing base mutations at the splice site of a gene of interest in a cell of interest is a general RNA splicing regulation method that can be used for gene therapy. Accordingly, provided herein is a method for gene therapy, comprising administering to a subject in need a therapeutically effective amount of a vector expressing the fusion protein described herein and a vector expressing the corresponding sgRNA or gDNA. The therapeutically effective amount can be determined according to the age, sex, nature and severity of the disease, etc. Generally, administration of a therapeutically effective amount of the vector should be sufficient to alleviate the symptoms of the disease or cure the disease. The gene therapy can be used for the treatment of diseases caused by genetic mutations, and can also be used for the treatment of diseases in which symptoms of the diseases can be relieved or the diseases can be cured by regulating different splicing isoforms. For example, diseases caused by genetic mutations include but are not limited to: Duchenne myasthenia caused by mutations in the DMD gene, survival motor neuron (SMN), thalassemia caused by 647G>A mutation of β hemoglobin intron 2 (IVS2), familial hypercholesterolemia and premature aging caused by LMNA mutation, etc. Diseases in which symptoms of the diseases can be relieved or the diseases can be cured by regulating ratio of different splicing isoforms include tumors, the splicing isoforms including but not limited to conversion of Stat3α to Stat3β, conversion of PKM2 to PKM1, MDM4 exon 6 skipping, selection of Bc12 alternative splice sites, LRP8 exon 8 skipping.

In certain embodiments, provided herein is a method for tumor therapy, comprising administering to a subject in need a therapeutically effective amount of a vector expressing the fusion protein described in any embodiment herein and a vector expressing corresponding sgRNA. In certain embodiments, the target binding region of the sgRNA comprises the complementary sequence of the 3' splice site of Stat3 intron 22. In certain embodiments, the target binding region of sgRNA suitable for the method is shown as SEQ ID NO: 3. Alternatively, the target binding region of the sgRNA comprises the complementary sequence of the 5' or 3' splice site of PKM intron 10. In certain embodiments, the target binding region of sgRNA suitable for the method is shown as SEQ ID NO: 15 or 16.

In certain embodiments, provided herein is a method of treating Duchenne myasthenia due to a DMD gene mutation, the method comprising the step of administering to a subject in need a therapeutically effective amount of a vector expressing the fusion protein described herein and a vector expressing corresponding sgRNA, wherein the target binding region of the sgRNA comprises the complementary sequence of the 5' splice site of DMD exon 50. In certain embodiments, the target binding region of sgRNA suitable for the method is shown as SEQ ID NO: 17 or 51. In certain embodiments, the amino acid sequence of the fusion protein suitable for the method is shown as SEQ ID NO: 23 or 50.

The methods for gene therapy described herein can be implemented by means well known in the art. Generally, the routes of administration for gene therapy include routes ex vivo and routes in vivo. For example, suitable backbone vectors (such as adeno-associated virus vectors) can be used to construct expression vectors expressing the fusion protein described herein and vectors expressing the sgRNA or gDNA, which can be administered to the patient in a general route, such as injection. Alternatively, in the case of blood diseases, blood cells having a gene variation of the subject may be obtained, treated in vitro using the method described herein, proliferated in vitro after the variation is eliminated, and then reinfused into the subject. In addition, the methods described herein can also be used to modify pluripotent stem cells of the subject, which are reinfused into the subject to achieve therapeutic purposes.

In yet another aspect of the present disclosure, provided herein is use of the fusion protein, its coding sequence and/or expression vector, and/or sgRNA and/or its expression vector according to any of the embodiments herein in the preparation of a reagent or a kit for regulating RNA splicing, in the preparation of a reagent for gene therapy, or in the preparation of a medicament for the treatment of diseases caused by genetic mutations or tumors that benefit from changes in the proportion of different splicing isoforms of functional proteins. This disclosure is also directed to the fusion protein, its coding sequence and/or expression vector, and the sgRNA and/or its expression vector, according to any of the embodiments described herein, for regulating RNA splicing, gene therapy (especially for the treatment of diseases caused by genetic mutations or tumors benefiting from changes in the proportion of different splicing isoforms of functional proteins).

The methods described herein can effectively induce exon skipping (e.g., RPS24 exon 5, CD45 exon 5, DMD gene exon 50, 23, 51, etc.), regulate the selection of mutually exclusive exons (PKM1/PKM2, etc.), induce intron retention/inclusion (BAP1 and TP53, etc.) and induce the use of alternative splice sites (STAT3α/β, etc.), and the like. At the same time, by mutating the C upstream of the 3' splice site to T, the inclusion ratio of selective exons can be promoted (RPS24 exon 5, GANAB exon 5, ThyN1 exon 6, OS9 exon 13 and SMN2 exon 7). In addition, this disclosure also proves that this method can effectively correct the genetic splicing defects caused by human genetic mutations. Therefore, the method disclosed herein is a general RNA splicing regulation method, which can be used for treatment of diseases, especially for gene therapy of the following diseases: Duchenne myasthenia caused by mutations in the DMD gene, SMN, thalassemia caused by 647G>A mutation of β hemoglobin IVS2, familial hypercholesterolemia and premature aging caused by LMNA mutation. At the same time, the method described herein can also achieve the treatment of tumors and other diseases by regulating the ratio of different splicing isoforms, including but not limited to inducing conversion of Stat3α to Stat3β, conversion of PKM2 to PKM1, MDM4 exon 6 skipping, selection of Bc12 alternative splice sites, LRP8 exon 8 skipping, etc.

The present disclosure will be illustrated by way of specific examples below. It should be understood that these examples are merely exemplary and do not limit the scope of the present disclosure. The experimental methods without specifying the specific conditions in the following examples generally used the conventional conditions, such as those described in Sambrook & Russell, Molecular Cloning: A Laboratory Manual (3rd ed.) or followed the manufacturer's recommendation. Unless defined otherwise, technical and scientific terms used herein have the same meaning as commonly understood by one of ordinary skill in the art to which this disclosure is related. In addition, any methods and materials similar or equivalent to those described herein can be applied to the present disclosure. The preferable implementation methods and materials described herein are for illustration purposes only.

I. Materials and Methods (1) Construction of Plasmids Expressing AIDX-Cas9 or Cas9-AIDX Fusion Protein With reference to the method disclosed in the examples of CN 201710451424.3 (the entire contents of which are incorporated herein by reference), a plasmid expressing AIDX-Cas9 or Cas9-AIDX fusion protein used herein was constructed.

In the following experiments, the AIDX-nCas9-UGI fusion protein was used, and its expression plasmid, namely MO91-AIDX-XTEN-nCas9-UGI, was constructed according to the methods of Examples 1-3 and 14 of CN 201710451424.3, which expressed the fusion protein of SEQ ID NO: 23, wherein, residues 1-182 is the amino acid sequence of AIDX, residues 183-198 is the amino acid sequence of linker XTEN, residues 199-1566 is the amino acid sequence of nCas9, and residues 1567-1570 and 1654-1657 are linker sequences, residues 1571-1653 is the amino acid sequence of UGI, and residues 1658-1664 is the amino acid sequence of SV40 NLS. The coding sequence of the fusion protein is shown as SEQ ID NO: 22.

(2) Preparation of gRNA

1. Searching for 20 bp target sequence. If the starting base of the 20 bp target sequence is not G, a G should be added to its 5' end to enable efficiently transcription by the RNA polymerase III U6 promoter. It should be n oted that the target sequence cannot contain XhoI or NheI recognition site.
2. The sgRNA was cloned into pLX (Addgene) to obtain pLX sgRNA. The following 4 primers were required, wherein R1 and F2 were sgRNA specific:

(SEQ ID NO: 18)
F1: AAA*CTCGAG*TGTACAAAAAAGCAGGCTTTAAAG (SEQ ID NO: 19)
R1: rc($GN_{19}$)GGTGTTTCGTCCTTTCC (SEQ ID NO: 20)
F2: $GN_{19}$GTTTTAGAGCTAGAAATAGCAA (SEQ ID NO: 21)
R2: AAA*GCTAGC*TAATGCCAACTTTGTACAAGAAAGCTG wherein, $GN_{19}$=new target binding sequence, rc($GN_{19}$)=reverse complementary sequence of the new target binding sequence.

3. F1+R1 and F2+R2 were used to amplify pLX sgRNA respectively;
4. The two amplified products were purified by gel purification, combined and used for the third PCR with F1+R2;
5. NheI and XhoI were used to digest the products obtained from the PCR in Step 4; and
6. SgRNA expression vectors were prepared by ligation and transformation.

(3) Cell Transfection

293T Cells were grown to 70-90% confluence before transfection. For transfection, plasmid DNA-liposome complexes were prepared by diluting four-folds amount of Lipofectamine® 2000 reagent in Opti-MEM® medium, and separately diluting the plasmid expressing the fusion protein described herein and the plasmid for the corresponding sgRNA in Opti-MEM® medium, then adding the diluted plasmids to the diluted Lipofectamine® 2000 reagent (1:1) and incubating for 30 minutes. The plasmid DNA-liposome complex was then transfected into 293T cells. As a control, only the plasmid DNA-liposome complex was transfected into reporter cells obtained according to Example 4 of CN201710451424.3, 2 ug/ml puromycin and 20 ug/ml blasticidin were added, and cells were screened for 3 days; on day 7 after transfection, gene expression, splicing and mutation were analyzed by high-throughput sequencing, respectively.

(4) Quantitative PCR and High-Throughput Sequencing, Etc.

Unless defined otherwise, biological methods such as quantitative PCR and high-throughput sequencing in this disclosure were implemented using the methods and reagents commonly used in the art.

II. Result

1. Mutation of G to a at the Splice Site(s) LED to Exon Skipping.

RPS24 is a constituent protein of ribosomes, and its mutation will cause congenital aplastic anemia. Exon 5 of RPS24 can be alternatively spliced to produce two isoforms with different 3' untranslated regions (UTRs), in which liver cancer cells tend to express the isoform containing exon 5. However, its physiological function is not clear.

In this experiment, TAM technology was used to design the sgRNA (RPS24-E5-5'SS, the sequence of its target binding region is shown in SEQ ID NO: 9), and the G of the 5' splice site or 3' splice site of RPS24 exon 5 was mutated to A, regulating alternative splicing of exon 5. 293T cells were transfected as described above, and gene expression, splicing and mutation were analyzed by high-throughput sequencing on the 7th day after transfection.

Figure 3:
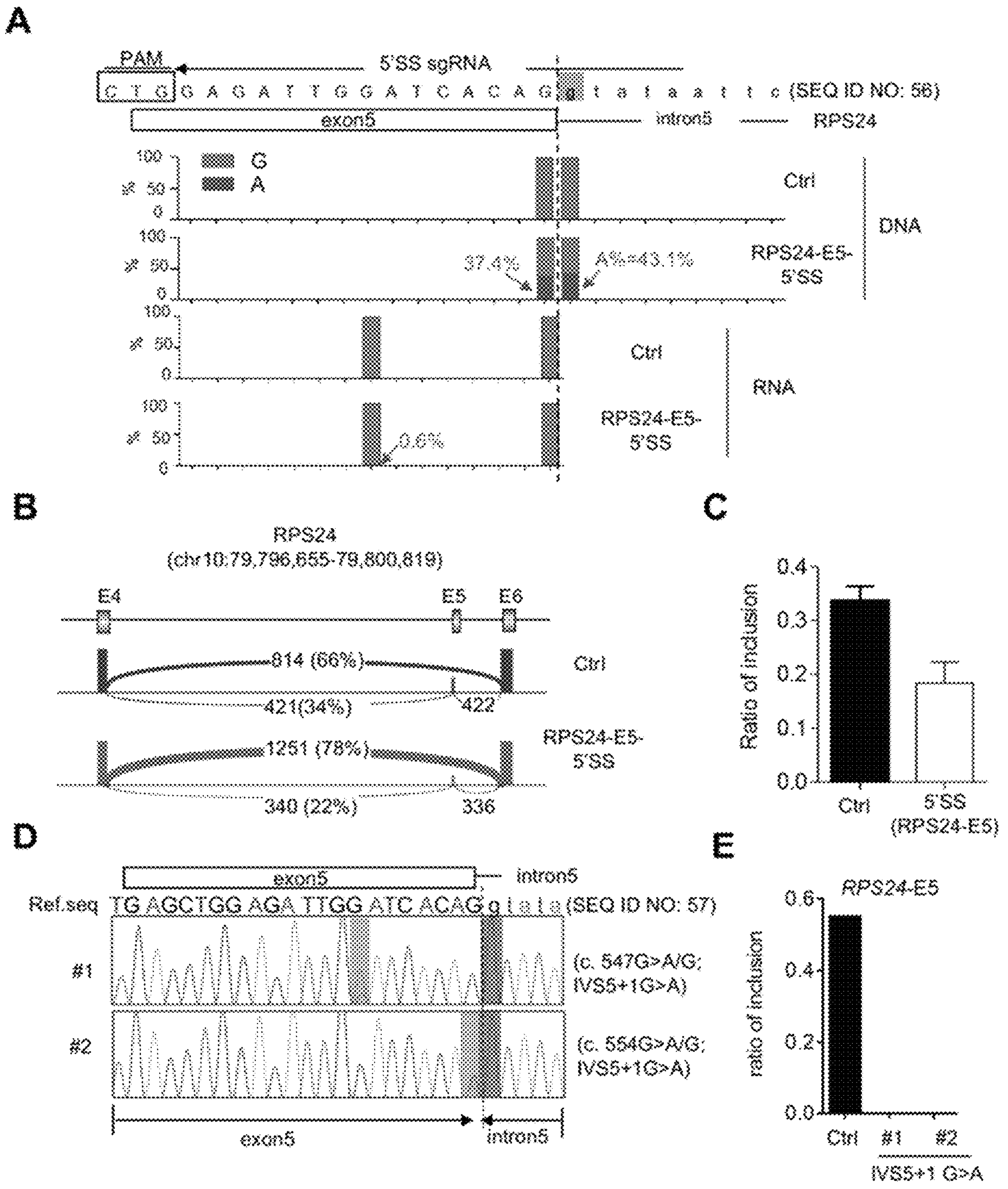
FIG. 3: TAM promoted skipping of ribosomal protein S24 (RPS24) exon 5 by converting the invariant guanine at the 5' SS to adenine. (A) The conversion of adenine at the 5' splice site of RPS24 exon 5 to adenine by TAM. 293T cells were transfected with the expression plasmid(s) of nCas9-AIDx-UGI and control sgRNA (Ctrl) or the sgRNA targeting the 5' SS of RPS24 exon 5 (5') (E5-5'SS). Six days after transfection, sgRNA targeted regions were amplified from genomic DNA (top 2 panels) or cDNA (bottom 2 panels) and analyzed by high-throughput sequencing with over 8000× coverage. The base composition of nucleotides having detectable mutations (>0.1%) is depicted. The locations of the sgRNA and PAM sequences are shown on the top of the exon/intron junction sequence (SEQ ID NO: 56) from Refseq. Intron/exon junctions are depicted using dashed lines. The data are representative of two independent experiments. (B) TAM promoted the skipping of exon 5 in RPS24. As in A, the splicing junctions were amplified from cDNA and analyzed by high-throughput sequencing. The Figure shows the coverage and percentage of each splicing junction of the cells treated with control sgRNA (top panel) or E5-5'SS sgRNA (bottom panel). The count and percentage (in parentheses) of the junction readings are depicted on the top of each junction arc. For clarity, only the junction arcs representing more than 1% of the total transcripts are depicted. (C) The ratio of the RPS24 isoform to the included or skipped exon 5 was determined by isoform-specific real-time PCR. The data are the summary of three independent experiments. (D, E) The 5'SS G to A mutation caused a complete skipping of RPS24 exon 5 (SEQ ID NO: 57, the exon/intron junction sequence). Two single-cell clones were obtained from TAM-treated cells and analyzed by Sanger sequencing. The right of (D) shows the genotype of the cells. The expression of the isoform including exon 5 was determined by real-time PCR (E). The data are the summary of three independent experiments.

In 293T cells, the fusion protein targeted to the 5' splice site of RPS24 exon 5 by use of the UNG inhibitor UGI in the AIDX-nCas9-UGI fusion protein and the sgRNA. According to the results of the sequencing, the first base of intron 5 (IVS5+1) had more than 40% of G to A mutations, and the last base of exon 5 had 30% of G to A mutations, while there were other two sites on exon 5 having less than 10% of G to A mutations (FIG. 3, A). Sequencing of exon splice sites revealed that the inclusion ratio of exon 5 in the cells transfected with RPS24 sgRNA was decreased compared to the control group (FIG. 3, B); quantitative PCR results also provided the consistent conclusion (FIG. 3, C); no exon mutation was found in mature RNA (FIG. 3, A).

At the same time, two monoclonal cell lines with identical genotype were obtained, in which 5' splice sites were completely mutated to A, while a G to A mutation in the exon was also found (FIG. 3, D). In these two clones, the isoform containing RPS24 exon 5 was completely undetectable, indicating that the G to A mutation at the 5' splice site caused skipping of RPS24 exon 5 (FIG. 3, E).

The above results show that the TAM technique could effectively mutate G to A at the splice site(s), resulting in exon skipping (mutation at 5' splice site of RPS exon 5).

2. Mutation of G to a at the Splice Site(s) of CD45 Exon 5 LED to Exon Skipping.

To further verify whether the splice site(s) can be effectively destroyed and exon skipping can be regulated, three selective exons of the CD45 gene were selected as target genes. CD45 is a receptor tyrosine phosphatase, which can regulate the development and function of T lymphocytes and B lymphocytes by regulating the signaling of antigen receptors (such as TCR or BCR). The CD45 gene consists of approximately 33 exons, in which exons 4, 5, and 6 encoding the extracellular regions A, B, and C of the CD45 protein can be alternatively spliced. The expression pattern of the CD45 isoforms depends on the developmental stage of T cells and B cells. The longest CD45 isoform (B220) containing the three selective exons is expressed on the surface of B cells.

The sgRNAs (CD45-E5-5'SS and CD45-E5-3'SS, the sequences of their target binding region were SEQ ID NO: 1 and 2) for the Gs at 5' splice site and 3' splice site of exon 5 in CD45 gene were designed. The editing of exon 5 splice sites was performed in Raji cells, a germinal center B cell line expressing the unspliced CD45 isoform. 400 ng expression plasmid of AIDx-nCas9-UGI, 300 ng expression plasmid of sgRNA and 50 ng expression plasmid of UGI were electrotransfected into $1\times10^5$ Raji cells with Neon (Life Technologies) with 1,100V voltage and a pulse of 40 ms. 24 h after transfection, 2 g/ml puromycin was added to select transfected cells for 3 days.

Figure 2:
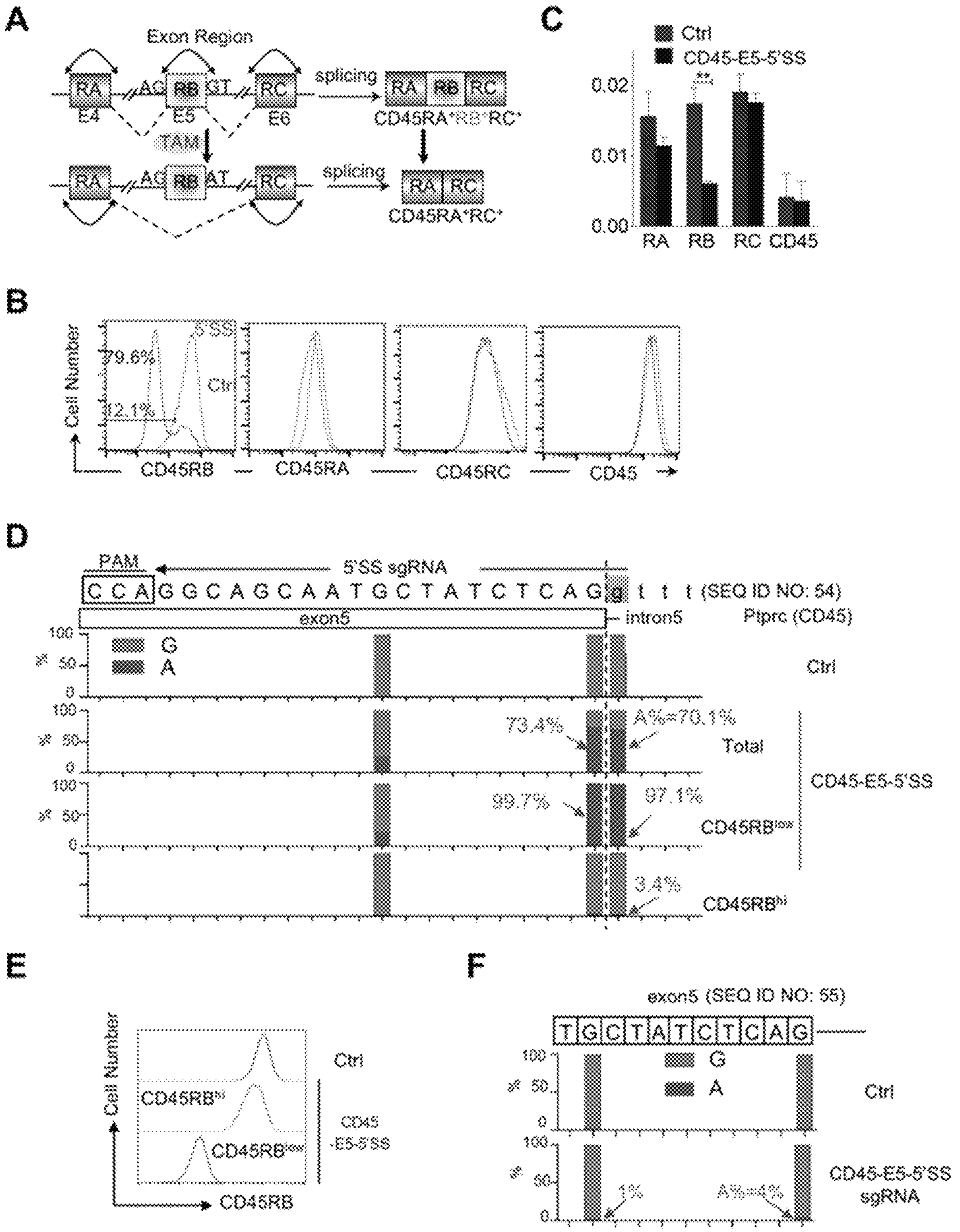
FIG. 2: TAM induced CD45RB exon skipping by converting the invariant guanine at the 5' splice site to adenine. (A) A schematic diagram of directing TAM to convert the invariant guanine at the 5' SS of CD45 RB exon to adenine, and induce exon skipping. (B, C) TAM caused CD45RB exon skipping. Raji cells were transfected with the expression plasmid(s) of AIDx-nCas9-UGI and targeting sgRNA (E5-5'SS) or control sgRNA against AAVS1 (Ctrl). Seven days after transfection, the expression of the targeted exon (CD45RB), its upstream exon (exon 4, CD45RA), downstream exon (Exon 6, CD45RC) and total CD45 was determined by flow cytometry using exon-specific antibodies (B), or by exon-specific real-time PCR (C). The data are representative (B) or summary (C) of two independent experiments. **, p<0.01 in Student's t test. (D) G>A mutation was enriched at the 5' site of CD45RB exon in CD45RB$^{low}$ cells. Intron-exon junctions were amplified from the cells shown in B and the sorted CD45RB$^{h}$ and CD45RB$^{low}$ cells from TAM-treated Raji cells. The amplicons were analyzed by high-throughput sequencing with over 8000× coverage. The base composition of each nucleotide having a detectable mutation (mutant reading/WT reading >0.1%) is depicted, and the percentage of G>A conversion of the target G is marked on the left. The locations of the sgRNA and PAM sequences are marked on the top of the intron-exon junction sequence (SEQ ID NO: 54). Intron/exon junctions are depicted using dashed lines. The data are representative of two independent experiments. (E) Flow cytometric analysis of CD45RB expression in control Raji cells or sorted CD45RB$^{hi}$ and CD45RB$^{low}$ cells from TAM-treated cells. (F) TAM induced CD45RB skipping and minimal changes in CD45 protein sequence. The exon-intron junctions (SEQ ID NO: 55) were amplified from cDNA and analyzed for base substitution by high-throughput sequencing. Note that the two mutations in the cDNA of TAM-treated cells are significantly reduced as compared with genomic DNA.

It was found that the two sgRNAs could induce G>A mutations at the splice sites in 53.6% and 73.4% of the DNAs, respectively (FIGS. 1 and 2). When the splice site(s) of exon 5 were destroyed, CD45RB expression was significantly down-regulated, and the expression of CD45RA and CD45RC did not change significantly, indicating that the splice sites were independent when inducing exon skipping, and mutations in either 5'SS or 3'SS could cause exon skipping.

4. Mutation of G to a at the Splice Site(s) of TP53 Exon 8 LED to Exon Skipping.

In this experiment, TAM technology was used to design sgRNA (TP53-E8-5'SS, the sequence of which is shown in SEQ ID NO: 7), and the G of the 3' splice site of TP53 exon 8 was mutated to A, regulating alternative splicing of exon 8 (FIG. 4). 293T cells were transfected as described above, and gene expression, splicing and mutation were analyzed by high-throughput sequencing on the 7th day after transfection.

Figure 4:
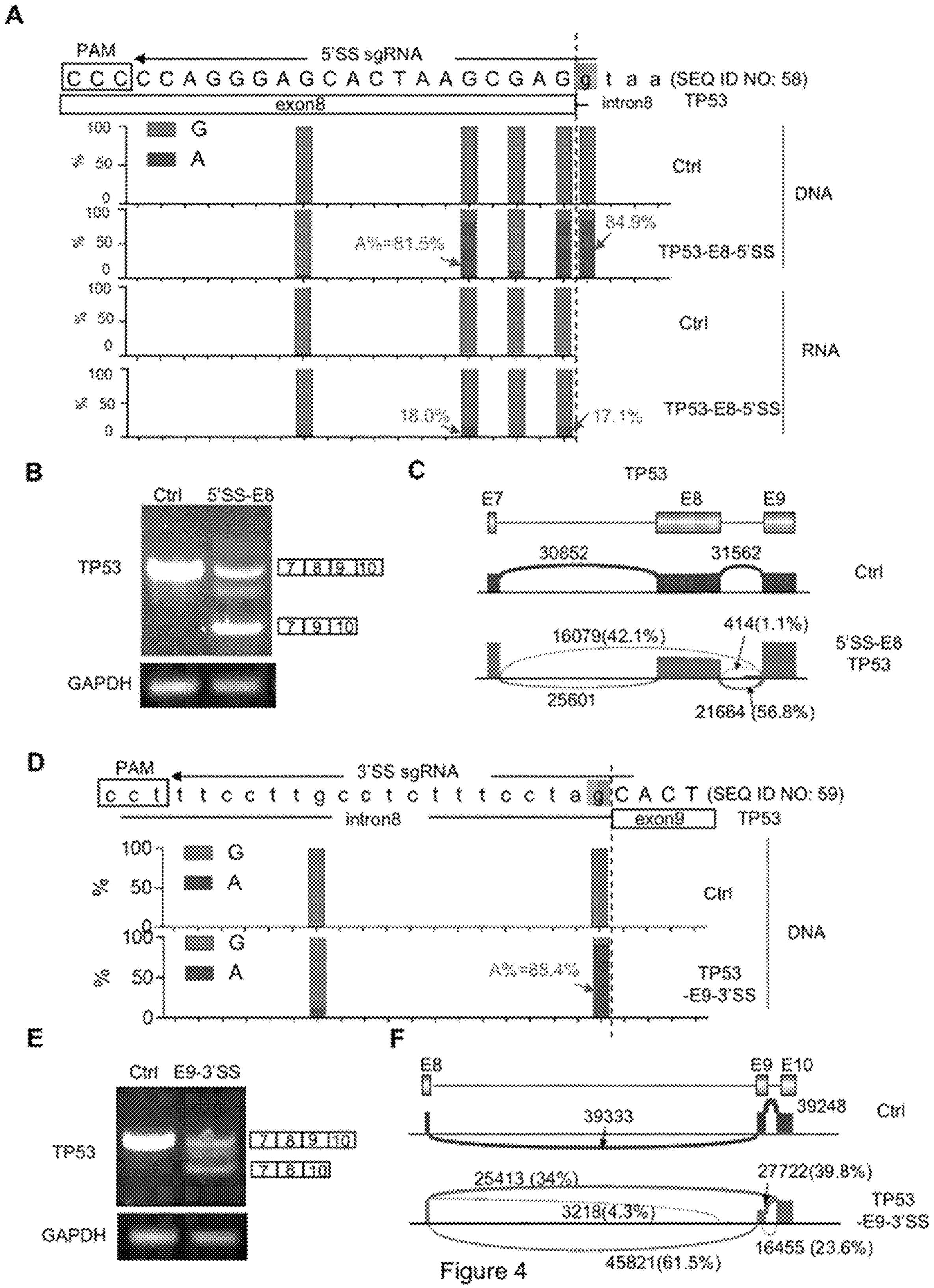
FIG. 4: TAM induced skipping of exon 8 or exon 9 in tumor protein p53 (TP53) by mutating guanine at their respective splice site. (A-C) TAM caused the skipping of exon 8 in TP53 by mutating its 5'SS. (A) As shown in FIG. 1, 293T cells were transfected with the expression plasmid (s) of nCas9-AIDx-UGI and control sgRNA against AAVS1 (Ctrl) or sgRNA targeting 5'SS of TP53 exon 8 (E8-5'SS). Six days after transfection, sgRNA targeted regions were amplified from genomic DNA (top 2 panels) or cDNA (bottom 2 panels) and analyzed by high-throughput sequencing. The base composition of nucleotides having detectable mutations (>0.1%) is depicted. The locations of the sgRNA and PAM sequences are shown on the top of the exon/intron junction sequence (SEQ ID NO: 58) from Refseq. Intron/exon junctions are depicted using dashed lines. The data are representative of two independent experiments. (B) Analysis of splicing of TP53 exon 8 by reverse transcription polymerase chain reaction (RT-PCR). (C) As in A, the splicing junctions were amplified from cDNA and analyzed by high-throughput sequencing. The Figure shows the coverage and percentage of each splicing junction of the cells treated with control sgRNA (top panel) or E8-5'SS sgRNA (bottom panel). For clarity, only the junction arcs representing more than 1% of the total transcripts are depicted. The count and percentage (in parentheses) of the junction readings are depicted on the top of each junction arc. Note that in TAM-treated cells, 42.1% of the total transcript skipped exon 8, while 1.1% activated the cryptic splice site within exon 8. (D-F) TAM caused the skipping of exon 9 in TP53 by mutating its 3'SS. (D) As shown in (A), 293T cells were transfected using TAM and sgRNA targeting 3'SS of TP53 exon 9. Seven days after transfection, intron-exon junctions (SEQ ID NO: 59) were amplified from genomic DNA and analyzed by high-throughput sequencing. (E) Analysis of TP53 splicing by RT-PCR. (F) As in D, the splicing junctions were amplified from cDNA and analyzed by high-throughput sequencing. Intersections that account for more than 1% of total transcripts are depicted. Note that 3'SS mutation caused exon skipping in 34% of the total transcripts and activation of the cryptic splice site in 23.6% of the mRNAs. TAM-treated cells also activated the neuronal exon within intron 8 (4.3% of the total transcripts). (A-F) Data represent two independent experiments.

According to the results of the sequencing, the first base of intron 8 (IVS8+1) had more than 80% of G to A mutations (FIG. 4, A). Sequencing of exon splice sites revealed that more than 40% of TP53s in sgRNA-transfected cells skipped exon 8; quantitative PCR results (FIG. 4, B, C) also provided the consistent conclusion; no exon mutation was found in mature RNA. The control group had no detectable skipping of exon 8.

5. Mutation of G to a at the Splice Site(s) of TP53 Exon 9 LED to Exon Skipping.

It was verified that skipping of exon 9 in TP53 gene can be achieved by the same method. Specifically, 293T cells were transfected using TAM and with the sgRNA targeting 3'SS of TP53 exon 9 (TP53-E9-3'SS, its target binding sequence is shown in SEQ ID NO: 8). Seven days after transfection, intron-exon junctions were amplified from genomic DNA and analyzed by high-throughput sequencing. TP53 splicing was analyzed by RT-PCR. The splicing junctions were amplified from cDNA and analyzed by high-throughput sequencing. 3'SS mutation caused exon skipping in 34% of the total transcripts and activation of the cryptic splice site in 23.6% of the mRNAs. TAM-treated cells also activated the neuronal exon within intron 8 (4.3% of the total transcripts) (FIG. 4, D-F).

Figure 5:
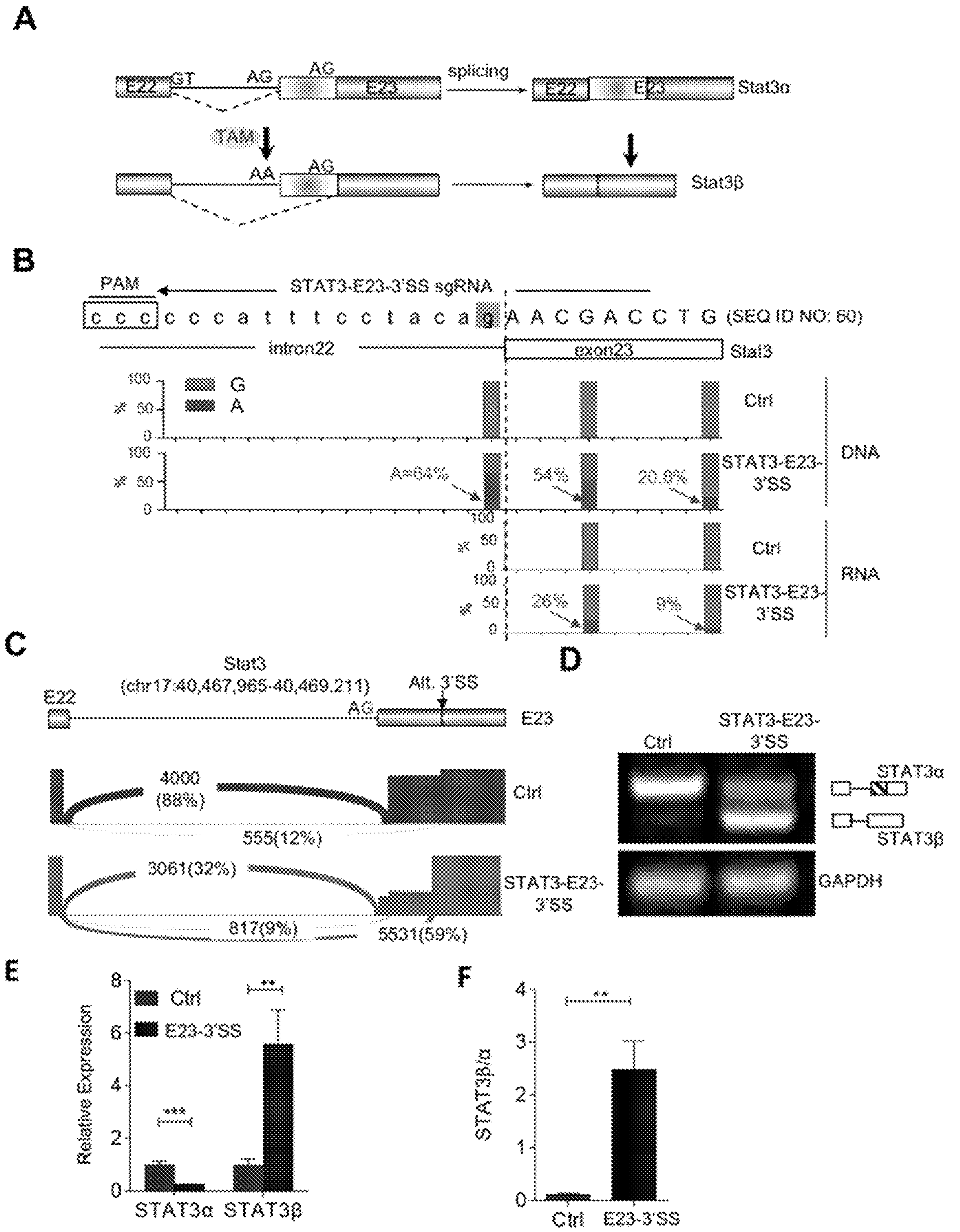
FIG. 5: TAM activated alternative splice sites and converted signal transducer and activator of transcription 3α (Stat3α) to signal transducer and activator of transcription 3β (Stat3β). (A) A schematic diagram of eliminating the typical 3'SS of signal transducer and activator of transcription 3 (Stat3) exon 23 (Stat3α) and promoting the use of downstream alternative 3'SS (Stat3β) by TAM. (B) Mutation of the invariant G at the typical 3'SS of Stat3 exon 23 by TAM.

6. Accurate Editing of Splice Sites can Change the Selection of Alternative Splice Sites In addition to exon skipping, the selection of alternative splice sites may occur during RNA splicing, and new protein isoforms with different physiological functions may be formed. For example, the selection of an alternative splice site on exon 23 of Stat3 will result in a truncated STAT3β isoform lacking the C-terminal transactivation domain. The full-length STAT3α can promote tumorigenesis, while STAT3β has dominant negative effect, inhibiting STAT3α function and promoting tumor cell apoptosis. Especially in breast cancer cells, inducing STAT3β expression can inhibit cell survival more effectively compared to knocking out STAT3 expression, indicating that inducing STAT3β expression can be used as a tumor therapy. Because there is only 50 bp between the conventional splice site and alternative splice site of STAT3, it is difficult to induce STAT3β expression using the conventional double sgRNA splicing method, while TAM technology can provide a more accurate gene editing method. In this experiment, with the sgRNA designed to destroy conventional splice sites, TAM eliminated the typical 3'SS of Stat3 exon 23 (Stat3α), and promoted the use of downstream alternative 3'SS (Stat3β), the schematic diagram of which is shown in FIG. 5(A). 293T cells were transfected with AIDx-nCas9-UGI and the sgRNA targeting Stat3 exon 23 (STAT3-E23-3'SS, its target binding region is shown in SEQ ID NO: 3) or the sgRNA targeting AAVS1 (Ctrl). Intron-exon junctions were amplified from DNA (top 2 panels) or cDNA (bottom 2 panels) and analyzed by high-throughput sequencing. TAM and sgRNA were expressed in 293T cells using the method described above, and more than 50% of the Gs at 3' splice site were mutated to As (FIG. 5, B). Results show that TAM enhanced the use of the distal 3'SS in Stat3 exon 23 (FIG. 5, C). Quantitative PCR and immunoblotting analysis revealed that STAT3β expression level was up-regulated and STAT3α expression level was down-regulated (FIG. 5, E-F). As expected, proliferation rate of the TAM-edited cells was more significantly suppressed compared to cells with STAT3 expression knocking out.

The above results show that, in the case of extremely close alternative splice sites, TAM technology can overcome the defects of conventional double sgRNA splicing methods, accurately destroy selective splice sites, and regulate the selection of alternative splice sites.

7. Mutually Exclusive Exon

Mutually exclusive exon is another major type of alternative splicing, in which mutually exclusive exons can be selectively included in different transcripts to produce proteins with different functions. Pyruvate kinase (PKM) is the rate-limiting enzyme of the glycolysis process. During splicing, exons 9 and 10 of PKM can be selectively included to produce two isoforms PKM1 and PKM2, wherein PKM1 containing exon 9 but not exon 10 is mainly expressed in adult tissues, while PKM2 containing exon 10 but not exon 9 is mainly expressed in embryonic stem cells and tumor cells. Because PKM2 is related to tumorigenesis, it is hoped that TAM technology can switch the PKM splicing mode of tumor cells from PKM2 to PKM1.

FIG. 6(A) shows a schematic diagram of TAM switching PKM2 to PKM1 in C2C12 cells. In the top panel, exon 10 of the PKM gene rather than exon 9 was spliced to produce PKM2, whose cDNA was recognized by the restriction enzyme PstI; in the bottom panel, TAM converted the GT dinucleotide to AT at the 5'SS of exon 10. Therefore, exon 9 instead of exon 10 was spliced to produce PKM1, whose cDNA was recognized by the restriction enzyme NcoI.

Figure 6:
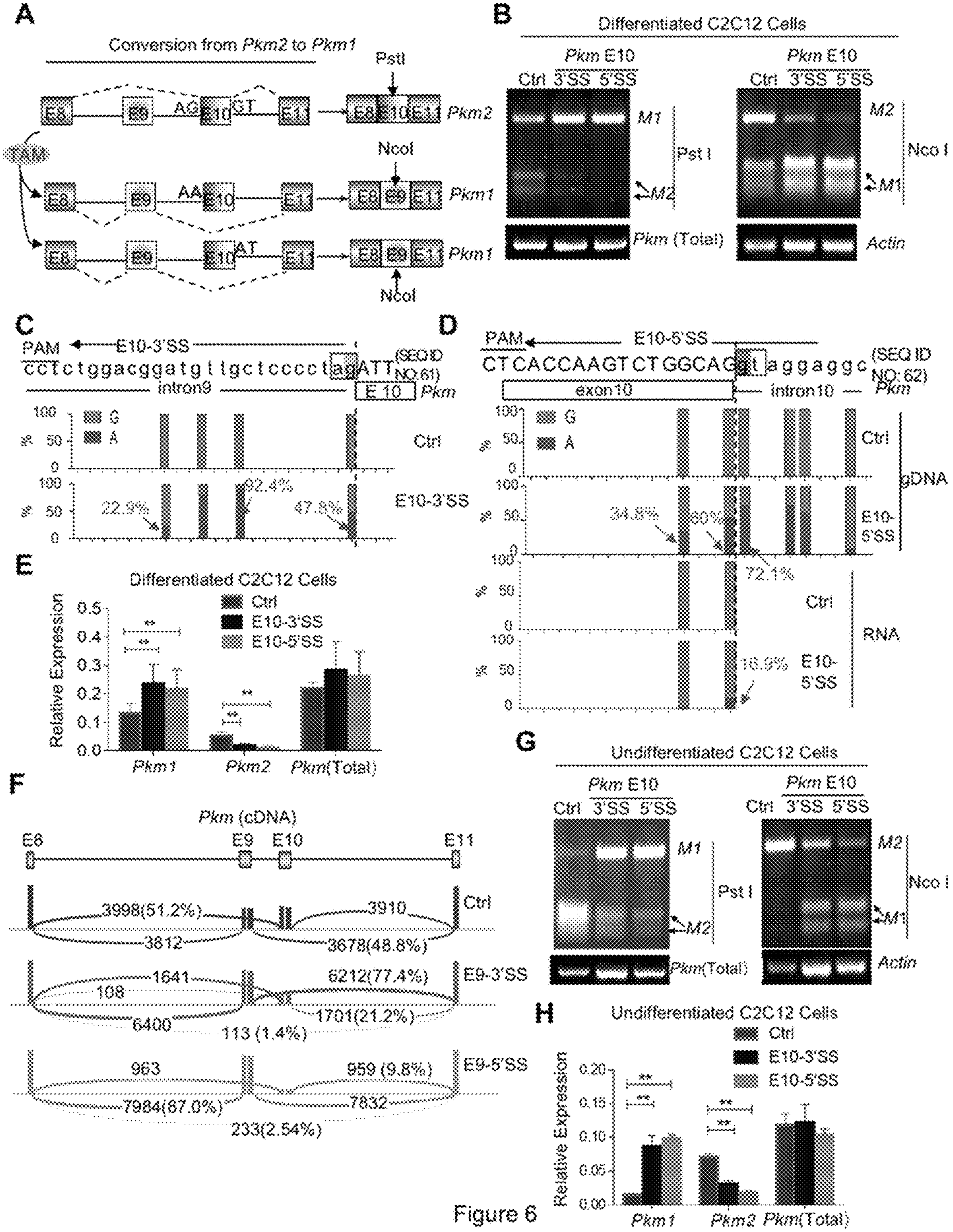
FIG. 6: TAM switched pyruvate kinase M2 (PKM2) to pyruvate kinase M1 (PKM1) by eliminating the 5'SS or 3'SS of exon 10. (A) A schematic diagram showing switching of PKM2 to PKM1 in C2C12 cells by TAM. In the top panel, in WT C2C12 cells, exon 10, not exon 9 of PKM gene, was spliced to produce PKM2, whose cDNA was recognized by the restriction enzyme PstI (top panel); in the bottom panel, TAM converted the GT dinucleotide at the 5'SS of exon 10 to AT (or 3'SS AG to AA). Therefore, exon 9 instead of exon 10 was spliced to produce PKM1, whose cDNA was recognized by the restriction enzyme NcoI. (B) TAM increased PKM1 expression while inhibiting PKM2 expression. C2C12 cells were transfected with TAM and targeting sgRNA (PKM-E10-5'SS or PKM-E10-3'SS) or control sgRNA (Ctrl). Seven days after transfection, the cells were differentiated into muscle cells, then PKM was amplified from the cDNA, and the amplicon was digested with PstI or NcoI. The fragment corresponding to PKM1 or PKM2 is indicated, while GAPDH and total PKM (amplicon of exon 5 and exon 6) are included as vector controls. (C, D) TAM converted the invariant G to A at the 3'SS (C) or 5'SS (D) of PKM exon 10. Intron-exon junctions (SEQ ID NO: 61-62) were amplified from genomic DNA (top 2 panels) or cDNA (bottom 2 panels) and analyzed by high-throughput sequencing. The base composition of each guanine and the percentage of A are described. The data are representative of two independent experiments. (E) Real-time PCR analysis of the ratio of PKM1 to PKM2. The data are representative (B, D, E) or summary of two independent experiments (C). (F) TAM converted PKM2 to PKM1. As in C, the splicing junctions were amplified from cDNA and analyzed by high-throughput sequencing. The Figure shows the coverage and percentage of each splicing junction of the cells treated with control sgRNA (top panel) or E10-5'SS sgRNA (bottom panel). The count and percentage (in parentheses) of the junction readings are depicted on the top of each junction arc. (G, H) Similar to the above, TAM can convert PKM2 to PKM1 in undifferentiated C2C12 cells.

SgRNA (PKM-3'SS-E10 or PKM-5'SS-E10, the sequence of their target binding region is SEQ ID NO: 15 or 16, respectively) for the 3' or 5' splice site of intron 10 were designed and transferred into C2C12 cells to mutate the G to A (FIG. 6, C, D). It was found that in the muscle cells differentiated from C2C12, PKM2 expression was significantly down-regulated and PKM1 expression was up-regulated (FIG. 6, B, E, F). Similarly, in undifferentiated C2C12 cells, PKM2 expression was significantly down-regulated and PKM1 expression was up-regulated (FIG. 6, G, H).

Figure 7:
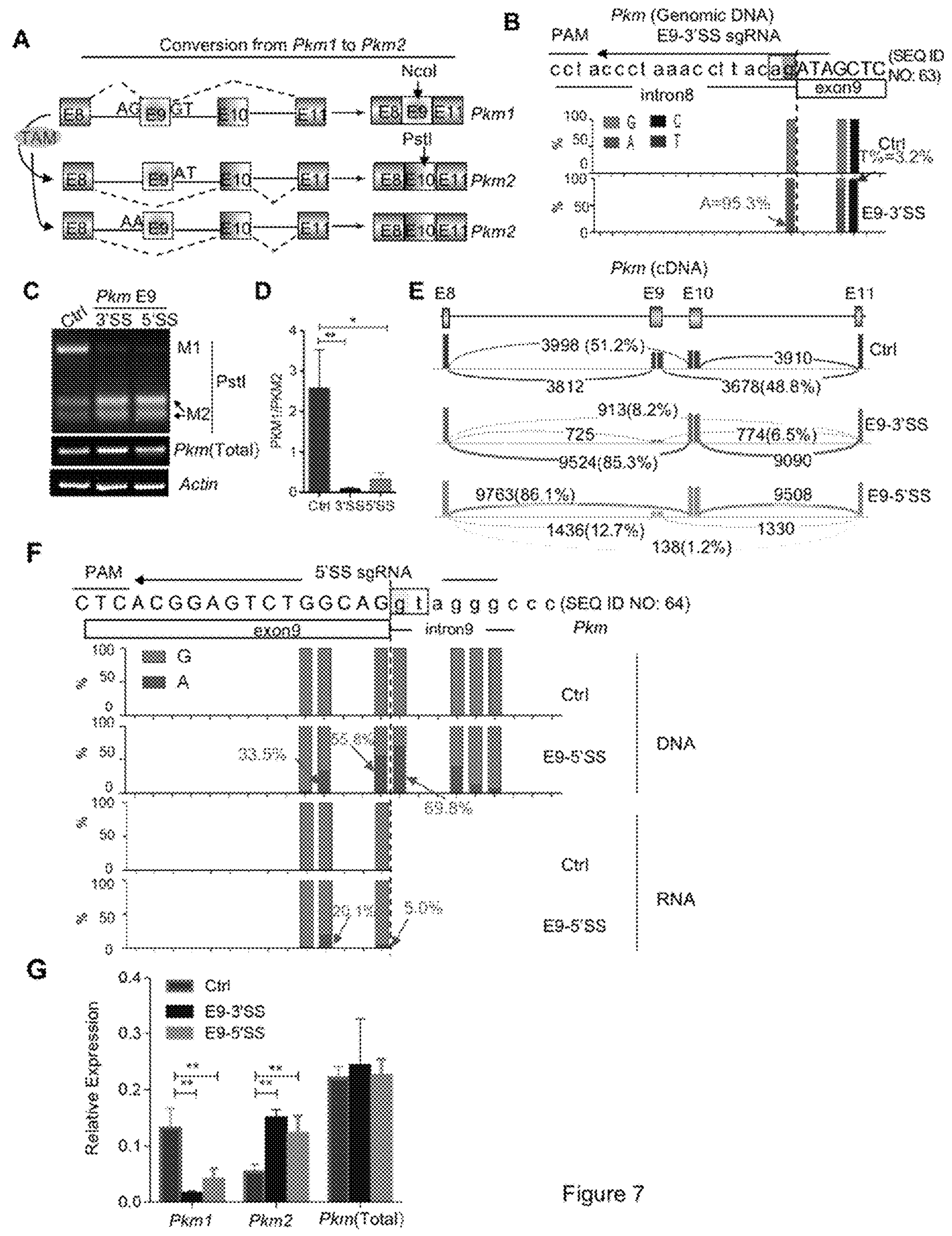
FIG. 7: TAM suppressed the expression of PKM1 by eliminating the 3'SS or 5'SS of the exon 9 of PKM. (A) TAM converted the invariant G at 3'SS or 5'SS of PKM exon 9 to A. (B) Genomic DNA from control or TAM-treated cells (E9-3'SS) of muscle cells differentiated from C2C12 cells was analyzed by high-throughput sequencing (SEQ ID NO: 63, the exon/intron junction sequence). The percentage G or A of each guanine with a mutation frequency more than 1% is depicted. The data are representative of two independent experiments. Note that TAM also caused a C>T mutation in exon 9 at this position. (C, D, E) TAM inhibited PKM1 expression and meanwhile promoted PKM2 expression. (C) PKM was amplified from cDNA, and the amplicon was digested with NcoI. The fragment corresponding to PKM1 or PKM2 is indicated, while GAPDH and total PKM (amplicon of exon 5 and exon 6) are included as vector controls. (D) The expression of PKM1 and PKM2 was measured by real-time PCR, and the ratio of PKM1 to PKM2 was calculated. (E) The splicing junctions were amplified from cDNA and analyzed by high-throughput sequencing. The Figure shows the coverage and percentage of each splicing junction of the cells treated with control sgRNA (top panel) or E9-3'SS sgRNA (bottom panel). The count and percentage (in parentheses) of the junction readings are depicted on the top of each junction arc. The data are summary of two independent experiments. ***, p<0.0001 in student's t test. (F) As above, genomic DNA from control or TAM-treated cells (E9-5'SS) of muscle cells differentiated from C2C12 cells was analyzed by high-throughput sequencing (SEQ ID NO: 64, the exon/intron junction sequence). The percentage G or A of each guanine with a mutation frequency more than 1% is depicted. The data are representative of two independent experiments. (G) Real-time quantitative PCR analysis of PKM1 and PKM2 expression.

By the sgRNA (PKM-3'SS-E9, PKM-5'SS-E9, their target binding region is shown in SEQ ID NO: 13 or 14, respectively) targeting the 5' or 3' splice site of intron 9, the G could be mutated to A, while PKM1 expression level was down-regulated (FIG. 7) and PKM2 expression was up-regulated. This further proved that the mutation of the splice site(s) can change the selection of the splice site(s) of mutually exclusive exons.

8. Inducing Intron Retention

Intron retention is another type of alternative splicing, and recent studies have shown that intron retention occurs in many human diseases including tumors. We demonstrated that the use of TAM and sgRNA to disrupt the splice site(s) of a corresponding intron can specifically induce intron retention.

BAP1 is a histone deubiquitinase, and its second intron is retained in some tumors, causing a decrease in BAP1 expression. The second intron of BAP1 may be spliced in an intron-defined manner, wherein the 5'SS is paired with the downstream 3'SS. The G is converted to A, and U1 recognizes U1 RNP at 5'SS and destroys the intron definition, resulting in the inclusion of the intron. This experiment used TAM to mutate G at the 5' splice site of intron 2 of BAP1, the schematic diagram of which is shown in FIG. 8(A).

Figure 8:
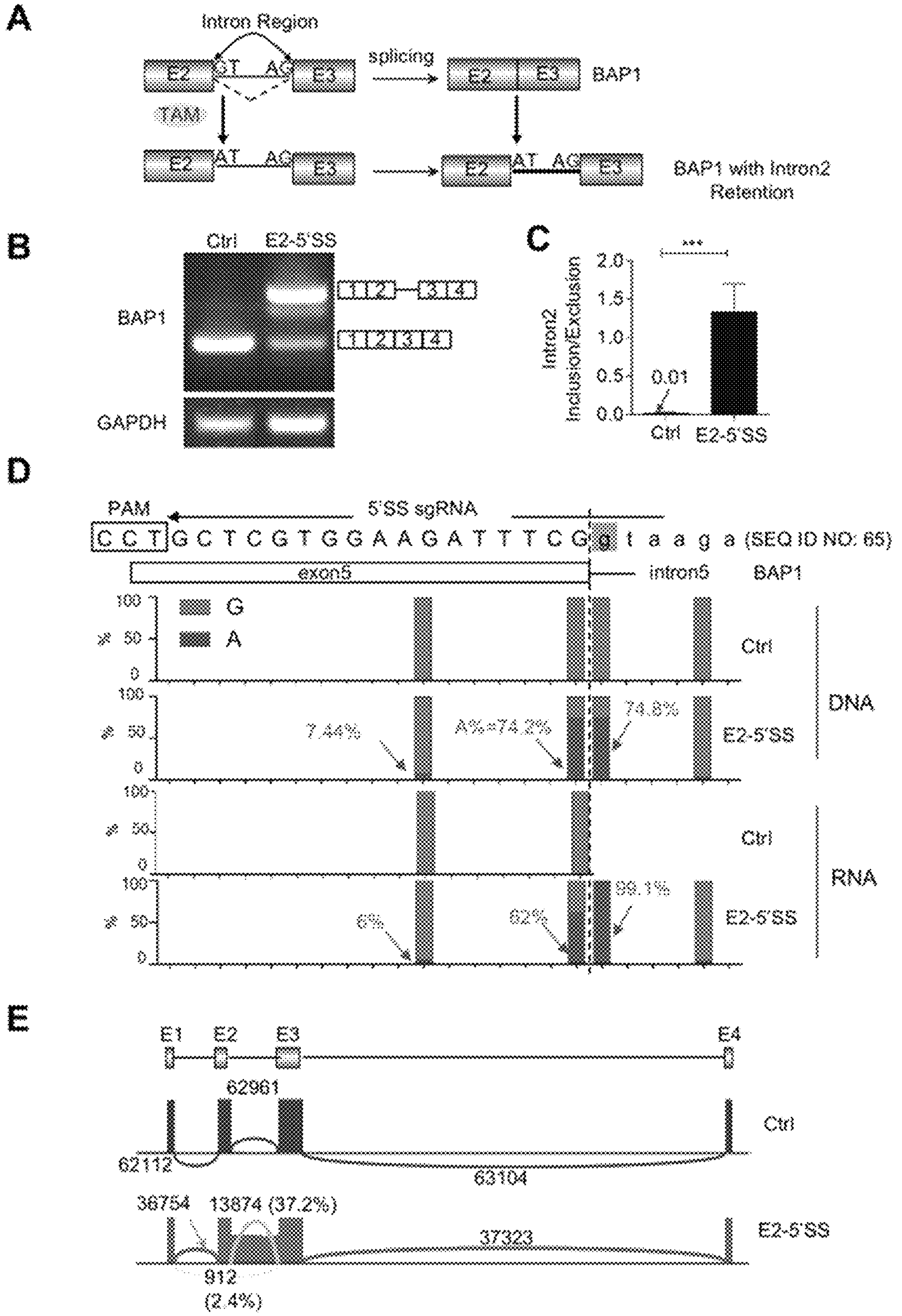
FIG. 8: After TAM converted the invariant G to A on the 5'SS, intron 2 of BRCA1-associated protein 1 (BAP1) was retained. (A) A schematic diagram of directing TAM to mutate the invariant G at the 5' splice site of BAP1 exon 2 and showing its retention. The second intron of BAP1 may be spliced in an intron-defined manner, wherein the 5'SS is paired with the downstream 3'SS. The invariant G was converted to A, and U1 recognized U1 RNP at 5'SS and destroyed the intron definition, resulting in the inclusion of the intron. (B, C) TAM induced the retention of BAP1 intron 2. 293T cells were transfected with the expression plasmid (s) of AIDx-nCas9-UGI and the sgRNA targeting AAVS1 (Ctrl) or sgRNA targeting 5'SS of BAP1 exon 2 (NAP1-E2-5'SS). Seven days after transfection, BAP1 mRNA splicing was analyzed by RT-PCR (B) or isoform-specific real-time PCR (C). (D) The retained intron contained a 5'SS G>A mutation. Intron-exon junctions (SEQ ID NO: 65) were amplified from genomic DNA (top 2 panels) or cDNA (bottom 2 panels) of 293T cells treated with control sgRNA (ctrl) or targeting sgRNA (E2-5'SS). The base composition of each guanine with a detectable mutation is depicted. The locations of the sgRNA and PAM sequences are marked on the top of the intron-exon junction sequence. Intron/exon junctions are depicted using dashed lines. The data are representative of two independent experiments. Note that because intron 2 was effectively spliced in control cells, only cells receiving E2-5'SS sgRNA had readings that covered the intron, and 99% of them contained the G>A mutation. (E) Mutated 5'SS induced retention of the second intron, instead of skipping the second exon in BAP1. As in D, the splicing junctions were amplified from cDNA and analyzed by high-throughput sequencing. The Figure shows the coverage and percentage of each splicing junction of the cells treated with control sgRNA (top panel) or E2-5'SS sgRNA (bottom panel). The count and percentage (in parentheses) of the junction readings are depicted on the top of each junction arc. Note that, in sgRNA-treated cells, 2.4% of the mRNAs were spliced to skip the second exon, while more than 60% retained the second intron. The data are representative (B, D, E) or summary (C) of two independent experiments.
Figure 9:
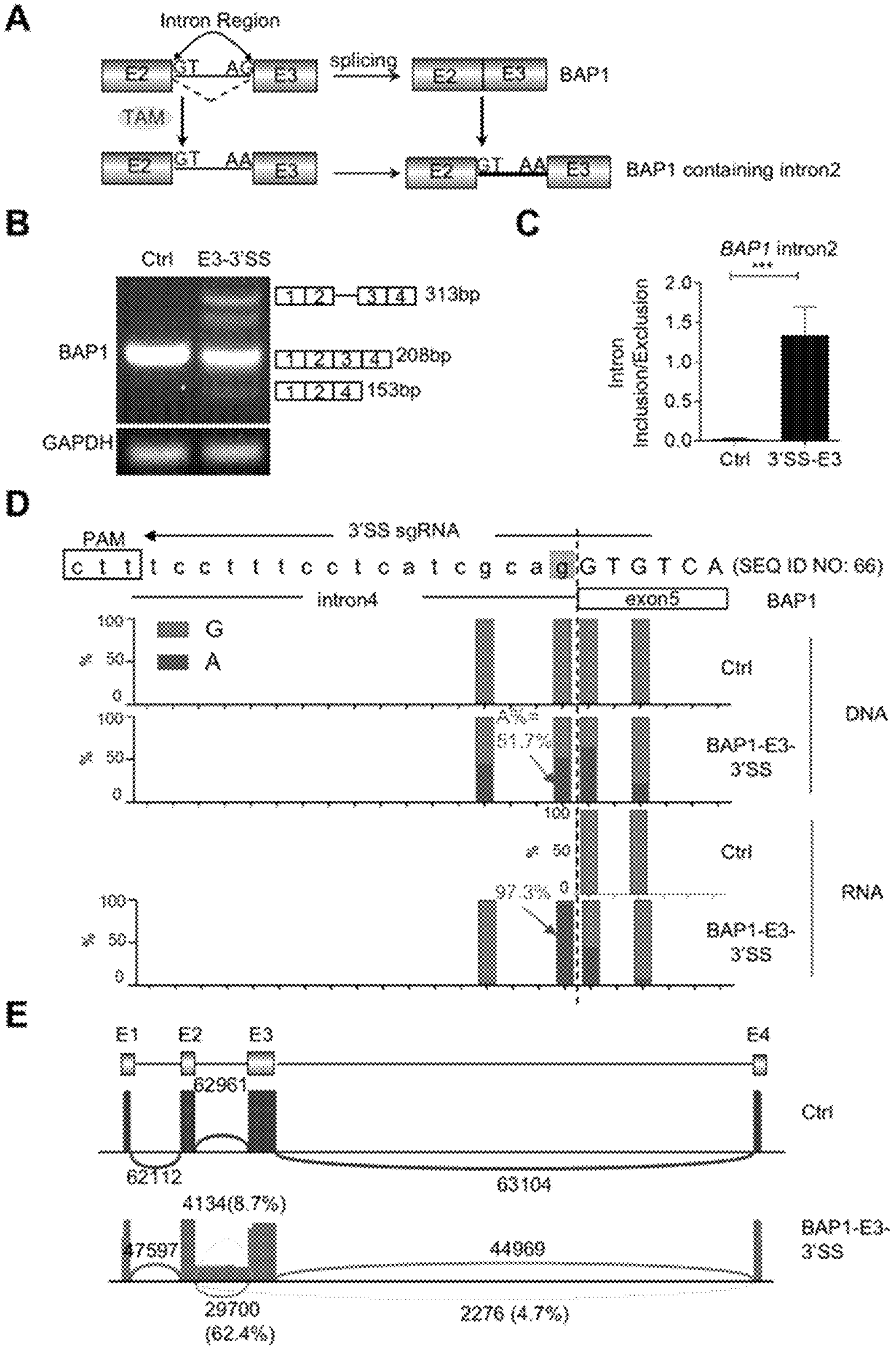
FIG. 9: Conversion of invariant G to A at the 3'SS of exon 3 of BAP1 resulted in its retention. (A) A schematic diagram of directing TAM to mutate the invariant G at the 3'SS of BAP1 exon 3 and directing its retention. (B, C) TAM induced the retention of BAP1 intron 2. 293T cells were transfected with the expression plasmid(s) of AIDx-nCas9-UGI and the sgRNA targeting AAVS1 (Ctrl) or 3'SS of BAP1 intron 2. Seven days after transfection, BAP1 mRNA splicing was analyzed by RT-PCR (B) and isoform-specific real-time PCR (C). (D) The retained second intron contained a G>A mutation at 3'SS. 5'SS was amplified from genomic DNA (top 2 panels) or cDNA (bottom 2 cells) of 293T cells treated with control sgRNA (Ctrl), or sgRNA targeting 3'ss (E3-3'SS). The base composition of each guanine with a detectable mutation is depicted (G>A conversion efficiency is more than 0.1%). The locations of the sgRNA and PAM sequences are shown on the top of the intron-exon junction sequence (SEQ ID NO: 66). Intron/exon junctions are depicted using dashed lines. The data are representative of two independent experiments. Note that because intron 2 was effectively spliced in Ctrl cells, only cells receiving E3-3'SS sgRNA had readings that covered the intron. (E) TAM mainly induced the retention of the second exon of BAP1. As in D, the splicing junctions were amplified from cDNA and analyzed by high-throughput sequencing. The Figure shows the coverage and percentage of each splicing junction of the cells treated with control sgRNA (top panel) or E3-3'SS sgRNA (bottom panel). The count and percentage (in parentheses) of the junction readings are depicted on the top of each junction arc. Note that, in sgRNA-treated cells, 4.7% of the mRNAs skipped the third exon, 8.7% used the downstream cryptic splice site, while more than 20% retained the second intron. The data are representative (B, D, E) or summary (C) of two independent experiments.

SgRNA (BAP1-E2-5'SS, its target binding region is shown in SEQ ID NO: 5) targeting the 5' splice site of intron 2 was designed. 293T cells were transfected with the expression plasmid of AIDx-nCas9-UGI and the expression plasmid of the sgRNA targeting AAVS1 (Ctrl) or BAP1 intron 2. Seven days after transfection, BAP1 mRNA splicing was analyzed by RT-PCR (FIG. 8, B) or isoform-specific real-time PCR (FIG. 8, C). The results show that more than 70% of Gs were mutated to As (FIG. 8, D). After mutation, the retention of intron 2 was induced, and more than 60% of the BAP1 mRNAs contained intron 2; similarly, mutation of the 3' splice site of the intron 2 (sgRNA sequence is shown as SEQ ID NO: 6 (BAP1-E3-3'SS)) also induced BAP1 intron retention (FIG. 9, B-E).

9. C to T Mutation at 3' Splice Site-3 Positon can Promote Exon Inclusion

In addition to splice sites, other cis-acting elements on mRNA can also change the splicing process of pre-mRNA, therefore TAM technology can also be used to edit other splicing regulatory elements. Because changes in introns do not affect the sequences for gene expression, we focused on the editing of splicing regulatory elements of intron. A polypyrimidine chain consisting of cytosine (C) and thymine (T) is present upstream of the 3' splice site. This experiment proved that the C in the polypyrimidine chain can be mutated to T by TAM and the corresponding sgRNA, therefore enhancing the strength of the 3' splice site and promoting the inclusion of downstream exons.

Figure 11:
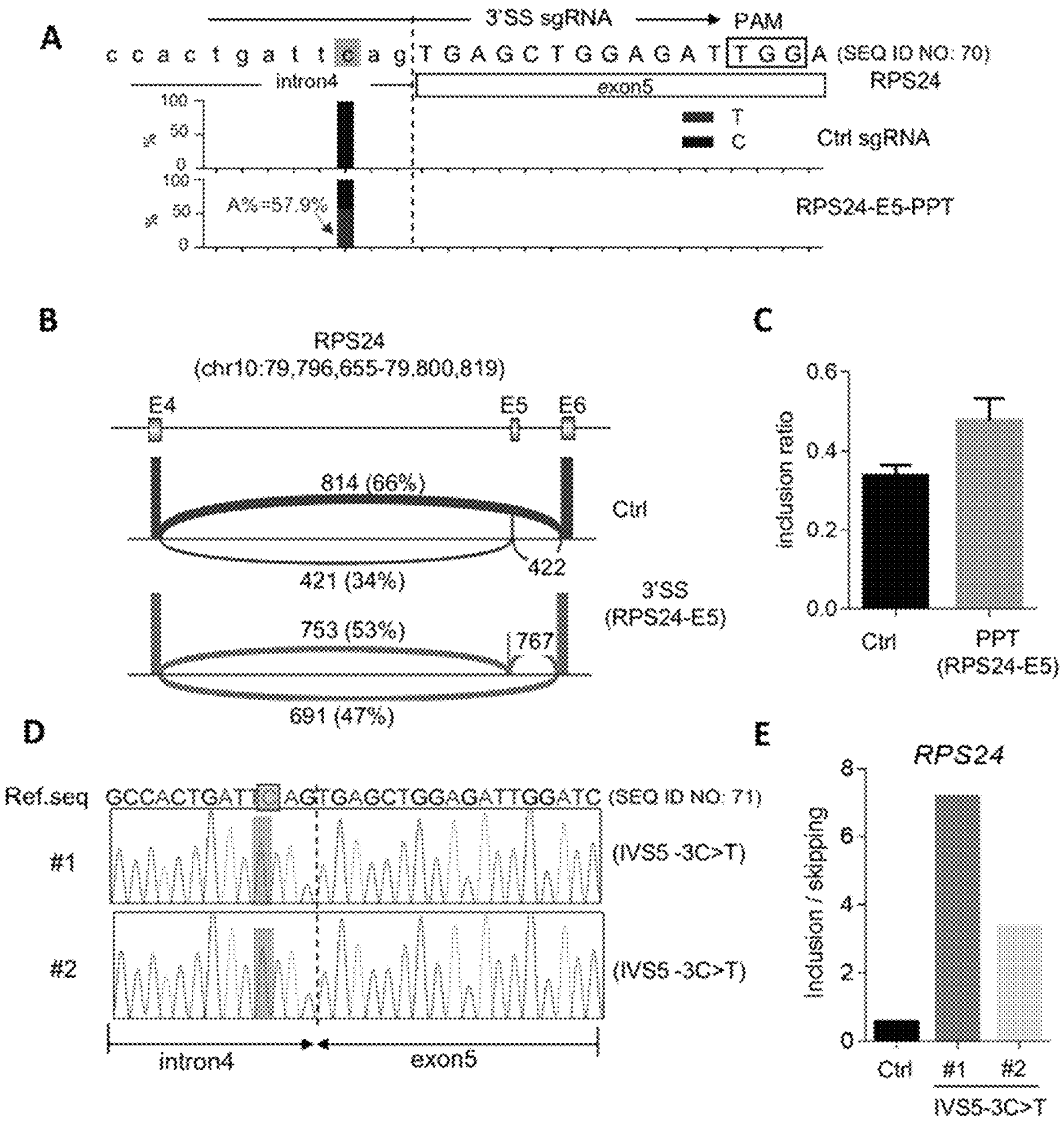
FIG. 11: Polypyrimidine Tract (PPT) upstream of RPS24 exon 5 converted C to T to enhance its inclusion. (A) TAM converted C to T at the PPT of exon 5 of RPS24 (SEQ ID NO: 70, the exon/intron junction sequence). 293T cells were transfected with expression plasmid(s) of AIDx-nCas9-UGI and sgRNA targeting AAVS1 (Ctrl) or polypyrimidine nucleoside of the fifth exon in RPS24 (PPT-E5RPS25). Six days after transfection, sgRNA targeting regions were amplified from genomic DNA and analyzed by high-throughput sequencing with over 8000× coverage. The percentage of each cytosine having a detectable mutation (>0.1%) is depicted, and the data are representative of two independent experiments. (B, C) As in A, TAM enhanced the inclusion of the fifth exon of RPS24. RPS24 mRNA splicing was analyzed by high-throughput sequencing for junctions amplified from cDNA (B) or isoform-specific real-time PCR (C). (D, E) Conversion of PPT from C to T increased the content of exon 6 of RPS24. Two single-cell clones were derived from TAM-treated cells and analyzed by Sanger sequencing (D, SEQ ID NO: 71, the reference sequence). The right shows the genotype of the cloned cells. (E) The content of RPS24 exon 6 was determined by isoform-specific real-time PCR. The data are representative (A, B, D) or summary (C, E) of two independent experiments.

293T cells were transfected with the expression plasmid of AIDx-nCas9-UGI and the expression plasmid of sgRNA targeting AAVS1 (Ctrl) or sgRNA targeting polypyrimidine nucleosides of the fifth exon in RPS24 (RPS24-E5-PPT, its target binding region is shown as SEQ ID NO: 10). Six days after transfection, sgRNA targeting regions were amplified from genomic DNA and analyzed by high-throughput sequencing with over 8000× coverage. The results show that more than 50% of the Cs in the polypyrimidine chain were mutated to Ts. It was found that the inclusion rate of exon 5 increased (FIG. 11, B, C). After sorting, two single-cell clones containing complete C to T mutations were obtained, and their inclusion rate of exon 5 was increased by 8-fold and 5-fold, respectively (FIG. 11, E).

Figure 10:
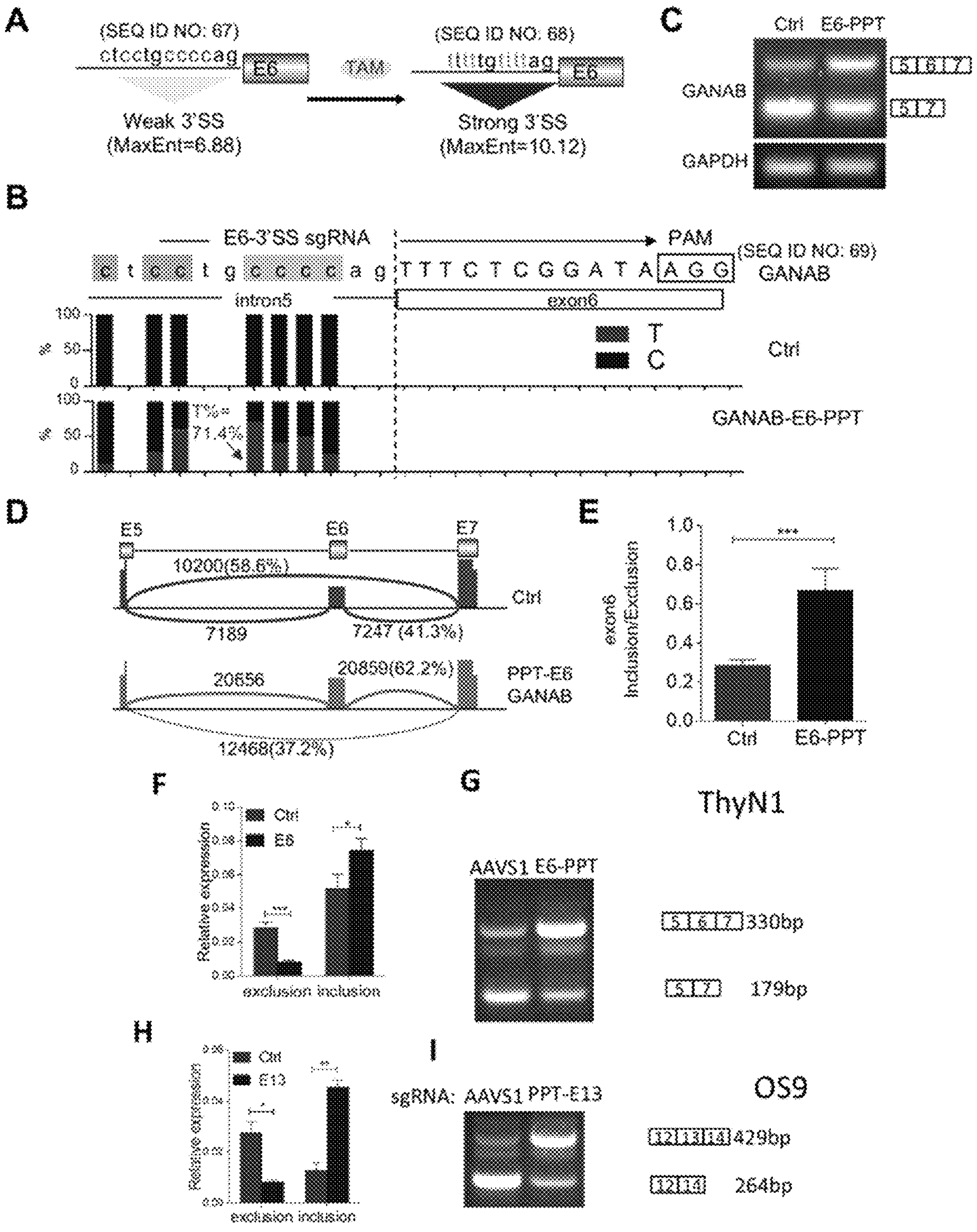
FIG. 10: Polypyrimidine Tract (PPT) upstream of glucosidase II alpha subunit (GANAB) exon 6 converted Cs to Ts to enhance its inclusion. (A) A schematic diagram of directing TAM to convert Cs to Ts at the PPT of GANAB exon 6 to enhance the strength of 3'SS. The polypyrimidine polysaccharide of GANAB exon 6 contains multiple Cs (left, SEQ ID NO: 67) and converting these Cs to Ts (right, SEQ ID NO: 68) increased the strength of this 3'SS (from 6.88 to 10.12) and enhanced the inclusion of exon 6. (B) TAM converted the PPT of GnAB exon 6 to Ts. 293T cells were transfected with the expression plasmid of AIDx-nCas9-UGI and control sgRNA (Ctrl) or the sgRNA targeting the PPT of GANAB exon 6 (PPT-E6 GANAB). Six days after transfection, sgRNA targeting regions were amplified from genomic DNA and analyzed by high-throughput sequencing with over 8000× coverage. The base composition of nucleotides having detectable mutations (>0.1%) is depicted. The locations of the sgRNA and PAM sequences are shown on the top of the junction sequence (SEQ ID NO: 69). Intron/exon junctions are depicted using dashed lines. The data are representative of two independent experiments. (C, D, E) TAM enhanced the inclusion of the sixth exon in GANAB. (C) As in B, the splicing junctions were amplified from cDNA and analyzed by high-throughput sequencing. The Figure shows the coverage and percentage of each splicing junction of the cells treated with control sgRNA (top panel) or PPT-E6 GANAB sgRNA (bottom panel). The count and percentage (in parentheses) of the junction readings are depicted on the top of each junction arc. (D, E) Analysis of GANAB mRNA splicing by RT-PCR (D) or isoform-specific real-time PCR (E). The data are representative (C, D) or summary (E) of two independent experiments. (F, G) TAM promoted the inclusion of the sixth exon in thymosin N1 (ThyN1). (H, I) TAM enhanced the inclusion of the 13th exon in OS9.

In addition, 293T cells were transfected with the expression plasmid of AIDx-nCas9-UGI and the expression plasmid of control sgRNA (Ctrl) or sgRNA targeting PPT of exon 6 in GANAB (GANAB-E6-PPT, its target binding region is shown as SEQ ID NO: 4). Six days after transfection, sgRNA targeting regions were amplified from genomic DNA and analyzed by high-throughput sequencing with over 8000× coverage. The results are shown in FIG. 10 (B-E), wherein multiple Cs were induced to mutate to Ts, with the highest being intron 5 (IVS5)-6C, in which more than 70% of the Cs were mutated to Ts. High-throughput sequencing proved that the inclusion of exon 6 was increased by 50%. Similar methods could also cause the increase of the inclusion of ThyN1 exon 6 (the target binding region of the sgRNA is shown in SEQ ID NO: 12, THYN1-E6-PPT) (FIG. 10, F-G) and the increase of the inclusion of OS9 exon 13 (the target binding region of the sgRNA is shown in SEQ ID NO: 11, OS9-E13-PPT) (FIG. 10, H-I).

10. TAM Technology can Restore DMD Protein Expression in Human iPS Cells and Mdx Mouse Models (C2C12 and iPS) Duchenne muscular dystrophy (DMD) is a muscular dystrophy disease. There is one case for every 4,000 men in the United States. The heritable mutation of the patient's DMD gene leads to the change of the gene's open reading frame or the formation of immature codons, resulting in dystrophin defects in skeletal muscle and the occurrence of the disease. Compared with the mutated DMD gene, the truncated dystrophin retains partial function, resulting in Becker muscular dystrophy with mild symptom. Therefore, some studies have used antisense oligonucleotides or double sgRNA-mediated CRISPR technology to skip some exons, so that to restore the open reading frame of DMD and promote the expression of dystrophin. This method of partially restoring the expression of dystrophin by skipping the non-essential regions of the DMD gene is expected to benefit 80% of DMD patients. However, treatment by antisense oligonucleotides requires continuous administration, which is extremely time-consuming and expensive. It is necessary to develop a new DMD gene therapy.

Figure 12:
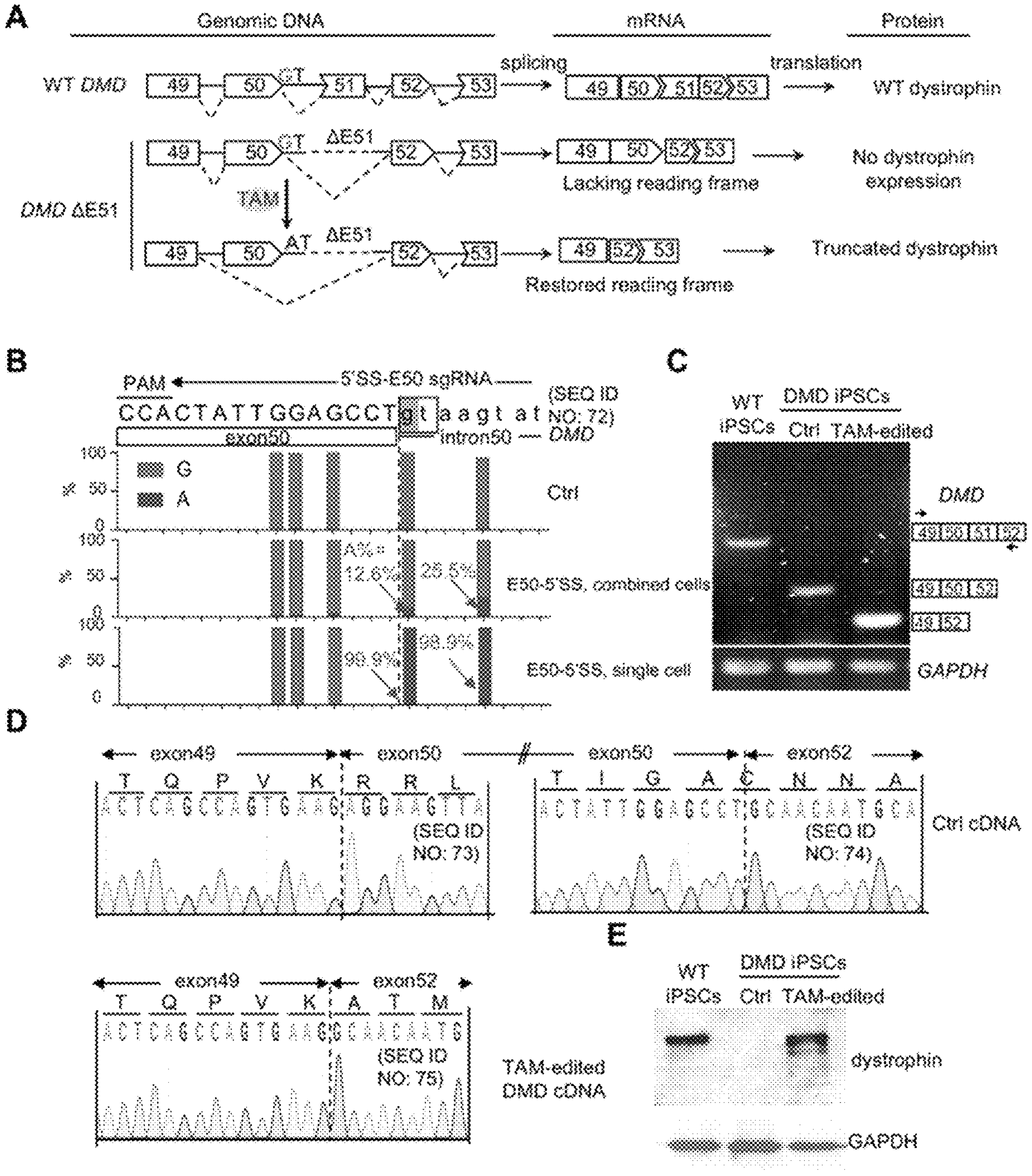
FIG. 12: TAM was used to induce exon skipping, repair reading frame of the dystrophin (DMD) gene, and restore expression of dystrophin (DMD) in cells of a Duchenne muscular dystrophy patient. (A) A schematic diagram of directing TAM to convert G at 5'SS of DMD exon 50 to A, and restore the expression of dystrophin protein in the patient's cells. Compared with WT cells (top panel), the patient lost exon 51 due to a genetic mutation, resulting in a damage to the reading frame of dystrophin and complete loss of dystrophin (middle panel); a GU>AU mutation at the 5'SS of exon 50 by TAM led to skipping of exon 50 in pateint's cells and restored the reading frame and expression of dystrophin. (B) After treating induced pluripotent stem cells (iPSCs) of the Duchenne muscular dystrophy patient with control sgRNA (ctrl) or targeting sgRNA (E50-5'SS), the corresponding DNA was amplified by PCR, and the induced mutations were analyzed by high-throughput sequencing (SEQ ID NO: 72, the exon/intron junction sequence). The data are representative of two independent experiments. (C, D) Normal human-derived iPSCs, patient-derived iPSCs, and repaired patient-derived iPSCs were differentiated into cardiomyocytes, and DMD gene expression was detected by RT-PCR (C) or western blot (D, SEQ ID NO: 73-75), respectively. (E) The repaired cells precisely spliced exons 49 and 52.
Figure 13:
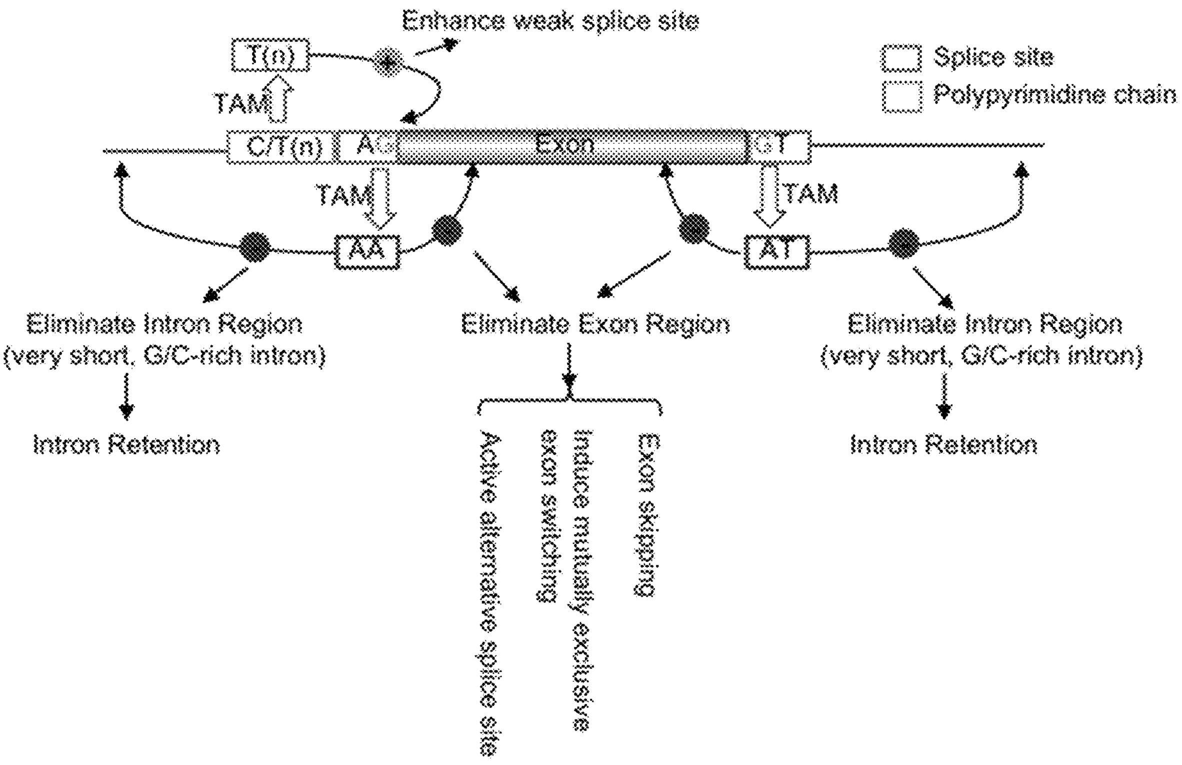
FIG. 13: A schematic diagram of using TAM technology to regulate RNA splicing. Using TAM technology to mutate GT to AT at the 5' splice site of an intron can induce exon skipping, activate alternative splice sites, induce mutually exclusive exon switching or intron retention; to mutate AG to AA at the 3' splice site of an intron can also induce exon skipping, activate alternative splice sites, induce mutually exclusive exon switching or intron retention; to mutate C to T in the pyrimidine region at the 3' end of an intron can enhance weak splice sites, thereby enhancing exon inclusion.

In order to find out whether TAM technology can regulate exon skipping of the DMD gene, iPS cells of a DMD patient lacking exon 51 is used in this experiment. According to the results of sequence analysis, after skipping of exon 50 by the sgRNA (the sequence of its target binding region is shown as SEQ ID NO: 17, DMD EXON50 5'SS), the open reading frame of dystrophin protein was restored (FIG. 12). The iPSCs from the patient were transfected with the expression plasmid of sgRNA (the sequence of the target binding region is shown in SEQ ID NO: 17) and the expression plasmid of AIDx-nCas9-UGI. High-throughput sequencing shows that it can induce more than 12% of G>A mutations (FIG. 12, B), and then a monoclonal cell having complete G>A mutations were obtained (FIG. 12B). Then the iPSCs were differentiated into cardiomyocytes and it was found that the TAM-edited cells had exon 50 skipping (FIG. 12C, D). Further, western bloting shows that the expression of the dystrophin protein was restored in the TAM-repaired cells (FIG. 12, E).

Figure 14:
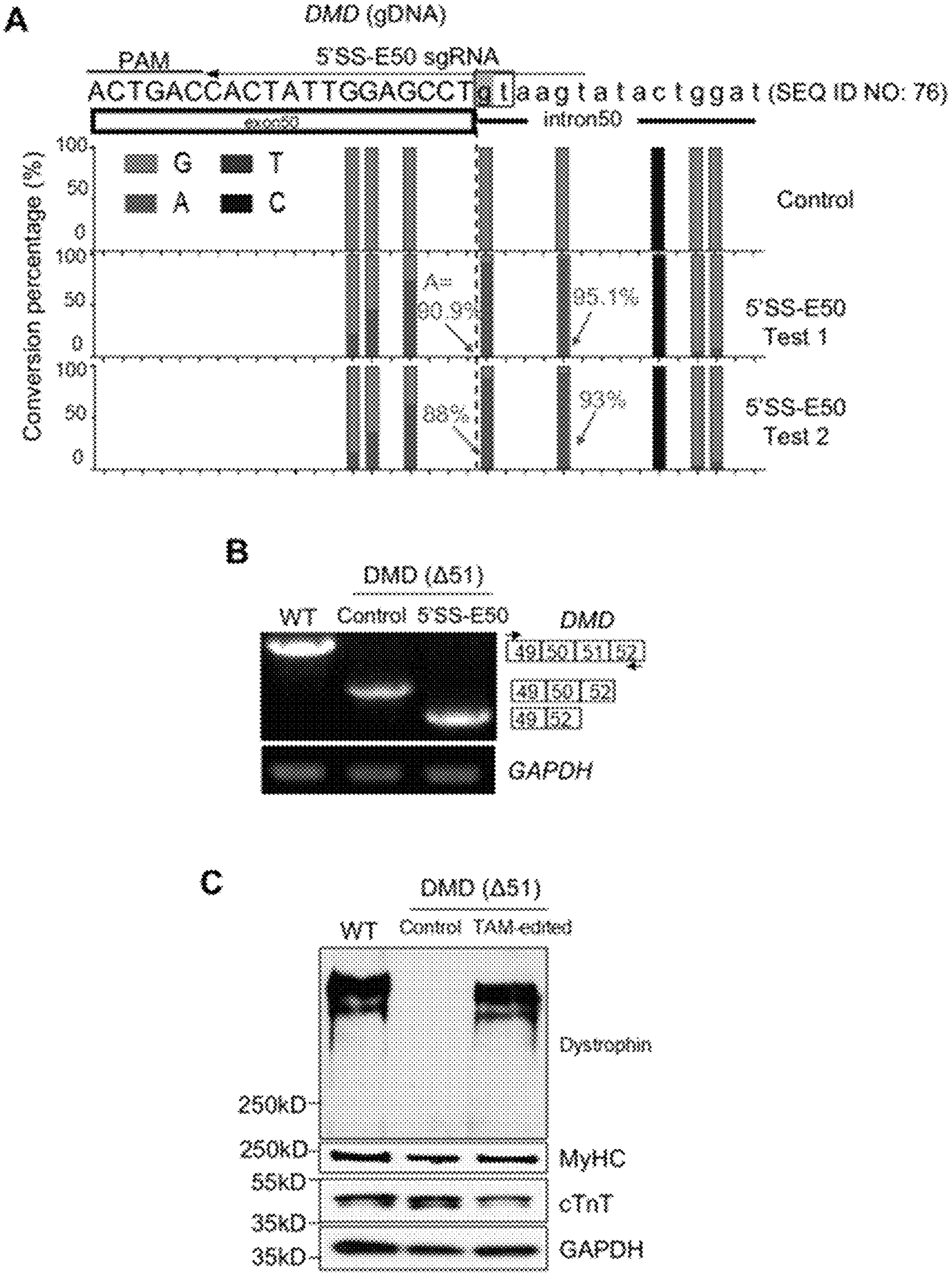
FIG. 14: TAM was used to induce exon skipping, repair reading frame of the DMD gene, and restore expression of dystrophin (DMD) in cells of Duchenne muscular dystrophy patients. (A) After treating iPSCs of the Duchenne myasthenia patient with control sgRNA (ctrl) or targeting sgRNA (E50-5'SS) together with AIDx-saCas9 (KKH, nickase)-UGI, the corresponding DNA was amplified by PCR, and the induced mutations were analyzed by high-throughput sequencing (SEQ ID NO: 76, the exon/intron junction sequence). The data are representative of two independent experiments. (B, C, D) Normal human-derived iPSCs, patient-derived iPSCs, and repaired patient-derived iPSCs were differentiated into cardiomyocytes, and the expression of the DMD gene and dystrophin was detected by RT-PCR or western blot or immunofluorescence staining, respectively. (E, F, G) The results show that the repaired cardiomyocytes reversed the amyasthenia phenotype. Creatine kinase release induced by hypotonicity (E), miR31 expression (F), and the expression of β-dystrophin proteoglycan protein (G) proved that the repaired cardiomyocytes reversed the phenotype of amyasthenia. (H, I) The whole-genome sequencing proved the high specificity of the gene editing, with only one off-target site found in two whole-genome sequencing (SEQ ID NO: 77, off-target sequence; SEQ ID NO: 78, on-target sequence).
Figure 14:
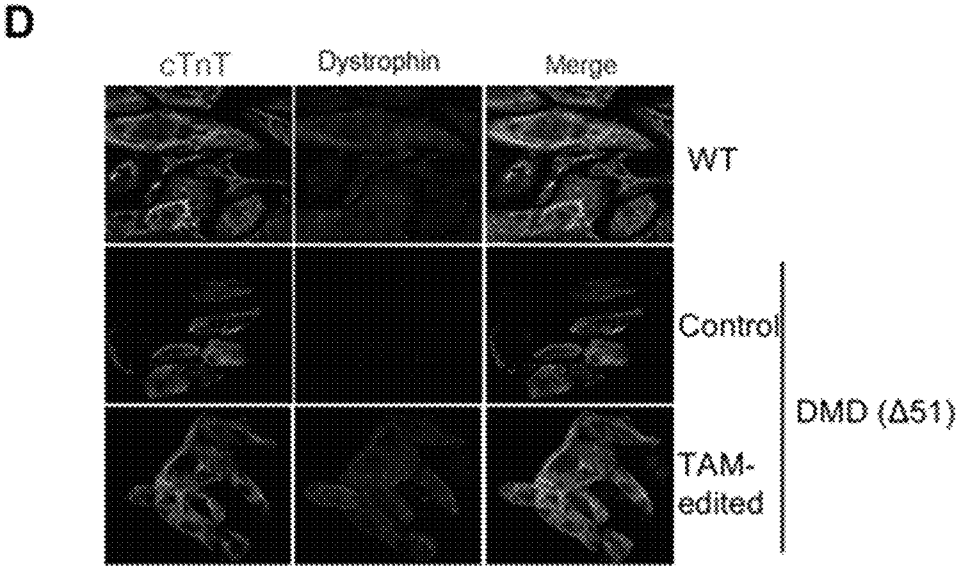
Figure 14:
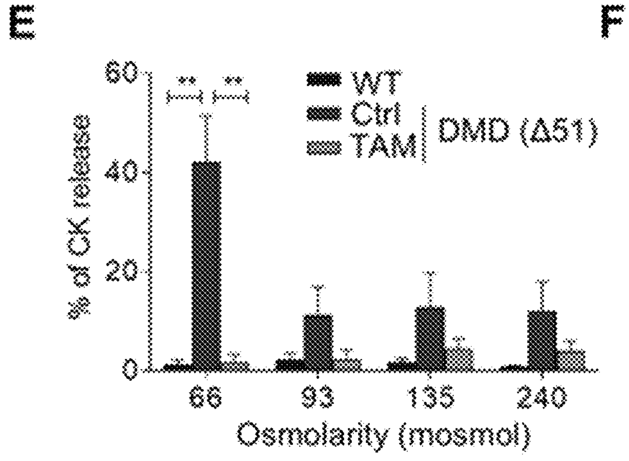
Figure 14:
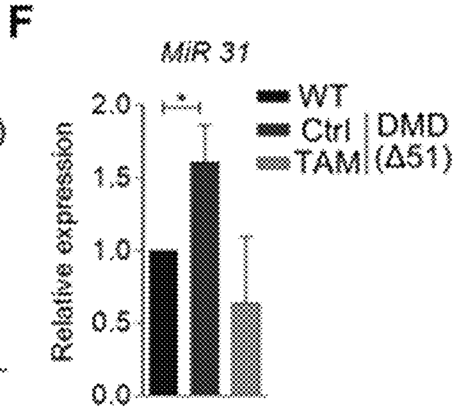
Figure 14:
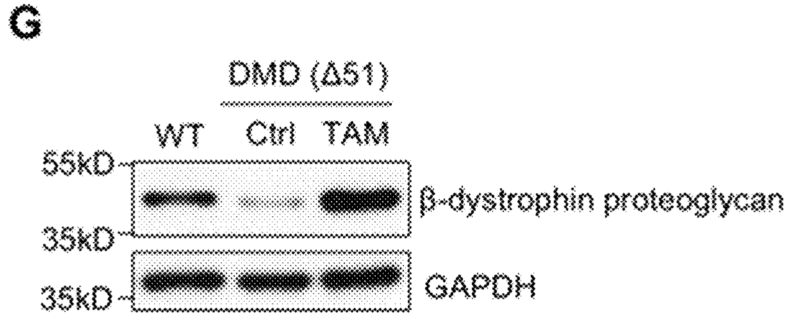
Figure 14:
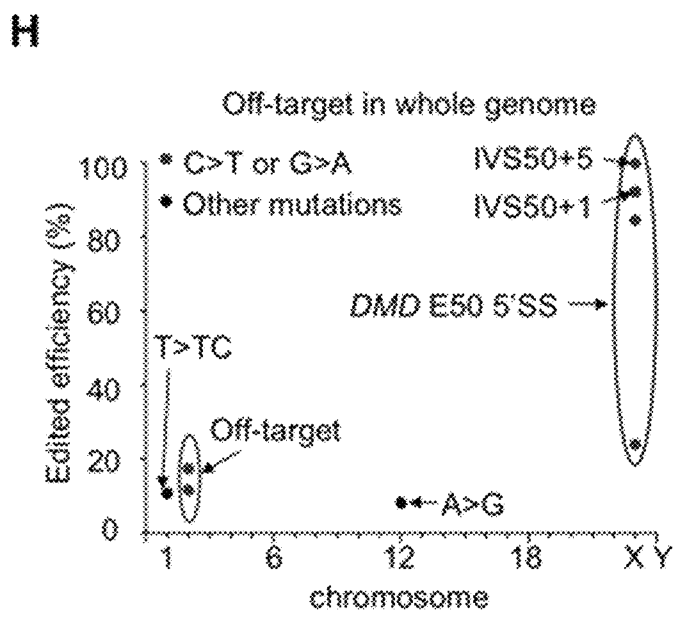
Figure 14:
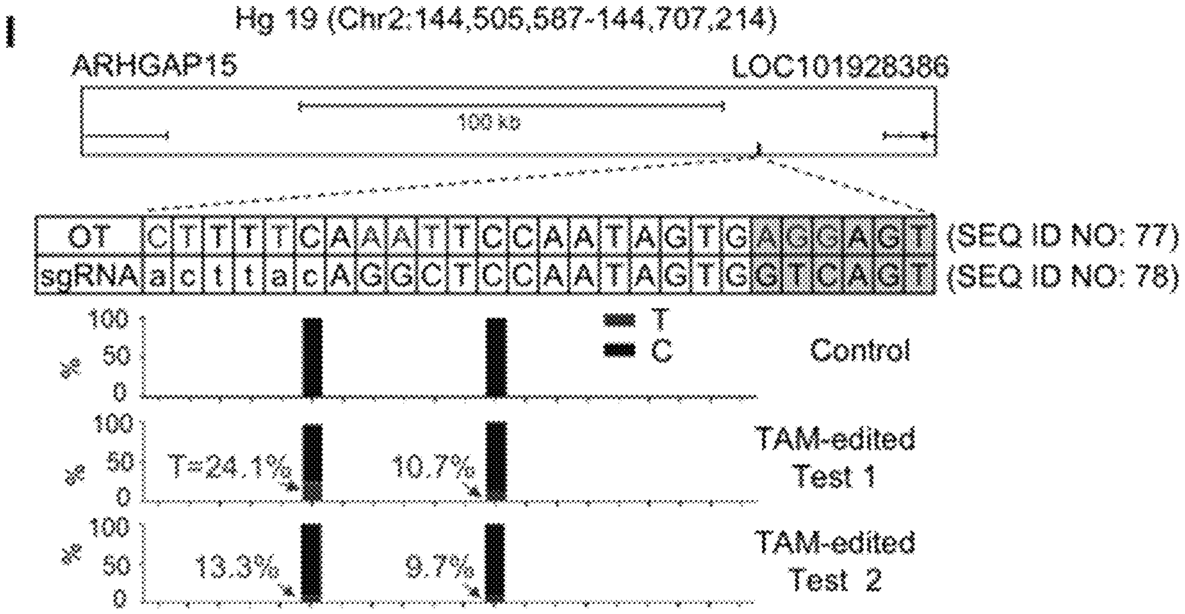

Using the same experiment, skipping of DMD exon 50 was induced by AIDx-saCas9 (KKH, nickase)-UGI (coding sequence: SEQ ID NO: 49, amino acid sequence: SEQ ID NO: 50) and the corresponding sgRNA sequence (the sequence is shown in SEQ ID NO: 51, and its backbone sequence is shown in SEQ ID NO: 52). Specifically, after treating iPSCs of the Duchenne myasthenia patient with control sgRNA (ctrl) or targeting sgRNA (E50-5'SS) together with AIDx-saCas9 (KKH, nickase)-UGI, the corresponding DNA was amplified by PCR, and the induced mutations were analyzed by high-throughput sequencing. The data are representative of two independent experiments. The results are shown in FIG. 14(A) (SEQ ID NO: 76, the exon/intron junction sequence). Normal human-derived iPSCs, patient-derived iPSCs, and repaired patient-derived iPSCs were differentiated into cardiomyocytes, and the expression of the DMD gene and dystrophin was detected by RT-PCR or western blot or immunofluorescence staining, as shown in FIG. 14, B, C and D, respectively. FIG. 14, E, F, and G shows that the repaired cardiomyocytes reversed the amyasthenia phenotype. Creatine kinase release induced by hypotonicity (E), miR31 expression (F), and the expression of P-dystrophin proteoglycan protein (G) proved that the repaired cardiomyocytes reversed the phenotype of amyasthenia. In addition, whole-genome sequencing proved the high specificity of the gene editing, with only one off-target site found in two whole-genome sequencing (FIG. 14, H and I (SEQ ID NO: 77, off-target sequence; SEQ ID NO: 78, on-target sequence)).

The sequence involved in this disclosure is as follows:

| Sequence No. | Name |
|---|---|
| 1 | CD45-E5-5'SS |
| 2 | CD45-E5-3'SS |
| 3 | STAT3-E23-3'SS |
| 4 | GANAB-E6-PPT |
| 5 | BAP1-E2-5'SS |
| 6 | BAP1-E3-3'SS |
| 7 | TP53-E8-5'SS |
| 8 | TP53-E9-3'SS |
| 9 | RPS24-E5-5'SS |
| 10 | RPS24-E5-PPT |
| 11 | OS9-E13-PPT |
| 12 | THYN1-E6-PPT |
| 13 | PKM-3'SS-E9 |
| 14 | PKM-5'SS-E9 |
| 15 | PKM-3'SS-E10 |
| 16 | PKM-5'SS-E10 |
| 17 | DMD EXON50 5'SS |
| 18 | primer |
| 19 | |
| 20 | |
| 21 | |
| 22 | AIDX-XTEN-nC AS9 |
| 23 | AIDX-XTEN-nC AS9 |
| 24 | dcas9-AID |
| 25 | dcas9-AID |
| 26 | dcas9-aidm |

-continued

| Sequence No. | Name |
|---|---|
| 27 | dcas9-aidm |
| 28 | AIDx-XTEN-dCas9 |
| 29 | AIDx-XTEN-dCas9 |
| 30 | dCas9-XTEN-AID P182X K10E T82I E156G |
| 31 | dCas9-XTEN-AID P182X K10E T82I E156G |
| 32 | ncas9-P182x |
| 33 | ncas9-P182x |
| 34 | PAM sequence |
| 35 | |
| 36 | |
| 37 | |
| 38 | |
| 39 | |
| 40 | linker sequence |

-continued

| Sequence No. | Name |
|---|---|
| 41 | |
| 42 | |
| 43 | |
| 44 | |
| 45 | |
| 46 | |
| 47 | dCas9-XTEN-AID P182X |
| 48 | dCas9-XTEN-AID P182X |
| 49 | AIDx-saCas9(KKH nickase)-Ugi |
| 50 | AIDx-saCas9(KKH nickase)-Ugi |
| 51 | DMD EXON50 5'SS |
| 52 | sgRNA backbone sequecne |

The invention claimed is:

1. A method for regulating RNA splicing of a gene in a cell, comprising expressing a targeting cytosine deaminase and an sgRNA in the cell to induce mutation of 3' splice site AG to AA of an intron of the gene in the cell, or mutation of 5' splice site GT to AT of an intron of the gene in the cell, or mutation of multiple Cs to Ts in a polypyrimidine region upstream of 3' splice site of an intron of the gene in the cell;

wherein the targeting cytosine deaminase is selected from the group consisting of:

(1) a fusion protein of a cytosine deaminase, or a fragment or mutant thereof retaining enzyme activity, and a Cas enzyme with helicase activity and partial or no nuclease activity; wherein partial nuclease activity refers to only having DNA single-strand break ability, and no nuclease activity refers to having no DNA double-strand break ability; and (2) a fusion protein of a cytosine deaminase, or a fragment or mutant thereof retaining enzyme activity, and a Cpf enzyme with helicase activity and partial or no nuclease activity; wherein partial nuclease activity refers to only having DNA single-strand break ability, and no nuclease activity refers to having no DNA double-strand break ability;

and wherein the sgRNA binds to a sequence having the 5' splice site of the intron of the gene, and the fusion protein mutates the GT to AT at the 5' splice site of the intron of the gene, thereby inducing exon skipping, activating alternative splice sites, inducing mutually exclusive exon switching or intron retention; or the sgRNA binds to a sequence having the 3' splice site of the intron of the gene, and the fusion protein mutates the AG to AA at the 3' splice site of the intron of the gene, thereby inducing exon skipping, activating alternative splice sites, inducing mutually exclusive exon switching or intron retention; or the sgRNA binds to a complementary sequence of the polypyrimidine region of the intron of the gene, and induces the Cs to Ts at the polypyrimidine region of the intron of the gene, thereby enhancing the strength of the 3' splice site and enhancing exon inclusion;

and the method includes expressing the targeting cytosine deaminase and an sgRNA in the cell, wherein the sgRNA is specifically recognized by the Cas enzyme or Cpf enzyme and binds to the sequence having the 5' splice site or the 3' splice site of the intron of the gene, or binds to the complementary sequence of the polypyrimidine region of the intron of the gene.

2. The method according to claim 1, wherein, the fusion protein further contains uracil glycosylase inhibitor (UGI), or the method further includes the step of simultaneously transferring an expression plasmid of UGI to the cell;

or, the method comprises the step of directly introducing the fusion protein and the sgRNA to the cell.

3. The method according to claim 1, wherein, the Cas enzyme is selected from the group consisting of: Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and their homologues; and/or the cytosine deaminase is full-length human-derived activated cytosine deaminase (hAID), or a fragment or mutant that retains enzyme activity, wherein the fragment includes at least a nuclear localization signal (NLS) domain, catalytic domain and APOBEC-like domain of the cytosine deaminase; and/or the fusion protein further comprises one or more of the following sequences: linker sequences, nuclear localization sequences, UGI, and amino acid residues or sequences introduced to construct the fusion protein, promote expression of recombinant proteins, obtain recombinant proteins automatically secreted from host cells, or facilitate the purification of recombinant proteins.

4. The method according to claim 3, wherein, the Cas enzyme is a Cas9 enzyme, and the amino acid sequence of the Cas9 enzyme is amino acid residues 199-1566 of SEQ ID NO: 23, or amino acid residues 42-1452 of SEQ ID NO: 25, or amino acid residues 42-1419 of SEQ ID NO: 33, or amino acid residues 199-1262 of SEQ ID NO: 50; and/or the fragment of the cytosine deaminase comprises at least amino acid residues 1465-1638 of SEQ ID NO: 25; or the fragment of the cytosine deaminase contains at least amino acid residues 1457-1638 of SEQ ID NO: 25;

or, the amino acid sequence of the cytosine deaminase is amino acid residues 1457-1654 of SEQ ID NO: 25;

or the mutant comprises amino acid residues 1447-1629 of SEQ ID NO: 31, or consists of amino acid residues 1447-1629 of SEQ ID NO: 31.

5. The method according to claim 4, wherein the amino acid sequence of the fusion protein is SEQ ID NO: 23, 25, 27, 29, 31, 33, 48, or 50, or amino acids 26-1654 of SEQ ID NO: 25, or amino acids 26-1638 of SEQ ID NO: 27, or amino acids 26-1629 of SEQ ID NO: 31, or amino acids 26-1638 of SEQ ID NO: 33, or amino acids 26-1629 of SEQ ID NO: 48.

6. The method according to claim 1, wherein the Cas enzyme is a Cas9 enzyme selected from the group consisting of: Cas9 from *Streptococcus pyogenes*, Cas9 from *Staphylococcus aureus*, and Cas9 from *Streptococcus thermophilus*.

7. The method according to claim 1, wherein the method is used for treatment of a disease caused by genetic mutations or a tumor that benefits from changes in the proportion of different splicing isoforms of functional proteins.

8. The method according to claim 7, wherein the disease caused by genetic mutations is selected from the group consisting of: Duchenne myasthenia caused by mutations in the dystrophin (DMD) gene, survival motor neuron (SMN), thalassemia caused by 647G>A mutation of β hemoglobin intron 2 (IVS2), familial hypercholesterolemia and premature aging caused by lamin A/C gene (LMNA) mutation; the splicing isoform is selected from the group consisting of: conversion of signal transducer and activator of transcription 3α (Stat3α) to signal transducer and activator of transcription 3β (Stat3β), conversion of pyruvate kinase M2 (PKM2) to pyruvate kinase M1 (PKM1), murine double minute 4 (MDM4) exon 6 skipping, B-cell lymphoma 2 (Bcl2) alternative splice sites selection, and low-density lipoprotein receptor-related protein 8 (LRP8) exon 8 skipping.

9. The method according to claim 1, wherein the fusion protein comprising a Cas protein with helicase activity and partial or no nuclease activity, a cytosine deaminase or a fragment or mutant thereof that retains enzyme activity, and UGI, and an optional nuclear localization sequence and linker sequence.

10. The method according to claim 1, wherein the fragment of the cytosine deaminase comprises at least amino acid residues 1465-1638 of SEQ ID NO: 25;

or, the amino acid sequence of the cytosine deaminase is amino acid residues 1457-1654 of SEQ ID NO: 25;

or, the mutant comprises amino acid residues 1447-1629 of SEQ ID NO: 31, or consists of amino acid residues 1447-1629 of SEQ ID NO: 31.

11. The method according to claim 1, wherein the fusion protein or an expression vector thereof is comprised in a composition or a kit comprising the composition, and the composition or the kit further comprises the sgRNA recognized by the fusion protein in the composition or its expression vector.

12. The method according to claim 11, wherein the kit comprises a virus particle that enables the expression of the fusion protein and sgRNA in the cell.

13. The method according to claim 1, wherein a target binding region of the sgRNA binds to a sequence in DMD exon 50 having the 5' splice site; and the target binding region of the sgRNA is SEQ ID NO: 51.

14. The method according to claim 1, wherein the sgRNA binds to a complementary sequence of the polypyrimidine region of the intron of the gene, and induces more than 70% of the Cs to Ts at the polypyrimidine region of the intron of the gene, thereby enhancing the strength of the 3' splice site and enhancing exon inclusion.

* * * * *